(12) United States Patent
Bigg et al.

(10) Patent No.: US 6,300,499 B1
(45) Date of Patent: Oct. 9, 2001

(54) α1-ADRENERGIC RECEPTOR ANTAGONISTS

(75) Inventors: Dennis Bigg, Gif-sur-Yvette; Pierre Etienne Chabrier de Lassauniere, Paris; Serge Auvin, Saint-Michel-sur-Orge; Michel Auguet, Palaiseau, all of (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/155,535

(22) PCT Filed: Apr. 4, 1997

(86) PCT No.: PCT/FR97/00615

§ 371 Date: Sep. 28, 1998

§ 102(e) Date: Sep. 28, 1998

(87) PCT Pub. No.: WO97/37983

PCT Pub. Date: Oct. 16, 1997

Related U.S. Application Data

(63) Continuation-in-part of application No. 08/628,276, filed on Apr. 5, 1996, now abandoned.

(51) Int. Cl.[7] .................. C07D 241/04; A61K 31/395
(52) U.S. Cl. .................. 544/358; 544/402; 514/252.12
(58) Field of Search .................. 514/252.12; 544/402, 544/358

(56) References Cited

U.S. PATENT DOCUMENTS 2,722,529 * 11/1955 Fleming et al. .................. 514/249

FOREIGN PATENT DOCUMENTS

| | | |
|---|---|---|
| 0048045 | 3/1982 | (EP) . |
| 048045 * | 3/1982 | (EP) . |
| 0343961 | 11/1989 | (EP) . |
| 0395313 | 10/1990 | (EP) . |
| 9402437 | 7/1994 | (EP) . |
| 9503605 | 9/1995 | (EP) . |
| 0434561 | 6/1991 | (FR) . |
| 2263110 | 7/1993 | (GB) . |
| 9300295 | 4/1993 | (SE) . |
| 9407121 | 6/1994 | (WO) . |

* cited by examiner

*Primary Examiner*—Richard L. Raymond
*Assistant Examiner*—Sudhaker Patel
(74) *Attorney, Agent, or Firm*—Bierman, Muserlian and Lucas

(57) ABSTRACT

Phenylpiperazine derivatives having high affinity for the $\alpha_1$-adrenoreceptor and pharmaceutical compositions containing them. Also disclosed is a method of using the such derivatives to treat benign prostatic hyperplasia.

38 Claims, No Drawings

α1-ADRENERGIC RECEPTOR ANTAGONISTS

This application is a 371 of PCT/FR97/00615 filed Apr. 4, 1997 which is a CIP of Ser. No. 08/628,276 filed Apr. 5, 1996 ABN.

Neuroreceptors are considered as dynamic entities which constitute an accessible means of clinical manipulation. The norepinephrine sympathic neurotransmitter and the epinephrine surrenal hormone regulate numerous physiological activities through interactions with the α- and β-adrenergic receptors. The $α_1$-adrenergic receptors are mediators of a number of the physiological effects of catecholamines, in particular glycogenolysis, contraction of the vascular and genito-urinary smooth muscle, hyperpolarisation of the intestinal smooth muscle, the contractile force and cardiac arythmia.

In one of its aspects, the invention relates to a compound of formula I:

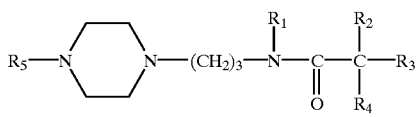

(I)

in which:
- $R_1$ represents a hydrogen, a lower alkyl, or an aryl-lower alkyl;
- $R_2$ represents a hydrogen, a lower alkyl, $OR_6$, $S(O)_mR_6$ (in which m is 0, 1, or 2), $NHS(O)_nR_6$ (in which n is 1 or 2), $OC(O)R_6$, $CONR_6R_7$, $NR_6R_7$, or $N(R_7)C(O)R_6$;
- $R_3$ and $R_4$, independent of each other, represent hydrogen, or one of the following substituted compounds (i.e., one to four times on the carbon or nitrogen atoms) or non-substituted: a lower alkyl, a cycloalkyl, an aryl, a lower aryl-alkyl, a heterocycle, or a heterocycle-lower alkyl, in which said substituent is a lower alkyl, a halogen, $OR_6$, $SR_6$, $NR_6R_7$, CN, $NO_2$, $CF_3$, a heterocycle, or an aryl, or $R_3$ and $R_4$ constitute, together with the carbon atom to which they are jointly linked, an aryl or a substituted heterocycle (i.e. in one to four locations) or non-substituted, in which said substituent is a lower alkyl, OH, or a hydroxyl-lower alkyl;
- $R_5$ is a substituted aryl (i.e., on one to four carbon atoms) or non-substituted, in which said substituent is a lower alkyl, a cycloalkyl, a hydroxyl-lower alkyl, a hydroxyl-cycloalkyl, a alkoxy-lower alkyl, an alkoxy-cycloalkyl, a halogen, $OR_6$, $SR_6$, $NR_6R_7$, or CN; and
- $R_6$ and $R_7$, independent of each other, represent a hydrogen or one of the following compounds substituted (i.e., on one to four carbon atoms) or non-substituted: lower alkyl, aryl or aryl-lower alkyl, in which said substituent is a lower alkyl, a halogen, or a lower alkoxy; in which if $R_3$ or $R_4$ represents a hydrogen, $R_2$ does not represent OH; or one of its pharmaceutically acceptable salts.

In one of the embodiments, $R_1$ represents hydrogen or a lower alkyl, $R_2$ represents a hydrogen, a lower alkyl, $OR_6$ (in which $R_6$ represents a hydrogen or an aryl-lower alkyl), $SR_6$ (in which $R_6$ is a lower alkyl), $NH_2$, $NHSO_2R_6$ (in which $R_6$ is a lower alkyl or an aryl-lower alkyl), $OC(O)R_6$ (in which $R_6$ is an aryl-lower alkyl) or $CONR_6R_7$ or $N(R_7)C(O)R_6$ (in which $R_7$ represents a hydrogen and $R_6$ represents an aryl-lower alkyl); $R_5$ represents a substituted or non-substituted phenyl, in which said substituent is a lower alkyl, CN, a halogen, a hydroxy-lower alkyl, a hydroxy-cycloalkyl, a lower alkoxy-lower alkyl, or $OR_6$ (in which $R_6$ is a lower alkyl); and $R_3$ and $R_4$, independent of one another, represent a hydrogen or one of the following substituted or non-substituted compounds: a lower alkyl, a cycloalkyl, or an aryl, in which said substituent is a halogen, $OR_6$ (in which $R_6$ is a lower alkyl), or an aryl.

In another embodiment, $R_1$ represents a hydrogen and $R_5$ represents 2,5-dimethyl-phenyl; $R_2$ represents $OR_6$ (in which $R_6$ represents a hydrogen, a lower alkyl, or an aryl-lower alkyl); and $R_3$ represents a lower alkyl and $R_4$ represents a phenyl.

In another embodiment, $R_3$ and $R_4$, together with the carbon atom to which they are jointly linked, constitute an aryl or a heterocycle; $R_1$ represents a hydrogen and $R_5$ represents 2-methoxy-phenyl or 2,5-dimethyl-phenyl; and $R_2$ represents $OR_6$ (in which $R_6$ represents a hydrogen, a lower alkyl, or an aryl-lower alkyl).

In yet another embodiment, $R_3$ and $R_4$, together with the carbon atom to which they are jointly linked, constitute 9-xanthenyl or 9-fluorenyl.

The following examples are examples of compounds according to the present invention:

Coumpound No.

1

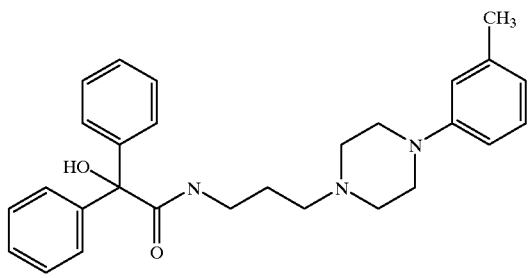

2

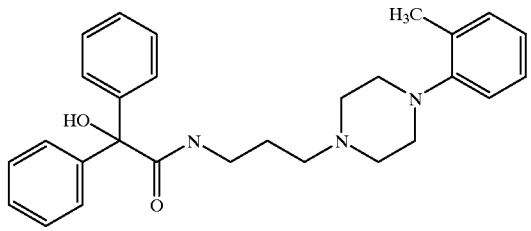

3

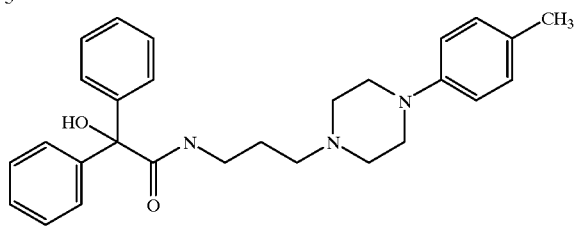

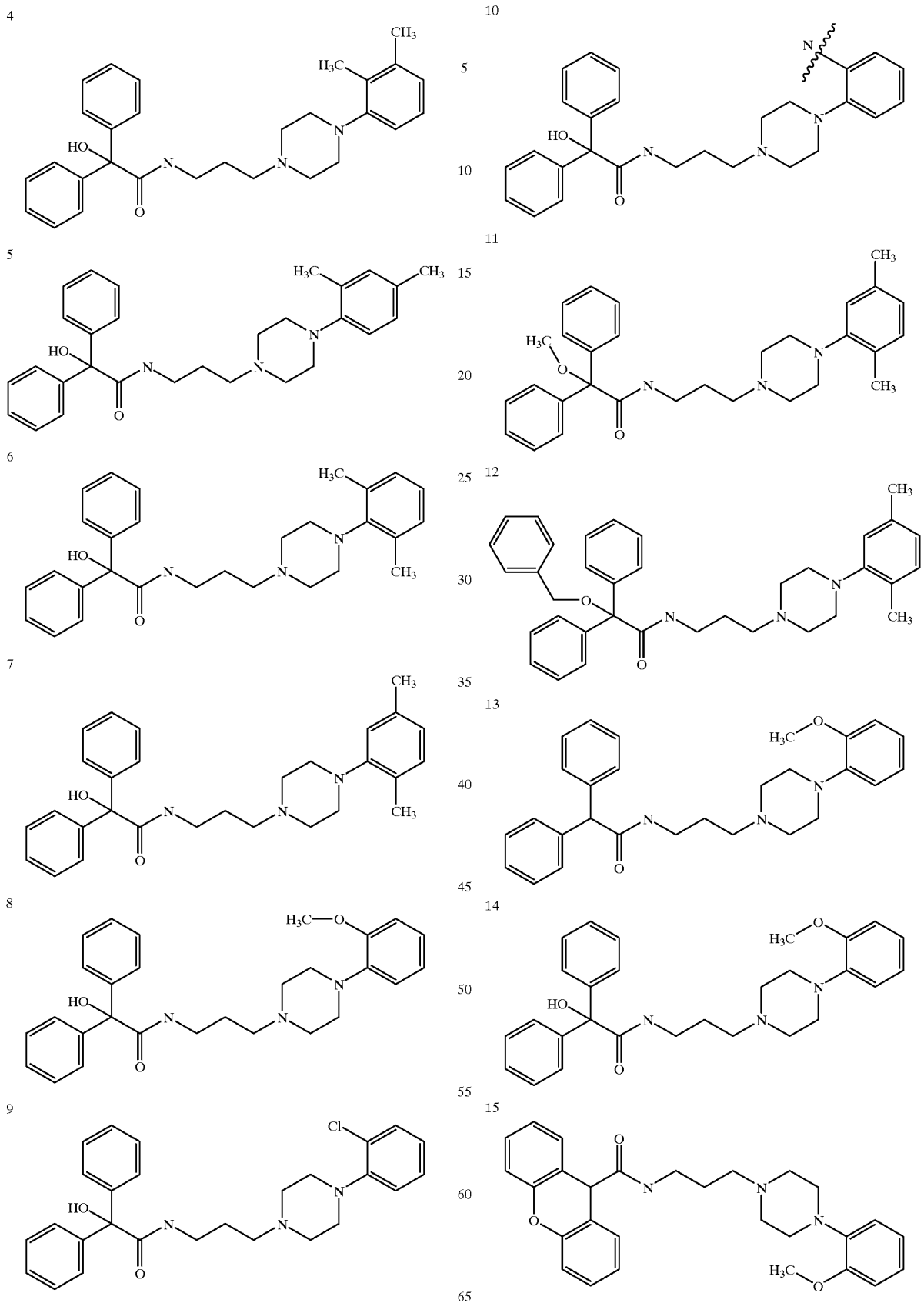

16
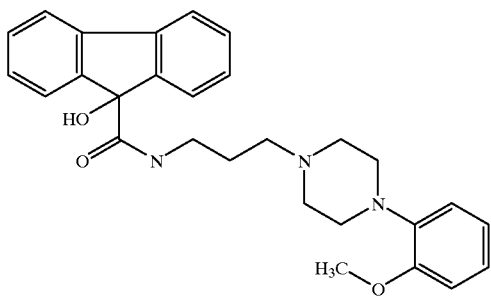
17
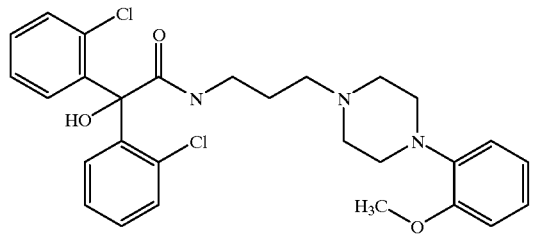
18
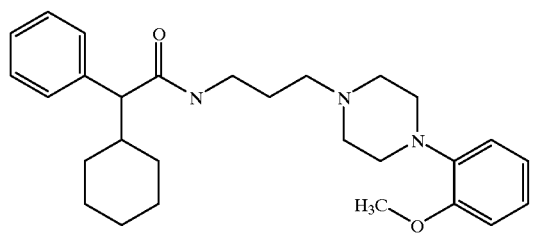
19
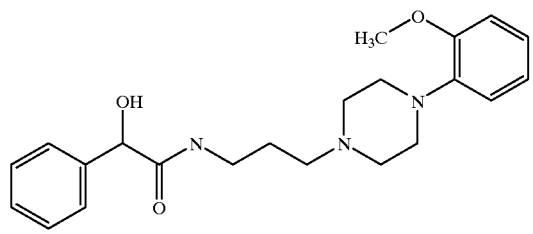
20
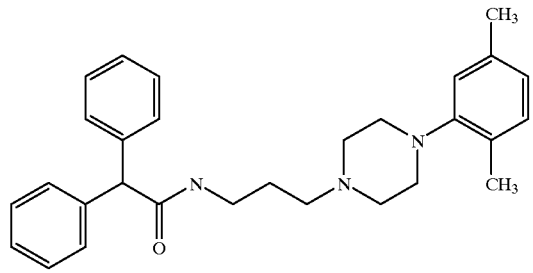
21
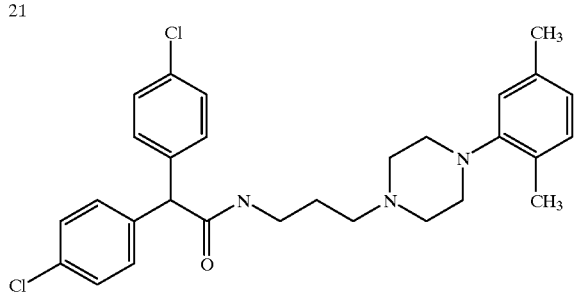
22
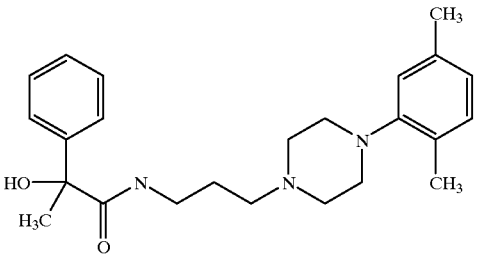
23
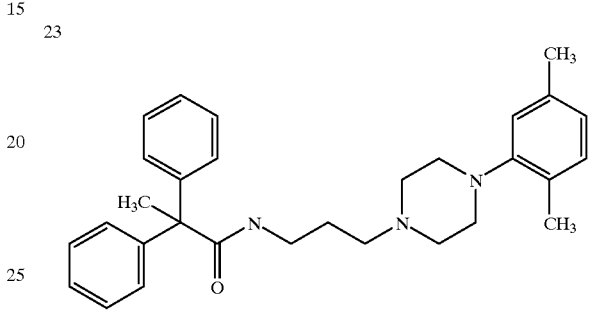
24
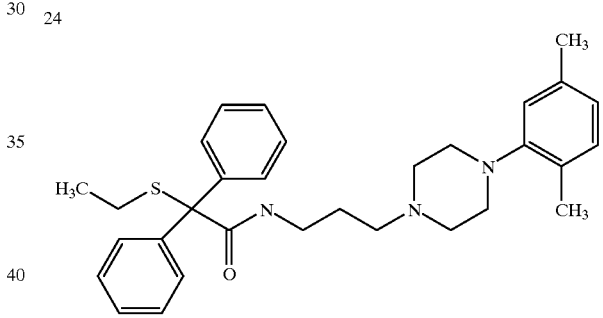
25
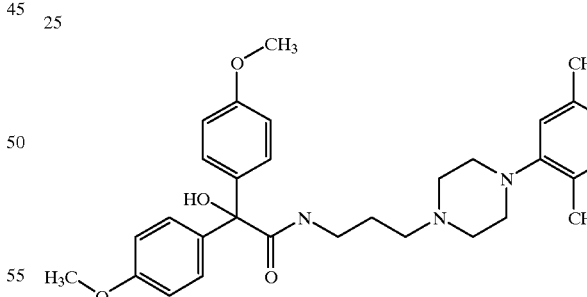
26
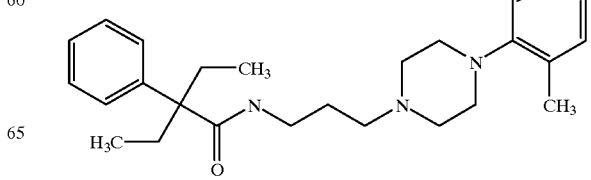

27
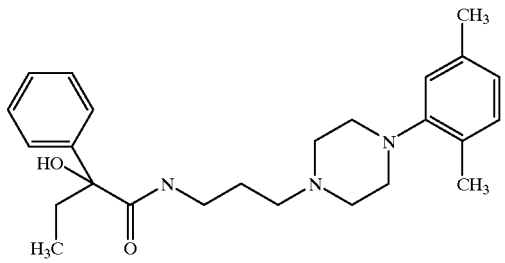
28
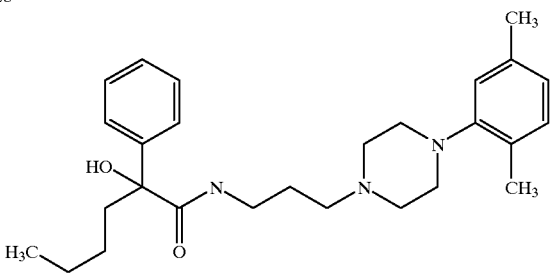
29
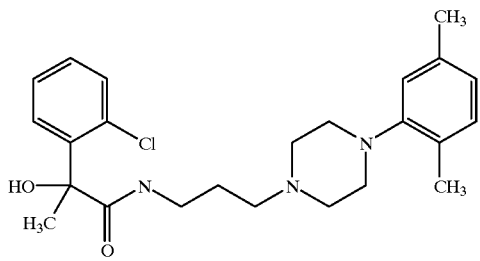
30
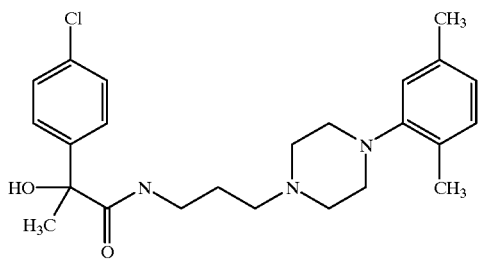
31
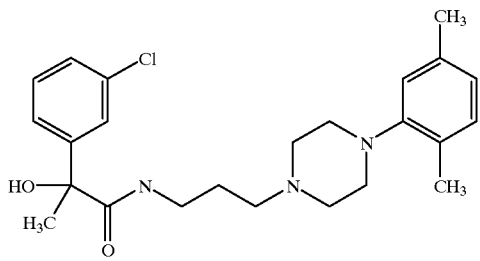
32
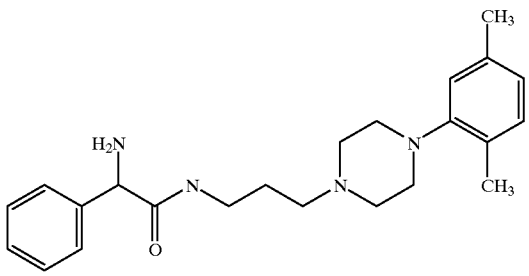
33
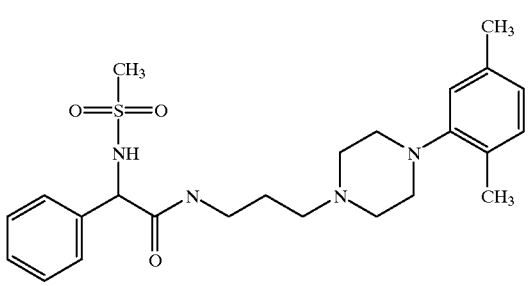
34
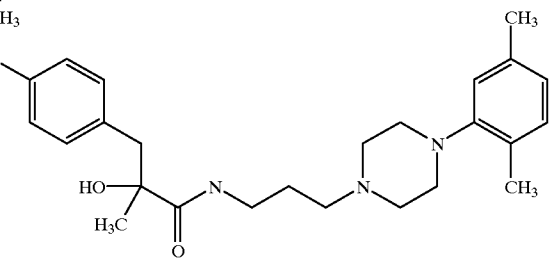
35
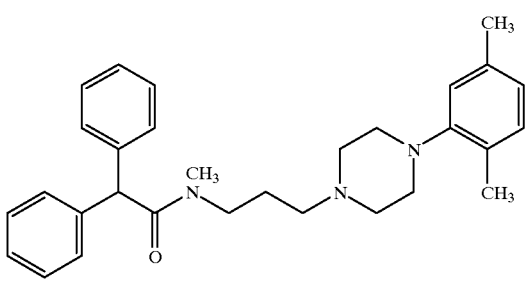
36
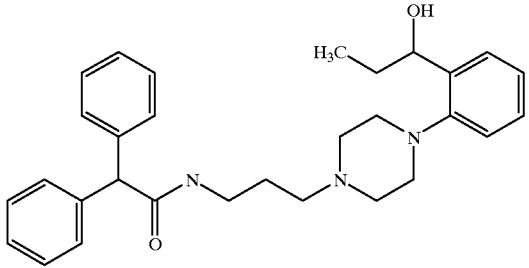

37
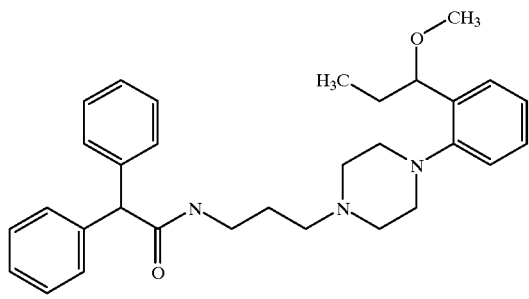
38
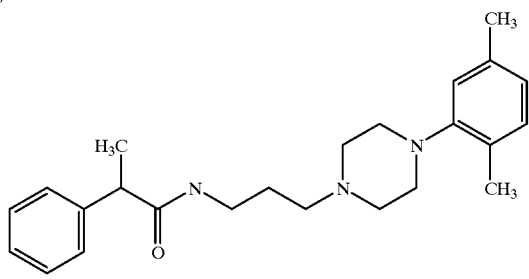
39
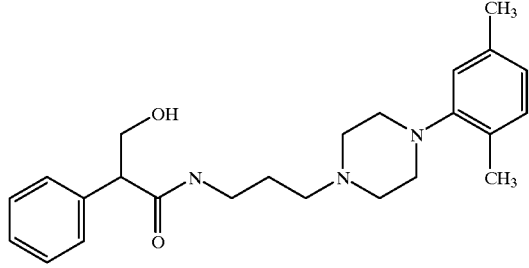
40
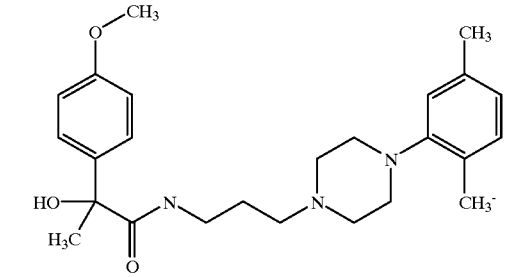
41
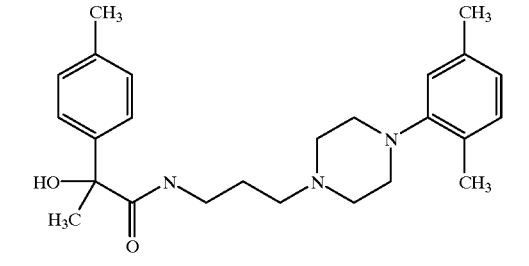
42
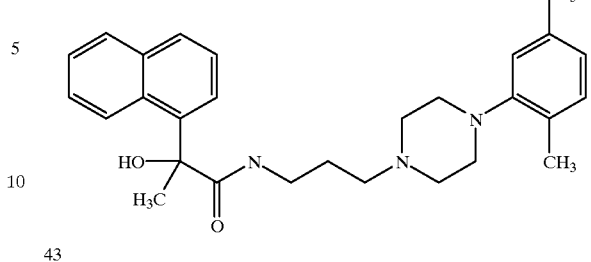
43
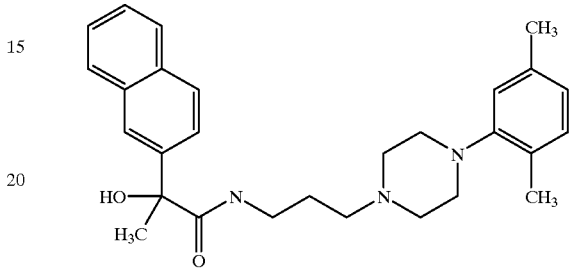
44
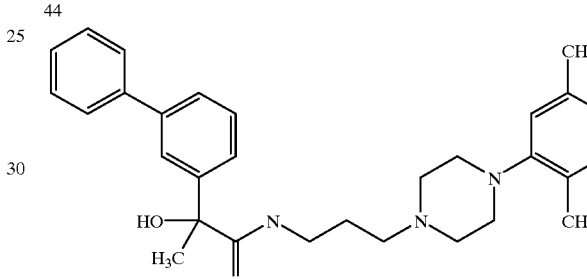
45
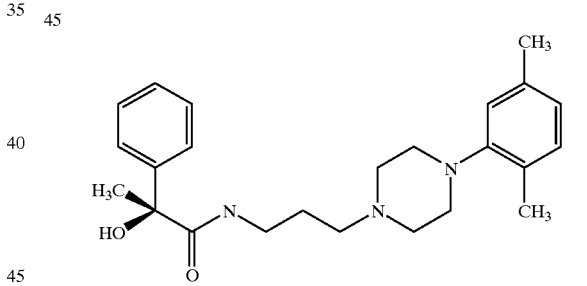
46
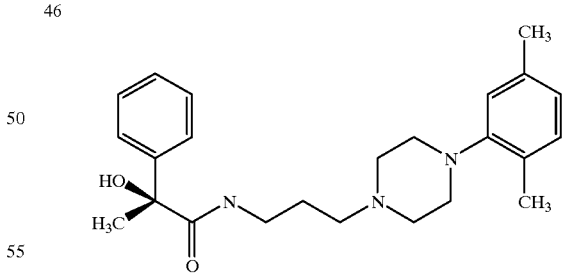
47
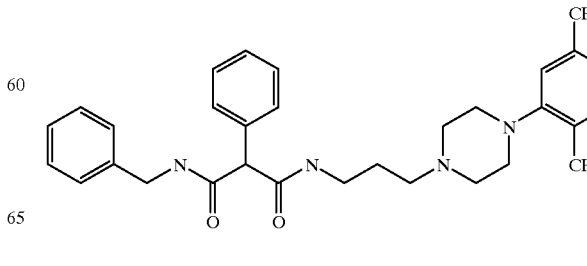

-continued

48
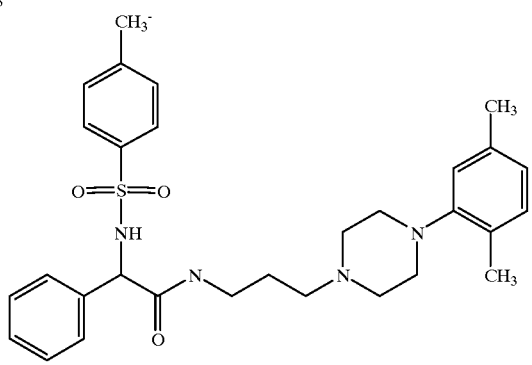

49
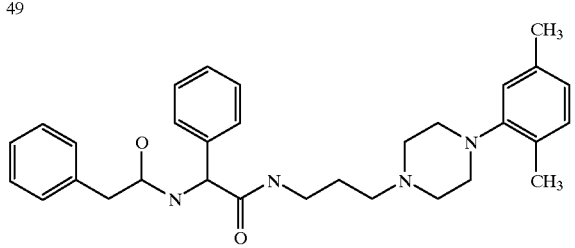

50
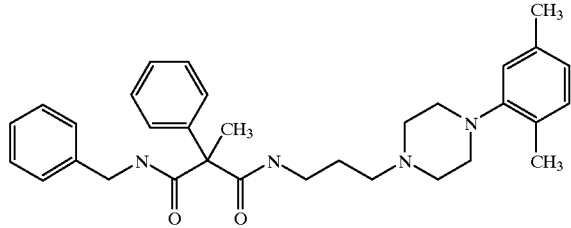

51
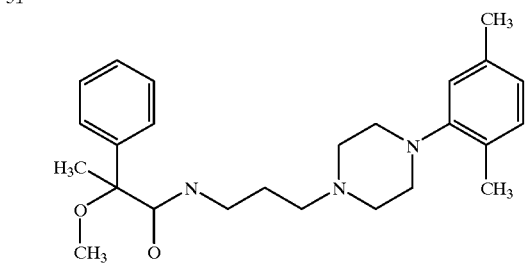

52
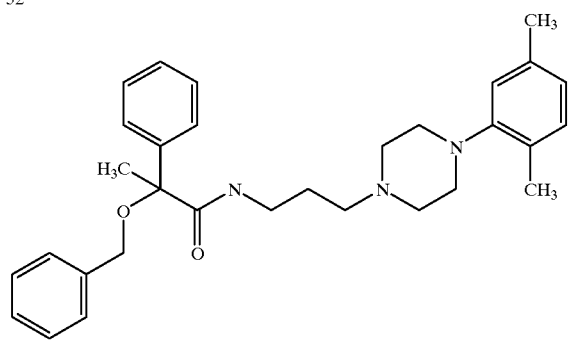

-continued

53
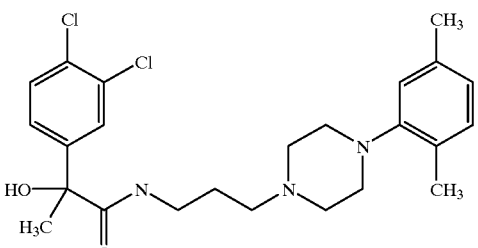

54
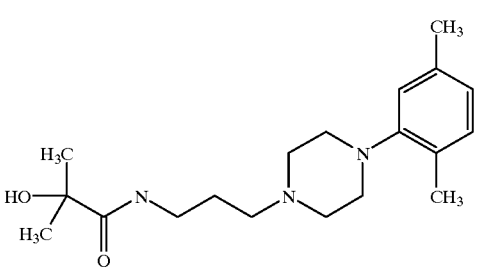

55
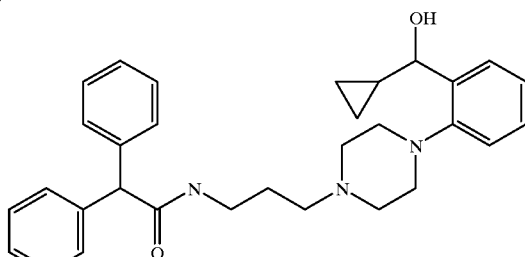

56
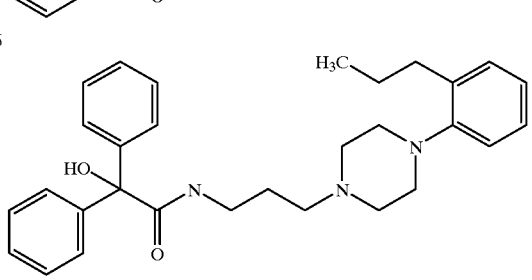

According to another aspect, the present invention relates to the use as medicaments of products of general formula I as described above, as well as a pharmaceutical composition containing a compound of formula I

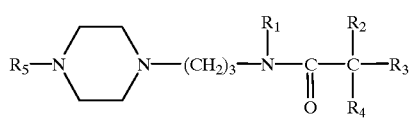

(I)

in which:

$R_1$ represents a hydrogen, a lower alkyl, or an aryl-lower alkyl;

$R_2$ represents a hydrogen, a lower alkyl, $OR_6$, $S(O)_m R_6$ (in which m is 0, 1, or 2), $NHS(O)_n R_6$ (in which n is 1 or 2), $CONR_6 R_7$, $NR_6 R_7$, or $N(R_7)C(O)R_6$;

$R_3$ and $R_4$, independent of one another, represent hydrogen or one of the following substituted or non-substituted compounds: a lower alkyl, a cycloalkyl, an aryl, an aryl-lower alkyl, a heterocyle, or a heterocycle-lower alkyl, in which said substituent is a lower alkyl, a halogen $OR_6$, $SR_6$, $NR_6R_7$, CN, $NO_2$, $CF_3$, a heterocycle, or an aryl, or $R_3$ and $R_4$ constitute, together with the carbon atom to which they are jointly linked, a heterocycle;

$R_5$ is a substituted or non-substituted aryl, in which said substituent is a lower alkyl, a hydroxyl-lower alkyl, an alkoxy-lower alkyl, a halogen, $OR_6$, $SR_6$, $NR_6R_7$ or CN; and $R_6$ and $R_7$, independent of one another represent a hydrogen or one of the following substituted or non-substituted compounds: lower alkyl, aryl or aryl-lower alkyl, in which said substituent is a lower alkyl, a halogen, or a lower alkoxy; or one of its pharmaceutically acceptable salts.

According to one embodiment, $R_1$ represents a hydrogen, $R_5$ represents 2,5-dimethyl-phenyl; $R_2$ represents $OR_6$ (in which $R_6$ represents a hydrogen, a lower alkyl, or an aryl-lower alkyl); $R_3$ represents a lower alkyl, and $R_4$ represents a phenyl.

As used here, a "lower alkyl" includes saturated aliphatic hydrocarbon groups at the same time linear, branched, or straight chain, having from 1 to 6 carbon atoms. Examples of lower alkyl groups include methyl, ethyl, propyl, isopropyl, butyl, t-butyl, and similar.

As used here, a "cyclo-alkyl" includes any cyclic non-aromatic hydrocarbon fragment having from 3 to 10 carbon atoms in which 3 to 8 of the carbon atoms constitute a cycle. Examples of such fragments include, but are not limited to, cyclopropyl, methyl-cyclopropyl, ethyl-cyclopropyl, cyclobutyl, cyclopentyl, cyclohexyl, cyclopropyl-methyl, cyclopropyl-ethyl, and cyclohexyl-ethyl.

As used here, an "aryl" includes any stable monocyclic, bicyclic, or tricyclic carbon nucleus (nuclei) or cycle(s) containing up to 7 members in each cycle, in which at least one cycle is aromatic. Examples of such aryl groups include phenyl, the naphthyl, anthracenyl, biphenyl, tetrahydronaphthhyl, indanyl, phenanthrenyl, and similar.

As used here, a "lower alkoxy" includes saturated aliphatic hydrocarbon groups at the same time linear, branched, and straight chain, having form 1 to 6 carbon atoms and an oxygen atom. Examples of lower alkoxys include methoxy, ethoxy, propoxy, isopropoxy, butoxy, and similar.

The term heterocycle, as used here, represents a heterocyclic nucleus or cycle containing a stable monocycle with 5 to 7 members or a stable bicycle with 8 to 11 members or a tricycle stable with 11 to 15 members, which is either saturated or unsaturated, and which consists of carbon atoms and from 1 to 4 heteroatoms chosen from the group consisting of N, O, and S, and including any bicyclic group in which any one of the heterocyclic cycles defined above is linked to the benzene nucleus. The heterocyclic cycle can be linked to any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulphone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthhyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydroquinolinyl, thiamorpholinyl, thiamorpholinyl-sulphoxide, thiazolyl, thiazolinyl, thienofuryl, thienothienyl, thienyl, 9-xanthenyl, and similar.

As used here, a halogen represents a chloryl, fluoryl, brominyl, or iodo.

The compounds of the present invention can contain an asymmetrical centre and be presented as racemates, racemic mixtures, or individual diastereomers, with all possible isomers, including optical isomers, all being included in the present invention. In order to simplify, when any specific configuration is not described in the structural formulae, it is understood that all enantiomeric forms and their mixtures are represented. In one embodiment, the carbon atom linked to $R_2$, $R_3$, and $R_4$ is in "S" configuration.

The compounds of this invention can be provided in the form of pharmaceutically acceptable salts. Acceptable salts include, but are not limited to, the acid addition salts of inorganic acids such as the hydrochloride, the sulphate, the phosphate, the diphosphate, the hydrobromide, and the nitrate or of organic acids such as the acetate, the maleate, the fumarate, the tartarate, the succinate, the citrate, the lactate, the methanesulphonate, the p-toluene-sulphonate, the pamoate, the salicylate, the oxalate, and the stearate. The salts formed from bases such as sodium or potassium hydroxide are also included in the present invention, when this is possible. For other examples of pharmaceutically acceptable salts, see "Pharmaceutical Salts", J. Pharm. Sci. 66:1 (1977).

The present invention also relates to a treatment method for disorders of which the $\alpha_1$-adrenergic receptor constitutes a mediator. Examples of such disorders include hypertension, disorders of the lower urinary apparatus (for example benign hyperplasia of the prostate, arythmia, myocardial ischemia, high serous lipidic concentrations, glaucoma, disorders relating to the motility of the gastrointestinal apparatus, cholesterol synthesis, erectile dysfunction, Raynaud's disease, congestive cardiac pathologies, portal hypertension, and pluri-medicinal resistance, cirrhosis.

The invention also relates to the use of products of general formula I as described above, for the preparation of a medicament intended to treat benign hyperplasia of the prostate, portal hypertension and cirrhosis.

In another embodiment, the invention relates to a treatment method for portal hypertension, the method consisting of the administration of an effective therapeutic quantity of a compound having a $K_b$ inhibition of the contraction of the rat's portal vein which is at least five times (for example, at least ten or twenty times) lower than the $K_b$ of said compound for the inhibition of the contraction of the rat's aorta, in which said compound is linked to the $\alpha_1$-adrenergic receptor with a Ki of at least 1 mM (for example, at least 10 nM or 1 nM), i.e. as described in the trials described here. In yet another embodiment, said compound has a $K_b$-inhibition of the contraction of the rabbit's portal vein which is at least twice (for example, at least five or nine times) lower than the $K_b$ of said compound pour the inhibition of the contraction of the rabbit's saphenous vein, i.e. as described in the trials described here.

A subject of the invention is also the use of compounds having a $K_b$ inhibition of the contraction of the rat's portal vein which is at least five times (for example, at least ten or twenty times) lower than the $K_b$ of said compound for the inhibition of the contraction of the rat;'s aorta, in which said compound is linked to the $\alpha_1$-adrenergic receptor with a Ki of at least 1 mM (for example, at least 10 nM or 1 nM), for the preparation of a medicament intended to treat portal hypertension or cirrhosis.

A subject of the invention is also a treatment method for portal hypertension, said method comprising the administration of an effective therapeutic quantity of a compound of formula $I_M$:

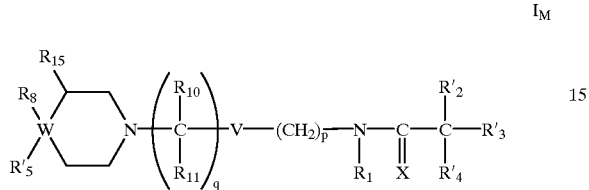

$I_M$ in which

W represents a nitrogen or carbon atom;

$R_1$ represents a hydrogen, a lower alkyl, an aryl-lower alkyl, CN, $CO_2R_9$, $CON(R_9)_2$, a cycloalkyl or $(CH_2)_p CO_2R_9$;

$R'_2$ represents a hydrogen, a lower alkyl, $OR_6$, $S(O)_m R_6$ in which m is 0, 1 or 2, $NHS(O)_n R_6$ in which n is 1 or 2, $OC(O)R_6$, $C(O)NR_6R_7$, $NR_6R_7$, $N(R_7)C(O)R_6$, $CO_2R_{10}$, $(CH_2)_p$—$CO_2R_{10}$, $OR_{12}$, N—$R_{12}$—$R_{13}$, $(CH_2)_p CN(R_{10})_2$ or $CR'_2$ forms a cyclopropyl cycle and one of $R'_3$ and $R'_4$ does not exist.

Each of $R'_3$ and $R'_4$, independent of one another, represents a hydrogen or one of the following substituted or non-substituted compounds: lower alkyl or alkoxy, a cycloalkyl, an aryl, an aryl-lower alkyl, a heterocycle, a heterocycle-lower alkyl or $NR'_{10}R''_{10}$, in which said substituent is a lower alkyl optionally substituted by one or more halogen atoms, a halogen, $OR_6$, $SR_6$, $NR_6R_7$, CN, $NO_2$, a heterocycle, an aryl or a methylenedioxy on two adjacent carbons, or $R'_3$ and $R'_4$, together with the carbon atom to which they are jointly linked, form a substituted or non-substituted aryl or a heterocycle, in which said substituent is a lower alkyl, OH, or a hydroxy-lower alkyl;

$R'_5$ is a substituted or non-substituted lower alkyl, aryl or heterocycle radical, in which said substituent is a lower alkyl, optionally substituted by one or more halogen atoms, a cyclo-alkyl, a hydroxy-lower alkyl, a hydroxy-cycloalkyl, an alkoxy-lower alkyl, an alkoxy-cycloalkyl, a halogen, a methylenedioxy on two adjacent carbons, $OR_6$, $SR_6$, $NR_6R_7$, CN, $CO_2R_{10}$, $(CH_2)_p CON(R_{10})_2$ or $(CH_2)_p CO_2R_{10}$;

each of $R_6$ and $R_7$, independent of one another, represents a hydrogen or one of the following substituted or non-substituted compounds: a lower alkyl, an aryl or an aryl-lower alkyl, in which said substituent is a lower alkyl, a halogen, or a lower alkoxy;

$R_8$ is chosen from the hydrogen, cyano, $CO_2R_9$, CON$(R_9)_2$ or aryl, it being understood that when W is a nitrogen atom, $R_8$ does not exist;

each of $R_9$, $R_{10}$, $R'_{10}$, $R''_{10}$ and $R_{11}$, independent of one another, is a hydrogen, a lower alkyl or a cycloalkyl, the alkyl and cycloalkyl being optionally substituted by one or more halogens;

each of $R_{12}$ and $R_{13}$, independent of one another, represents hydrogen, a substituted or non substituted lower alkyl or a cycloalkyl radical, CHO, $COR_{10}$, $CONR_{10}R_{11}$ or $(CH_2)_p OR_{10}$;

V is chosen from

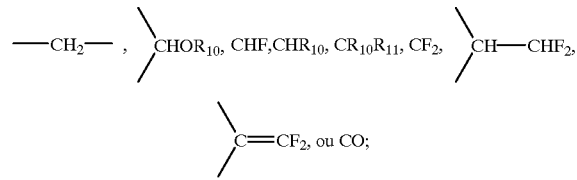

q is an integer from 0 to 3;

p is an integer from 0 to 3;

X is chosen from oxygen, sulphur or $NR_{14}$, in which $R_{14}$ is hydrogen, cyano or $SO_2R_{10}$;

$R_{15}$ is hydrogen or hydroxy;

it being understood that when n=p=0, V does not represent $CH_2OR_{10}$.

or one of its pharmaceutically acceptable salts.

A subject of the invention is also the use of products of formula $I_M$ for the preparation of a medicament intended to treat portal hypertension or cirrhosis.

The products of formula $I_M$ the preparation of which is not described in the present Application, can be prepared by the process described in the Application WO 96/40136, the contents of which are incorporated in the present Application by way of reference. A subject of the invention is also the use of compounds as described in the Application WO 96/40136, for the preparation of a medicament intended to treat portal hypertension or cirrhosis.

A subject of the invention is also a treatment method for portal hypertension or cirrhosis, said method comprising the administration of an effective therapeutic quantity of a compound of formula $I_N$:

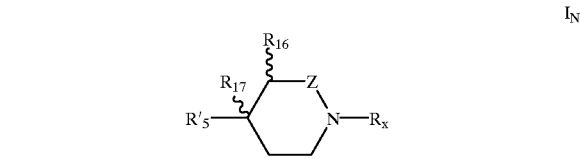

$I_N$ in which $R'_5$, $R_9$ and $R_{10}$ have the meaning indicated in claim 35;

Z represents a $CHR_{18}$ or $NHR_9$ radical;

$R_x$ is chosen from the radicals

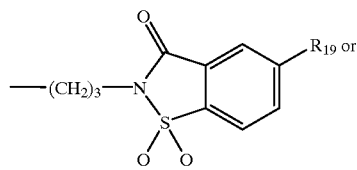

-continued

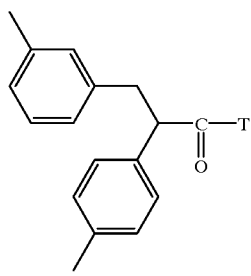

in which $R_{19}$ represents a hydrogen atom or a chlorine atom;

T represents a —NH—$(CH_2)_3$ or

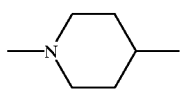

radical;

$R_{16}$, $R_{17}$ and $R_{18}$ are chosen from hydrogen and the cyano, aryl, heterocycle, $CONR_9R_{10}$, $CO_2R_9$ or $SO_2R_9$ radicals, as well as the use of products of formula $I_N$ for the preparation of a medicament intended to treat portal hypertension or cirrhosis.

The products of formula $I_N$ can be prepared by the process described in the Application WO 96/40135, the contents of which is incorporated in the present Application by way of reference.

A subject of the invention is also the use of compounds as described in the Application WO 96/40135, for the preparation of a medicament intended to treat portal hypertension or the cirrhosis.

A subject of the invention is also a treatment method for portal 'hypertension, said method comprising the administration of an effective therapeutic quantity of a compound of formula $I_R$:

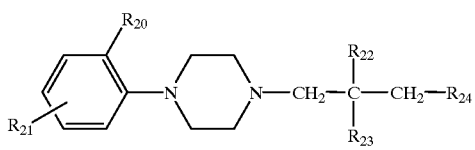

$I_R$ in which:

$R_{20}$ represents acetylamino, amino, cyano, trifluoroacetylamino, a halogen, a hydrogen, hydroxy, nitro, methylsulphonylamino, 2-propynyloxy or one of the following radicals substituted one to three times by halogen atoms or non-substituted: a lower alkl, a cycloalkyl lower, a cycloalkyl-lower alkyl, a lower alkoxy, a cycloalkyloxy, a cycloalkyl-lower alkoxy or a lower alkylthio; or one of the following radicals: an aryl, an aryl-alkyl, a heterocycle, a heterocycle-lower alkyl, an aryloxy, an aryl-lower alkoxy, a heterocycle-oxy or a heterocycle-lower alkoxy, in which the aryl radical or heterocycle are optionally substituted by one or two independent radicals chosen from a halogen atom and the cyano radical;

$R_{21}$ represents CN, a halogen, a hydrogen, hydroxy or one of the following radicals optionally substituted by one to three halogen atoms a lower alkyl or a lower alkoxy;

$R_{22}$ and $R_{23}$ represent, independently, hydrogen or methyl or, together, ethylene;

$R_{24}$ represents one of the following compounds of formula $I_{Ra}$, $I_{Rb}$, $I_{Rc}$ and $I_{Rd}$:

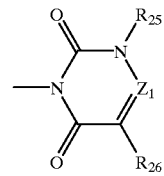

$I_{Ra}$

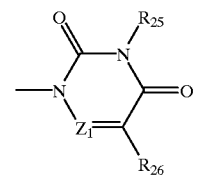

$I_{Rb}$

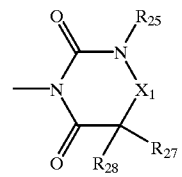

$I_{Rc}$

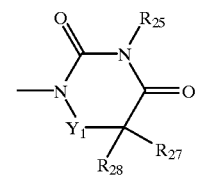

$I_{Rd}$ in which:

$X_1$ represents C(O), $CH_2$ or CH(OH);

$Y_1$ represents $CH_2$ or CH(OH);

$Z_1$ represents N or $C(R_{29})$, in which $R_{29}$ represents hydrogen, a lower alkyl or hydroxy;

$R_{25}$ represents a hydrogen, one of the following radicals optionally substituted by one to three halogen atoms: a lower alkyl, a cycloalkyl, a cycloalkyl-lower alkyl; or one of the following radicals: an aryl, a heterocycle, an aryl-lower alkyl or a heterocycle-lower alkyl, in which the aryl radical or heterocycle are optionally substituted by one to three radicals chosen from the halogen atom, cyano, a lower alkoxy, a lower alkyl or an aryl;

$R_{26}$ represents $R_{30}C(O)$—, carbamoyl, cyano, di(lower alkyl)amino, a halogen, a hydrogen, hydroxy, hydroxyiminomethyl, $R_{30}S$, $R_{30}SO_2$; one of the following radicals substituted by one to three radicals chosen from a halogen, hydroxy or a lower alkoxy, or non-substituted: a lower alkyl, a cycloalkyl, a lower alkoxy or a lower alkoxy-lower alkyl; or one of the following radicals: an aryl, a heterocycle, an aryl-lower alkyl or a heterocycle-lower alkyl, in which the aryl radical or heterocycle are optionally substituted by one to three radicals chosen from a halogen, cyano, a lower alkoxy, a lower alkyl or an aryl; or $R_{26}$ and $R_{29}$ form together the —$CH_2$—$(CH_2)_2$—$CH_2$— radical;

$R_{27}$ and $R_{28}$ represent, independently, a hydrogen, hydroxy, methyl or ethyl;

$R_{30}$ represents a alkyl lower;

or one of its pharmaceutically acceptable salts or one of its N-oxides; and more particularly, in the case where the compound $I_R$ represents 3-[3-[4-[4-fluoro-2-(2,2,2-trifluoroethoxy)phenyl]-1-piperazinyl]propyl]-dihydro-2,4-(1H, 3H)pyrimidine dione.

A subject of the invention is also the use of a product of formula $I_R$ as defined above, for the preparation of a medicament intended to treat portal hypertension or cirrhosis.

The products of formula $I_R$ can be prepared by the process described in the Application EP 748 800, the contents of which is incorporated in the present Application by way of reference.

A subject of the invention is also the use of compounds as described in the Application EP 748 800, for the preparation of a medicament intended to treat portal hypertension or cirrhosis.

An effective therapeutic quantity of a compound of said invention and a pharmaceutically acceptable support substance (for example, magnesium carbonate, lactose, or a phospholipid with which the therapeutic compound can form a micelle) form together with a pharmaceutical composition (for example, a pill, a tablet, a capsule, or a liquid) for the administration (for example, by oral, intravenous, transdermic, or sub-cutaneous route) to a patient having need of the compound. The pill, tablet or gelatine capsule can be covered in a substance which is capable of protecting the composition from the action of gastric acid or intestinal enzymes in the stomach of the patient for a sufficient period of time to allow the composition to pass in a non-digested form into the small intestine of the latter.

The dose of a compound according to the present invention for the treatment of the diseases or disorders mentioned above, varies according to the administration method, the age and body weight of the patient as well as the state of the latter and it will be decided definitively by the attending doctor or vet. Such a quantity determined by the attending doctor or vet is called here "effective therapeutic quantity".

A preparation method of the compound of formula (I) or of formula (II) and the new chemical intermediates used in these syntheses as described here are also considered as part of the invention.

Other characteristics and advantages of the present invention will be apparent from the detailed description of the invention and from the claims.

It is considered that a person skilled in the art can, based on the description given here, use the present invention to its widest extent. The following specific embodiments are mentioned simply as illustrations, and do not limit the scope of the disclosure in any way whatsoever.

Unless defined in another manner, all the technical and scientific terms used here have the same meaning as that commonly understood by an ordinary specialist in the field to which the invention belongs. Similarly, all publications, patent applications, all patents and all other references mentioned here are incorporated by way of reference.

Synthesis

As represented in Diagram I, the compounds of the invention can generally be prepared by condensation of the derivatives of 3-amino-1-propanol of general formula (II) (Kim, J. K. et al., J. Org. Chem. 54:1714 (1989) and Koepke, S. R. and al., J. Org. Chem. 44:2718 (1979)) with the appropriate acid derivatives of general formula (III).

Diagram I

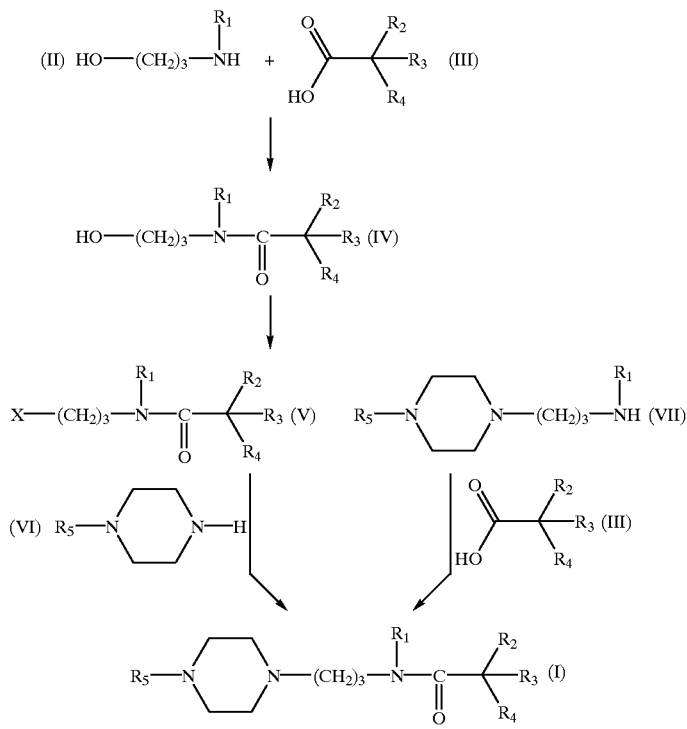

In Diagram I, $R_1$–$R_5$ are defined as above and X represents an eliminable group, for example, methane-sulphonyloxy, p-toluene-sulphonyloxy, chlorine, bromine or iodine. The derivatives of benzylic acid (III), in which $R_3$ and $R_4$ represent aromatics and $R_2$ represents OH, are obtained either by heating to 80° C. the benzyl derivatives benzyls and an alkali metal hydroxide (for example, KOH) in the solid state (Toda, F. et al., Chem. Letts. pp. 373–376, The Chemistry Society of Japan (1990)), as illustrated by Example 25, or by heating to 95° C. in aqueous organic solvents (Rzeszotarski, W. J. and al., J. Med. Chem. 27:156 (1984)).

The acid derivatives (III), in which $R_3$ represents an alkyl chain, $R_4$ represents an aromatic, and $R_2$ represents OH, can be obtained by other methods. One method involves the reaction of acetophenone derivatives with trimethylsilyl-cyanide in the presence of a catalytic quantity of $ZnI_2$ at ambient temperature in order to obtain cyanohydrines after acid hydrolysis (Gassman, P. G. et al., Tetrahedron Lett. 40:3773 (1978)). These cyanohydrines are then converted into α-hydroxy acids by refluxing them in concentrated HCl (Org. Synth. Coll. Vol. 1:289 (1941)). Another method involves the alkylation of the trianions of α-hydroxycarboxylic acids at −78° C. with alkyl chlorides (Newcomb M., et al., J. Org. Chem. 43:3963 (1978)) which also leads to the desired alkylated acids as illustrated by Example 28. Yet another method is the synthesis of α-aryl-alkanoic esters from α-ketoesters, for example ethyl-pyruvate, and aryl nucleophilics such as the bromides of aryl magnesium (Salomon, R. G. et al., J. Org. Chem. 47:4692 (1982)). The derivatives of aryl magnesium are practically prepared by refluxing aryl bromide and magnesium powder in THF or dry or anhydrous diethyl-ether ("dry"). The condensation stage takes place by passing through cannulas ("cannulating") the cold derivative of aryl magnesium on the α-ketoester cooled down beforehand (−78° C.) as illustrated by Example 40. The saponification is easily carried out by agitating these esters in the presence of KOH in methanol for several hours. The chiral alkanoic α-aryl-α-hydroxy esters are mainly accessible via the addition of organometallic reagents on the chiral α-ketoesters (Basavaiah, δ. and Bharathi, T. K., Tetrahedron Lett. 32:3417 (1991)) using, for example, trans-2-phenylcyclohexanol as the auxiliary chiral.

The acid derivatives (III) in which $R_3$ represents a hydrogen or an alkyl chain, $R_4$ represents an aromatic, and $R_2$ represents an aminocarbonyl are practically prepared from phenylmalonic diesters. The optional alkylation stage takes place, under anhydrous conditions, in the presence of a strong base such as NaH and an alkylation agent $R_6$—X, as defined above, in a dry polar solvent, for example DMF or THF. Saponification with an equivalent of ethanolic KOH at ambient temperature allows access to mono-acid derivatives which are easily converted into carboxamide derivatives by reaction with an amine $NR_6R_7$, as defined above, under standard peptide conditions. This condensation stage takes place in the presence of dicyclohexylcarbodiimide and hydroxybenzotriazole as coupling reagents in an inert solvent preferably dichloromethane or DMF (Bodanszky, M. and Bodanszky, A., The Practice of Peptide Synthesis, 145 (Springer-Verlag, 1984)). Alternatively, these carboxamide derivatives are accessible by direct condensation of an amine $NR_6R_7$, as described above, with phenylmalonic diesters by heating them in a mixture of solvents such as THF/Toluene in the presence of sodium diethyldihydroaluminate (Sim, T. B. and Yoon, N. M., Synlett 827 (1994)). Deprotection of the second acid function is carried out exactly as described previously.

The peptide coupling reaction of the compounds of general formulae (II) and (III) is well known in the prior art (Bodanszky, M. and Bodanszky, A., The Practice of Peptide Synthesis, 145 (Springer-Verlag, 1984)). The primary hydroxyl group of the compounds of general formula (IV) can be easily converted into an eliminable group, for example a sulphonyloxy group, by reaction with a methane-sulphonyl chloride in the presence of triethylamine in dichloromethane or of p-toluenesulphonyl chloride in pyridine. When $R_2$ represents OH, the selective activation of the primary alcohol will be carried out only thanks to halogenation type reactions, for example with the iodides of general formula (V), in which X represents I, which are practically prepared by reaction with iodine, triphenylphosphine, and imidazole (Garegg, P. J. et al., J. Chem. Soc. Perkin 1, 681 (1982)) as illustrated by the intermediate synthesized in Exemple 1.2. The condensation reaction of a compound of general formula (V) with a compound of general formula (VI) (see Diagram I) can be carried out by heating the mixture to 80° C. in a polar solvent, for example acetonitrile, for several hours.

Alternatively, the compounds of general formula (I) can be prepared by standard peptide condensation of a primary amine derivative of general formula (VII) (for a practical preparation see Wu, Y. H. et al., J. Med. Chem. 12:876 (1969)) with an acid derivative of general formula (III).

As is represented in the Diagram II, the compounds of general formula (VI), for example formulae (VIa), (VIb) and (VIc), with a lower alkyl, a hydroxyalkyl, or an alkoxyalkyl as substituents, can generally be prepared.

Diagram II

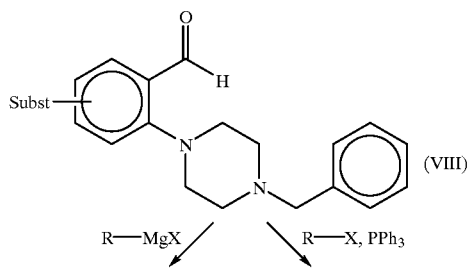

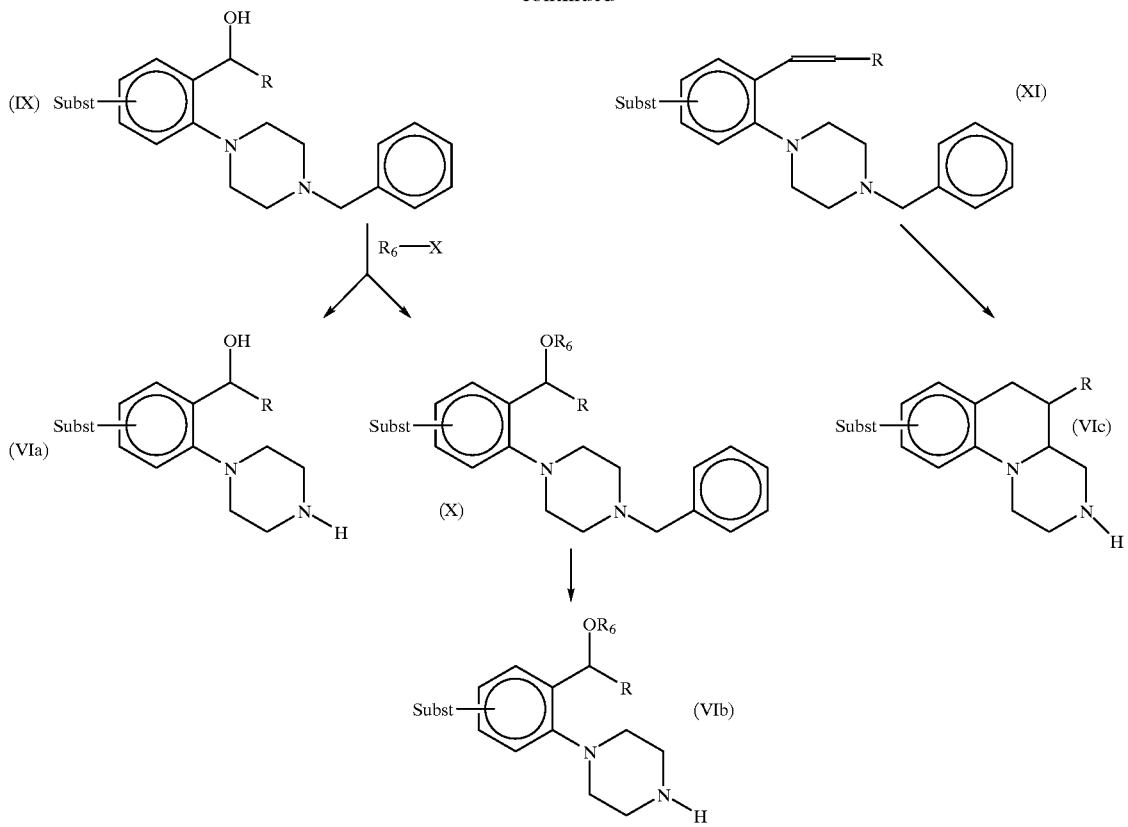

In Diagram II, $R_6$ as defined above, represents an alkyl group, Subst represents a substituent as defined in $R_5$, and X represents an eliminable group, for example methanesulphonyloxy, p-toluenesulphonyloxy, chlorine, bromine or iodine. The condensation between the benzaldehyde derivatives of general formula (VIII) (Walter, H. N. et al., Synthesis, pp. 641–645 (1987)) and the alkyl Grignard reagents in diethylether or THF allow the corresponding secondary alcohol of general formula (IX) to be obtained, as illustrated by intermediate 36.2. The compounds of general formula (VIa) are obtained by deprotection of the compounds of general formula (IX) according to known general debenzylation methods, for example catalytic hydrogenation or reaction with a chloroformate, such as vinyl chloroformate or α-chloroethyl chloroformate, followed by hydrolysis or methanolysis. Other debenzylation methods such as those found in Green, T. W. and Wuts, P. G. M., Protective Groups in Organic Synthesis, 2d ed., 364, (John Wiley & Sons Inc., 1991) can also be used on the condition that they are compatible with the substituents of the aryl cycle of the compound of general formula (IX). The compounds of general formula (IX) can be O-alkylated under anhydrous conditions at ambient temperature in the presence of a strong base, for example NaH, and an alkylation agent $R_6$—X, as defined above, in a dry polar solvent, for example DMF or THF. Debenzylation of the compounds of general formula (X) following the procedure already described allows the compounds of general formula (VIb)) to be obtained.

Alternatively, the compounds of general formula (VIII) can be converted into a compound of general formula (XI) via a reaction of Wittig type reaction involving an alkylphosphorane reagent generated from an alkylphosphonium salt and a strong base, for example nBuLi or phenyllithium, in THF or dry diethylther. The compounds of general formula (VIc) are obtained via a reduction of the double bond and concomitant debenzylation under catalytic hydrogenation conditions.

The compounds of general formula (I), in which $R_2$ represents OH, can be O-alkylated under anhydrous conditions in the presence of a strong base such as NaH and an alkylation agent $R_6$—X in a dry polar solvent, for example DMF or THF. The compounds of general formula (I), in which $R_2$ represents a modified amine (for example a sulphonyl amide or a carboxamide), are synthesized by reaction of a chlorosulphonyl or a halogenated acid derivative on a free amino-acid under similar conditions to those of the Schotten-Baumann procedure (Bodanszy, M. and Bodanszky, A., The Practice of Peptide Synthesis, 9 (Springer-Verlag, 1984)).

What follows describes the specific chemical synthesis of compounds 1 à 56. Other compounds according to the invention can be prepared in a similar manner by an average person skilled in the art.

EXAMPLE 1

α-hydroxy-N-[3-{4-(3-methylphenyl)-1-piperazinyl}-propyl]-α-phenylbenzeneacetamide, dihydrochloride (Compound 1)

1.1) α-hydroxy-N-(3-hydroxypropyl)-α-phenyl-benzeneacetamide:

11.34 g (55 mmol) of dicyclohexylcarbodiimide is added in one go to a cold solution (0–5° C.) of 3.82 ml (50 mmol) of 3-amino-1-propanol, 7.43 g (55 mmol) of hydroxybenzotriazole and 11.4 g (50 mmol) of benzylic acid in 60 ml of DMF. The solution is left to heat up to ambient temperature and is agitated for 15 hours. Filtration of the precipitated dicyclohexylurea followed by evaporation of the mother liquor allows an oily residue to be obtained which is dissolved in 150 ml of ethyl acetate. This solution is rinsed successively with water 2×100 ml), 1N NaOH (2×100 ml) and a saturated solution of NaCl (100 ml). The organic phase is dried over sodium sulphate and the solvent is evaporated off under reduced pressure in order to produce 12.8 g (89%) of compound mentioned in the title in the form of a white solid; M.p.: 126–127° C.

NMR-$^1$H (100 MHz, CDCl, δ): 7,40 (m, 10H, 2×Ph); 6.95 (m, 1H, CO—NH); 3.98 (s, 1H, OH); 3.45 (m, 4H, C$\underline{H_2}$—NH, C$\underline{H_2}$—OH); 2.88 (m, 1H, CH$_2$—$\underline{OH}$) 163 (m, 2$\underline{H}$, CH$_2$).

1.2) α-hydroxy-N-(3-iodopropyl)-α-phenyl-benzeneacetamide:

14.26 g (56 mmol) of iodine are added in several lots to a cold solution (0–5° C.) of 14.7 g (56 mmol) of triphenylphosphine and 3.82 g (56 mmol) of imidazole in a mixture of 90 ml of diethylether and 30 ml of acetonitrile. A yellow precipitate forms rapidly during agitation at ambient temperature for one hour. A solution of 8 g (28 mmol) of α-hydroxy-N-(3-hydroxypropyl)-α-phenyl-benzeneacetamide in 90 ml of diethylether and 30 ml of acetonitrile is added dropwise to this yellow suspension and agitation is continued for 15 hours. The resultant mixture is filtered and concentrated so as to obtained a brown oily residue which its purified by flash chromatography (eluant: light oil (bp. 40–65° C.)/ethyl acetate: 8/2 then 6/4). Evaporation of the appropriate phases under reduced pressure allows 8.86 g (80%) of compound mentioned in the title to be obtained in the form of a light yellow solid; M.p.: 105–106° C.

NMR-$^1$H (100 MHz, CDCl$_3$, δ): 7.35 (m, 10H, 2×Ph); 6.57 (m, 1H, CO—NH); 3.81 (s, 1H, OH); 3.40 (m, 2H, C$\underline{H_2}$—NH); 3.09 (t, 2H, CH$_2$—I) 2.00 (m, 2H, CH$_2$).

1.3) α-hydroxy-N-[3-{4-(3-methylphenyl)-1-piperazinyl}-propyl]-α-phenyl-benzeneacetamide, dihydrochloride:

A mixture of 0.6 g (3.4 mmol) of 1-(3-methylphenyl)-piperazine and 1.34 g (3.4 mmol) of α-hydroxy-N-(3iodopropyl)-α-phenyl-benzeneacetamide in 20 ml of acetonitrile is heated to reflux for 3 hours. After cooling down to ambient temperature, the reaction mixture is concentrated under reduced pressure. The oily residue is dissolved in 50 ml of ethyl acetate and rinsed with 1N NaOH (2×50 ml) and of water (2×50 ml). After usual treatment, the crude product is purified by flash chromatography (eluant: ethyl acetate). Evaporation of the solvent under reduced pressure produces 0.78 g (52%) of the base of Compound 1 which is converted into its hydrochloride salt by an ethereal solution of hydrogen chloride; M.p.: 195–196° C.

NMR-$^1$H (400 Mz, DMSO d6, δ): 11.04 (bs, 1H, $^+$NH); 8.42 (t, 1H, NH—CO); 7.35 (m, 10H, 2×Ph); 7.14 (m, 1H, Ph—CH$_3$); 6.80 (m, 2H, Ph—CH$_3$); 6.70 (m, 1H, Ph—CH$_3$); 6.34 (bs, 1H, OH); 3.75 (δ, 2H, $^+$NH—C$\underline{H_2}$); 3.45 (δ, 2H, CH$_2$—NH—CO); 3.10 (m, 8H, pipera$\overline{zine}$); 2.27 (s, 3H, C$\overline{H_3}$); 1.91 (m, 2H, CH$_2$).

Elemental analysis for C$_{28}$H$_{33}$N$_3$O$_2$, 2 HCl: % Calc: C, 65.11; H, 6.83; N, 8.14; % obtained: C, 65.02; H, 6.80; N, 8.10.

EXAMPLE 2

α-hydroxy-N-[3-{4-(2-methylphenyl)-1-piperazinyl}-propyl]-α-phenyl-benzeneacetamide, dihydrochloride, 0.5 H$_2$O (Compound 2)

Compound 2 is prepared in a similar manner to that of Example 1, except that 1-(2-methylphenyl)-piperazine is used in place of 1-(3-methylphenyl)-piperazine.

NMR-$^1$H (400 MHz, DMSO d6, δ): 10.97 (bs, 1H, $^+$NH); 8.43 (t, 1H, NH—CO); 7.34 (m, 10H, 2×Ph); 7.18 (m, 2H, Ph—CH$_3$); 7.00 (m, 2H, Ph—CH$_3$); 4.49 (bs, 1H, OH); 3.44 (δ, 2H, $^+$NH—C$\underline{H_2}$); 3.23 (m, 2H, C$\underline{H_2}$—NHCO) 3.09 (m, 8H, piperazine); 2.26 (s, 3H, CH$_3$); 1.94 (m, 2H, CH$_2$).

Elemental analysis for C$_{28}$H$_{33}$N$_3$O$_2$, 2 HCl, 0.5 H$_2$O: % Calc: C, 64.00; H, 6.90; N, 8.00; % obtained: C, 63.896 H, 6.87; N, 7.92; M.p.: 191–192° C.

EXAMPLE 3

α-hydroxy-N-[3-{4-(4-methylphenyl)-1-piperazinyl}-propyl]-α-phenyl-benzeneacetamide, dihydrochloride (Compound 3)

Compound 3 is prepared in a similar manner to that of Example 1, except that 1-(4-methylphenyl)-piperazine is used in place of 1-(3-methylphenyl)-piperazine; M.p.: 204.5° C.

NMR-$^1$H (400 MHz, DMSO d6, δ): 11,.0 (bs, 1H, $^+$NH); 8.42 (t, 1H, NH—CO); 7.33 (m, 10H, 2×Ph); 7.00 (m, 4H, Ph—CH$_3$); 6.78 (bs, 1H, OH); 3.68 (δ, 2H, $^+$NH—C$\underline{H_2}$); 3.45 (δ, 2H, CH$_2$—NH—CO); 3.15 (m, 8H, piperazine); 2.22 (s, 3H, C$\overline{H_3}$); 1.93 (m, 2H, CH$_2$).

Elemental analysis for C$_{28}$H$_{33}$N$_3$O$_2$, 2 HCl: % Calc: C, 65.11; H, 6.83; N, 8.14; % obtained: C, 64.91 H, 6.89; N, 8.11.

EXAMPLE 4

N-[3-{4-(2,3-dimethylphenyl)-1-piperazinyl}-propyl]-α-hydroxy-α-phenyl-benzeneacetamide, hydrochloride, 0.25 H$_2$O (Compound 4)

Compound 4 is prepared in a similar manner to that of Example 1, except that 1-(2,3-dimethylphenyl)-piperazine is used in place of 1-(3-methylphenyl)-piperazine; M.p.: 125–126° C.

NMR-$^1$H (400 MHz, DMSO d6, δ): 11.05 (bs, 1H, $^+$NH); 8.43 (t, 1H, NH—CO); 7.39 (m, 10H, 2×Ph); 7.07 (m, 1H, Ph—CH$_3$); 6.93 (m, 1H, Ph—CH$_3$); 6.89 (m, 1H, Ph—CH$_3$); 4.34 (bs, 1H, OH); 3.43 (δ, 2H, $^+$NH—C$\underline{H_2}$); 3.23 (m, 2H, CH$_2$—NH—CO); 3.06 (m, 8H, pipera$\overline{zine}$); 2.22 (s, 3H, C$\overline{H_3}$); 2.17 (s, 3H, CH$_3$); 1.95 (m, 2H, CH$_2$).

Elemental analysis for C$_{29}$H$_{35}$N$_3$O$_2$, HCl, 0.25 H$_2$O: % Calc: C, 69.86; H, 7.38; N, 8.43; O, 7.22; % obtained: C, 69.93; H, 7.63; N, 8.53; O, 7.41.

EXAMPLE 5

N-[3-{4-(2,4-dimethylphenyl)-1-piperazinyl}-propyl]-α-hydroxy-α-phenyl-benzeneacetamide, fumarate, monohydrate (Compound 5)

Compound 5 is prepared in a similar manner to that of Example 1, except that 1-(2,4-dimethylphenyl)-piperazine is used in place of 1-(3-methylphenyl)-piperazine; M.p.: 177° C.

NMR-$^1$H (400 MHz, DMSO d6, δ): 8.35 (t, 1H, NH—CO); 7.35 (m, 10H, 2×Ph); 6.93 (m, 3H, Ph—CH$_3$); 6.75 (bs, OH, COOH); 6.62 (s, 2H, CH═CH); 3.39 (m, 2H, CH$_2$—NH—CO); 2.87 (bs, 4H, piperazine); 2.71 (bs, 4H, piperazine); 2.56 (m, 2H, N—C$\underline{H_2}$); 2.20 (s, 6H, 2×CH$_3$); 1.71 (m, 2H, CH$_2$).

Elemental analysis for C$_{29}$H$_{35}$N$_3$O$_2$, fumarate, monohydrate: % Calc: C, 66.99; H, 6.98; N, 7.10; O, 18.93; % obtained: C, 67.21; H, 6.72; N, 6.87; O, 18.80.

EXAMPLE 6

N-[3-{4-(2,6-dimethylphenyl)-1-piperazinyl}-propyl]-a-hydroxy-a-phenyl-benzeneacetamide, hydrochloride, 0.5 H$_2$O (Compound 6)

Compound 6 is prepared in a similar manner to that of Example 1, except that 1-(2.6-dimethylphenyl)-piperazine is used in place of 1-(3-methylphenyl)-piperazine; M.p.: 183–184° C.

NMR-$^1$H (400 MHz, DMSO d6, δ): 10.69 (bs, 1H, $^+$NH); 8.44 (t, 1H, NH—CO); 7.35 (m, 10H, 2×Ph); 7.04 (m, 1H, Ph—CH$_3$); 6.97 (m, 2H, Ph—CH$_3$); 3.65 (t, 2H, $^+$NH—CH$_2$) 3.34 (bs, 1H, OH); 3.71–2.93 (m, 8H, piperazine); 3.22 (m, 2H, CH$_2$—NHCO); 2.29 (s, 3H, CH$_3$); 2.27 (s, 3H, CH$_3$); 1.93 (m, 2H, CH$_2$).

Elemental analysis for C$_{29}$H$_{35}$N$_3$O$_2$, HCl, 0.5 H$_2$O: % Calc: C, 69.24; H, 7.41; N, 8.35; O, 7.95; % obtained: C, 69.59; H, 7.72; N, 8.42; O, 7.65.

EXAMPLE 7

N-[3-{4-(2.5-dimethylphenyl)-1-piperazinyl}-propyl]-α-hydroxy-α-phenyl-benzeneacetamide, 1.5 HCl, 0.25 H$_2$O (Compound 7)

Compound 7 is prepared in a similar manner to that of Example 1, except that 1-(2.5-dimethylphenyl)-piperazine is used in place of t 1-(3-methylphenyl)-piperazine; M.p.: 171–172° C. NMR-$^1$H (400 MHz, DMSO d6, δ): 11.01 (bs, 1H, $^+$NH); 8.43 (t, 1H, NH—CO); 7.34 (m, 10H, 2×Ph); 7.06 (δ, 1H, Ph—CH$_3$, J=7.5 Hz); 6.82 (δ, 2H, Ph—CH$_3$); 6.90 (bs, 1H, OH); 3.43 (m, 2H, $^+$NH—CH$_2$); 3.22 (m, 2H, CH$_2$—NHCO); 3.10 (m, 8H, piperazine); 2.26 (s, 3H, CH$_3$); 2.20 (s, 3H, CH$_3$); 1.93 (m, 2H, CH$_2$).

Elemental analysis for C$_{30}$H$_{37}$N$_3$O$_2$, 1.5 HCl, 0.25 H$_2$O: % Calc: C, 67.40; H, 7.22; N, 8.13, O, 6.97; % obtained: C, 67.10; H, 7.17; N, 8.22; O, 7.25.

EXAMPLE 8

N-[3-{4-(2-ethoxyphenyl)-1-piperazinyl}-propyl]-α-hydroxy-α-phenyl-benzeneacetamide, 2 HCl, 0.25 H$_2$O (Compound 8)

Compound 8 is prepared in a similar manner to that of Example 1, except that 1-(2-ethoxyphenyl)-piperazine is used in place of 1-(3-methylphenyl)-piperazine; M.p.: 189° C.

NMR-$^1$H (400 MHz, DMSO d6, δ): 11.01 (bs, 1H, $^+$NH); 8.43 (t, 1H, NH—CO); 7.34 (m, 10H, 2×Ph); 6.96 (m, 4H, Ph—N); 5.36 (bs, 1H, OH); 4.04 (q, 2H, OCH$_2$, J=6.95 Hz); 3.48 (m, 4H, $^+$NH—CH$_2$+piperazine); 3.22 (m, 2H, CH$_2$—NHCO); 3.05 (m, 6H, piperazine); 1.93 (m, 2H, CH$_2$); 1.37 (t, 3H, CH$_3$).

Elemental analysis for C$_{29}$H$_{35}$N$_3$O$_3$, 2 HCl, 0.25 H$_2$O: % Calc: C, 63.21; H, 6.86; N, 7.63; O, 9.44; % obtained: C, 63.16; H, 6.85; N, 7.60; O, 9.64.

EXAMPLE 9

N-[3-{4-(2-chlorophenyl)-1-piperazinyl}-propyl]-α-hydroxy-α-phenyl-benzeneacetamide, fumarate (Compound 9)

Compound 9 is prepared in a similar manner to that of Example 1, except that 1-(2-chlorophenyl))-piperazine is used in place of 1-(3-methylphenyl)-piperazine; M.p.: 190° C.

NMR-$^1$H (400 MHz, DMSO d6, δ): 8.38 (t, 1H, NH—CO); 7.34 (m, 12H, 2×Ph+Ph—Cl); 7.16 (m, 1H, Ph—Cl); 7.03 (m, 1H, Ph—Cl); 6.68 (bs, 1H, OH); 6.61 (s, 2H, CH=CH); 3.20 (m, 2H, CH$_2$—NHCO); 3.00 (bs, 4H, piperazine); 2.58 (bs, 4H, piperazine); 2.43 (m, 2H, CH$_2$—N); 1.66 (m, 2H, CH$_2$).

Elemental analysis for C$_{27}$H$_{30}$ClN$_3$O$_2$, fumarate: % Calc: C, 64.19; H, 5.91; N, 7.24; % obtained: C, 64.13; H, 5.90; N, 7.27.

EXAMPLE 10

N-[3-{4-(2-cyanophenyl)-1-piperazinyl}-propyl]-α-hydroxy-α-phenyl-benzeneacetamide, hydrochloride, monohydrate (Compound 10)

Compound 10 is prepared in a similar manner to that of Example 1, except that 1-(2-cyanophenyl)-piperazine is used in place of 1-(3-methylphenyl)-piperazine; M.p.: 168° C. NMR-$^1$H (400 MHz, DMSO d6, δ): 10.91 (bs, 1H, $^+$NH); 8.43 (t, 1H, NH—CO); 7.78 (m, 1H, Ph—CN); 7.66 (m, 1H, Ph—CN); 7.34 (m, 12H, 2×Ph+Ph—Cn); 3.57 (m, 4H, $^+$NH—CH$_2$+piperazine); 3.35 (m, OH+piperazine); 3.18 (m, 2H, CH$_2$—NHCO); 3.10 (m, 4H, piperazine); 1.93 (m, 2H, CH$_2$).

Elemental analysis for C$_{28}$H$_{30}$N$_4$O$_2$, HCl, H$_2$O: % Calc: C, 66.07; H, 6.53; N, 11.01; % obtained: C, 65.91; H, 6.50; N, 11.01.

EXAMPLE 11

N-[3-{4-(2,5-dimethylphenyl)-1-piperazinyl}-propyl]-α-methoxy-α-phenyl-benzeneacetamide, hydrochloride, monohydrate (Compound 11)

0.51 g (1 mmol) of N-[3-{4-(2.5-dimethylphenyl)-1-piperazinyl}-propyl]-α-hydroxy-α-phenyl-benzeneacetamide (Example 7) is introduced in an anhydrous three-necked flask equipped with a nitrogen supply and "septa" type stoppers. Dry DMF (10 ml) is added and the solution is cooled down à 0–5° C. using an ice bath. Sodium hydride (0.08 g, 2 mmol) is then added in one go and the mixture is left to heat up to ambient temperature. After one hour, 0.06 ml (1 mmol) of methyl iodide is introduced dropwise into the flask using a syringe. After mixing for another two hours, the mixture is concentrated and the residue is dissolved in 25 ml of ethyl acetate. This solution is rinsed successively with water (2×20 ml) and a saturated solution of NaCl (20 ml). The organic phase is dried over sodium sulphate and evaporated under reduced pressure so as to obtained an oil which is purified by flash chromatography (eluant: dichloromethane/methanol: 95/5). Evaporation the collected phases under reduced pressure produces 0.18 g (38%) of the base of Compound 11. This is converted into its hydrochloride salt as described above; M.p.: 125–126° C.

NMR-$^1$H (400 MHz, DMSO d6, δ): 10.82 (bs, 1H, $^+$NH); 8.57 (t, 1H, NH—CO); 7.36 (m, 10H, 2×Ph); 7.07 (δ, 1H, Ph—CH$_3$); 6.82 (m, 2H, Ph—CH$_3$); 3.38 (m, 2H, $^+$NH—CH$_2$); 3.21 (m, 2H, CH$_2$—NHCO); 3.17–2.80 (m, 8H, piperazine); 2.98 (s, 3H, OCH$_3$); 2.26 (s, 3H, CH$_3$); 2.21 (s, 3H, CH$_3$); 1.90 (m, 2H, CH$_2$).

Elemental analysis for C$_{30}$H$_{37}$N$_3$O$_2$, HCl, H$_2$O: % Calc: C, 68.49; H, 7.66; N, 7.99; % obtained: C, 68.24; H, 7.52; N, 7.99.

EXAMPLE 12

α-benzyloxy-N-[3-{4-(2,5-dimethylphenyl)-1-piperazinyl}-propyl]-α-phenyl-benzeneacetamide (Compound 12)

Compound 12 is prepared in a similar manner to that of Example 11 except that benzyl bromide is used in place of methyl iodide in the O-alkylation stage; M.p.: 171° C. NMR-$^1$H (400 MHz, DMSO d6, δ): 8.53 (m, 1H, NH—CO); 7.32 (m, 10H, 2×Ph); 7.07 (δ, 1H, Ph—CH$_3$, J=7.5 Hz); 6.82 (δ, 2H, Ph—CH$_3$); 3.54 (m, 2H, CH$_2$—NHCO); 3.28–3.10 (m, 8H, piperazine); 2.27 (s, 3H, CH$_3$); 2.18 (s, 3H, CH$_3$); 2.10 (m, 2H, CH$_2$).

EXAMPLE 13

N-[3-{4-(2-methoxyphenyl)-1-piperazinyl}-propyl]-α-phenyl-benzeneacetamide, dihydrochloride (Compound 13)

0.424 g (2 mmol) of diphenylacetic acid, 0.498 g (2 mmol) of 3-[4-(2-methoxyphenyl)-1-piperazinyl]-propyl-1-amine (Wu, Y. H. et al. J. Med. Chem. 12:876 (1969)) and 0.297 g 2.2 mmol) of hydroxybenzotriazole are dissolved in 15 ml of THF. The solution is cooled down to 0–5° C. before the addition of 0.453 g (2.2 mmol) of dicyclohexylcarbodiimide. Agitation is continued at ambient temperature for 15 hours. The resultant mixture is filtered, the insoluble matter is rinsed with the minimum amount of THF and the filtrate is evaporated under reduced pressure. The oily residue is dissolved in 50 ml of ethyl acetate and rinsed successively with $H_2O$ (2×25 ml), NaOH 0.1 N (25 ml) and a saturated solution of sodium chloride. The organic phase is dried over sodium sulphate and evaporated to dryness. The residue is subjected to flash chromatography on silica gel (eluant: dichloromethane/methanol: 95/5). Evaporation of the collected phases under reduced pressure produces 0.505 g (55%) of the compound mentioned in the title which is in the form of a salt by using an anhydrous solution of hydrogen chloride in diethylether; M.p.: 198–199° C.

NMR-$^1$H (100 MHz, CDCl$_3$, δ [free base]): 7.30 (m, 11H, 2×Ph+NH—CO); 6.90 (m, 4H, Ph—OCH$_3$); 4.88 (s, 1H, CH); 3.90 (s, 3H, OCH$_3$); 3.40 (m, 2H, CH$_2$—NH—CO); 3.15–2.50 (m, 8H, piperazine); 2.50 (m, 2H, NH—CH$_2$); 1.70 (m, 2H, CH$_2$).

Elemental analysis for $C_{28}H_{33}N_3O_2$, 2 HCl: % Calc: C, 65.11; H, 6.83; N, 8.14; % obtained: C, 64.82; H, 6.90; N, 8.01.

EXAMPLE 14

α-hydroxy-N-[3-{4-(2-methoxyphenyl)-1-piperazinyl}-propyl]-α-phenyl-benzeneacetamide, dihydrochloride, 0.25 $H_2O$ (Compound 14)

Compound 14 is prepared in a similar manner to that of Example 13 except that benzylic acid is used in place of diphenylacetic acid; M.p.: 191–192° C.

NMR-$^1$H (400 MHz, DMSO d6, δ): 10.93 (bs, 1H, $^+$NH); 8.43 (t, 1H, NH—CO); 7.36 (m, 10H, 2×Ph); 6.95 (m, 4H, Ph—OCH$_3$); 4.85 (bs, 1H, OH); 3.80 (s, 3H, OCH$_3$); 3.45 (m, 2H, $^+$NH—CH$_2$); 3.21 (m, 2H, CH$_2$—NHCO) 3.40–2.95 (m, 8H, piperazine); 1.92 (m, 2H, CH$_2$).

Elemental analysis for $C_{28}H_{33}N_3O_3$, 2 HCl, 0.25 $H_2O$: % Calc: C, 62.63; H, 6.66; N, 7.82; O, 9.68; % obtained: C, 62.59; H, 6.88; N, 7.93; O, 9.59.

EXAMPLE 15

N-[3-{4-(2-methoxyphenyl)-1-piperazinyl}-propyl]-9H-xanthene-9-carboxamide, dihydrochloride (Compound 15)

Compound 15 is prepared in a similar manner to that of Example 13 except that 9H-xanthene-9-carboxylic acid is used in place of diphenylacetic acid; M.p.: 257–258° C.

NMR-$^1$H (100 MHz, CDCl$_3$, δ [free base]): 7.50–6.80 (m, 12H, xanthene+Ph—OCH$_3$), 6.27 (m, 1H NH—CO); 4.92 (s, 1H, CH); 3.85 (s, 3H, OCH$_3$); 3.25 (m, 2H, CH$_2$—NH—CO), 3.00–2.30 (m, 8H, piperazine); 2.25 (m, 2H, NH—CH$_2$); 1.60 (m, 2H, CH$_2$).

Elemental analysis for $C_{28}H_{31}N_3O_3$, 2 HCl: % Calc: C, 63.40; H, 6.27; N, 7.92; % obtained: C, 63.22; H, 6.30; N, 7.74.

EXAMPLE 16

9-hydroxy-N-[3-{4-(2-methoxyphenyl)-1-piperazinyl}-propyl]-9H-fluorene-9-carboxamide, dihydrochloride, monohydrate (Compound 16)

Compound 16 is prepared in a similar manner to that of Example 13 except that 9-hydroxy-9-fluorene carboxylic acid is used in place of diphenylacetic acid M.p.: 186–187° C.

NMR-$^1$H (100 MHz, CDCl$_3$, δ [free base]): 7.70–7.25 (m, 8H, fluorene); 6.97 (m, 4H, Ph—OCH$_3$); 6.30 (m, 1H, NH—CO); 3.85 (s, 3H, OCH$_3$); 3.30 (m, 2H, CH$_2$—NH—CO); 2.90–2.30 (m, 8H, piperazine); 2.20 (m, 2H, NH—CH$_2$); 1.65 (m, 3H, OH+CH$_2$).

Elemental analysis for $C_{28}H_{31}N_3O_3$, 2 HCl, $H_2O$: % Calc: C, 61.31; H, 6.43; N, 7.66; % obtained: C, 61.32; H, 6.25; N, 7.64.

EXAMPLE 17

2-chloro-α-(2-chlorophenyl)-α-hydroxy-N-[3-{4-(2-methoxyphenyl)-1-piperazinyl}-propyl]-α-phenyl-benzeneacetamide, monohydrochloride, monohydrate (Compound 17)

Compound 17 is prepared in a similar manner to that of Example 13 except that 2,2'-dichlorobenzylic acid is used in place of diphenylacetic acid; M.p.: 185–186° C.

NMR-$^1$H (100 MHz, CDCl$_3$, δ [free base]): 7.75 (m, 1H, NH—CO); 7.30 (m, 8H, 2×Ph—Cl); 6.90 (m, 4H, Ph—OCH$_3$); 3.88 (s, 3H, OCH$_3$); 3.52 (m, 2H, CH$_2$—NH—CO); 3.10–2.40 (m, 8H, piperazine); 2.50 (m, 2H, NH—CH$_2$); 1.80 (m, 2H, CH$_2$).

Elemental analysis for $C_{28}H_{31}Cl_2N_3O_3$, HCl, $H_2O$: % Calc: C, 57.69; H, 5.88; N, 7.21; % obtained: C, 57.42; H, 5.84; N, 6.67.

EXAMPLE 18

(±)-α-cyclohexyl-N-[3-{4-(2-methoxyphenyl)-1-piperazinyl}-propyl]-benzeneacetamide, dihydrochloride, monohydrate (Compound 18)

Compound 18 is prepared in a similar manner to that of Example 13 except that (±) -cyclohexylphenyl acetic acid is used in place of diphenylacetic acid; M.p.: 160–161° C.

NMR-$^1$H (400 MHz, DMSO d6, δ): 10.94 (bs, 1H, $^+$NH); 8.32 (m, 1H, NH—CO) , 7.28 (m, 5H, Ph); 6.95 (m, 4H, Ph—OCH$_3$); 3.80 (s, 3H, OCH$_3$); 3.42 (m, 2H, $^+$NH—CH$_2$); 3.42–2.90 (m, 8H, piperazine); 3.05 (m, 2H, CH$_2$—NH—CO); 2.00–0.68 (m, 13H, cyclohexyl+CH$_2$).

Elemental analysis for $C_{28}H_{39}N_3O_2$, 2 HCl, $H_2O$: % Calc: C, 62.21; H, 7.83; N, 7.77; % obtained: C, 62.09; H, 7.89; N, 7.60.

EXAMPLE 19

(±)-α-hydroxy-N-[3-{4-(2-methoxyphenyl)-1-piperazinyl}-propyl]-benzeneacetamide, dihydrochloride, monohydrate (Compound 19)

Compound 19 is prepared in a similar manner to that of Example 13 except that (±)-mandelic acid is used in place of diphenylacetic acid; M.p.: 169° C.

NMR-$^1$H (400 MHz, DMSO d6, δ): 10.94 (bs, 1H, $^+$NH); 8.27 (m, 1H, NH—CO); 7.35 (m, 5H, Ph); 6.95 (m, 4H, Ph—OCH$_3$); 5.70 (bs, OH); 4.95 (s, 1H, CH); 3.80 (s, 3H,

OCH$_3$); 3.42 (m, 2H, $^+$NH—CH$_2$); 3.25–3.02 (m, 10H, piperazine+CH$_2$—NH—CO); 1.90 (m, 2H, CH$_2$).

Elemental analysis for C$_{22}$H$_{29}$N$_3$O$_3$, 2 HCl, H$_2$O: % Calc: C, 55.70; H, 7.01; N, 8.86; % obtained: C, 55.23; H, 6.90; N, 8.84.

EXAMPLE 20

N-[3-{4-(2,5-dimethylphenyl)-1-piperazinyl}-propyl]-α-phenyl-benzeneacetamide, 1.5 HCl, H$_2$O (Compound 20)

20.1) 3-[4-(2,5-dimethylphenyl)-1-piperazinyl]-propyl-1-amine

This intermediate is synthesized using the same procedure as that described by Wu, Y. H. et al. J. Med. Chem. 12:876 (1969); M.p.: 102° C.

NMR-$^1$H (100 MHz, CDCl$_3$, δ): 7.10 (δ, 1H, Ph—CH$_3$, J=7.5 Hz); 6.80 (m, 2H, Ph—CH$_3$); 3.10 (m, 12H, CH$_2$—N+CH$_2$—NH$_2$+piperazine); 2.30 (s, 3H, CH$_3$); 2.26 (s, 3H, CH$_3$); 1.70 (m, 2H, CH$_2$); 1.62 (s, NH$_2$).

20.2) N-[3-{4-(2,5-dimethylphenyl)-1-piperazinyl}-propyl]-α-phenyl-benzeneacetamide, 1.5 HCl, H$_2$O:

Compound 20 is prepared in a similar manner to that of Example 13 except that 3-[4-(2.5-dimethylphenyl)-1-piperazinyl]-propyl-1-amine is used in place of 3-[4-(2-methoxyphenyl)-1-piperazinyl]-propyl-1-amine; M.p.: 151° C. NMR-$^1$H (400 MHz, DMSO d6, δ): 10.96 (bs, 1H, $^+$NH); 8.62 (m, 1H, NH—CO); 7.27 (m, 10H, 2×Ph); 7.06 (δ, 1H, Ph—CH$_3$, J=7.5 Hz); 6.82 (δ, 1H, Ph—CH$_3$); 4.99 (s, 1H, CH); 3.44 (m, 2H, $^+$NH—CH$_2$); 3.18 (m, 2H, CH$_2$—NH—CO); 3.12 (m, 8H, piperazine); 2.26 (s, 3H CH$_3$); 2.19 (s, 3H, CH$_3$); 1.91 (m, 2H, CH$_2$).

Elemental analysis for C$_{29}$H$_{35}$N$_3$O, 1.5 HCl, H$_2$O: % Calc: C, 67.72; H, 7.55; N, 8.17; O, 6.22; % obtained: C, 67.56; H, 7.51; N, 8.17; O, 6.48.

EXAMPLE 21

4-chloro-a-(4-chlorophenyl)-N-[3-{4-(2,5-dimethylphenyl)-1-piperazinyl}-propyl]-benzeneacetamide, fumarate (Compound 21)

Compound 21 is prepared in a similar manner to that of Example 20 except that 4,4'-dichlorodiphenylacetic acid is used in place of diphenylacetic acid; M.p.: 139° C.

NMR-$^1$H (400 MHz, DMSO d6, δ): 8.36 (m, 1H, NH—CO); 7.34 (m, 8H, 2×Ph—Cl); 7.01 (δ, 1H, Ph—CH$_3$, J=8 Hz) 6.79 (s, 1H, Ph—CH$_3$); 6.75 (δ, 1H, Ph—CH$_3$); 6.61 (s, 2H, CH=CH); 4.95 (s, 1H, CH); 3.13 (m, 2H, CH$_2$—NH—CO); 2.81 (bs, 4H, piperazine); 2.52 (bs, 4H, piperazine); 2.38 (m, 2H, CH$_2$—N); 2.23 (s, 3H, CH$_3$); 2.17 (s, 3H, CH$_3$); 1.62 (m, 2H, CH$_2$).

Elemental analysis for C$_{29}$H$_{33}$Cl$_2$N$_3$O, fumarate: % Calc: C, 63.26; H, 5.95; N, 6.71; % obtained: C, 63.60; H, 6.03; N, 6.78.

EXAMPLE 22

(±)-N-[3-{4-(2,5-dimethylphenyl)-1-piperazinyl}-propyl]-α-hydroxy-α-methyl-benzeneacetamide, 1.25 HCl, 0.75 H$_2$O (Compound 22)

Compound 22 is prepared in a similar manner to that of Example 20 except that (±)-atrolactic acid is used in place of diphenylacetic acid; M.p.: 155° C.

NMR-$^1$H (400 MHz, DMSO d6, δ): 10.82 (bs, 1H, $^+$NH); 8.16 (m, 1H, NH—CO); 7.56 (m, 2H, Ph); 7.34 (m, 2H, Ph); 7.24 (m, 1H, Ph); 7.06 (δ, 1H, Ph—CH$_3$, J=8 Hz); 6.82 (m, 2H, Ph—CH$_3$); 4.87 (bs, OH); 3.39 (m, 2H, $^+$NH—CH$_2$); 3.17–2.97 (m, 10H, piperazine+CH$_2$—NH—CO); 2.26 (s, 3H, Ph—CH$_3$); 2.20 (s, 3H, Ph—CH$_3$); 1.86 (m, 2H, CH$_2$); 1.64 (s, 3H, CH$_3$).

Elemental analysis for C$_{24}$H$_{33}$N$_3$O$_2$, 1.25 HCl, 0.75 H$_2$O: % Calc: C, 63.41; H, 7.93; N, 9.24; O, 9.68; % obtained: C, 63.56; H, 7.83; N, 9.15; O, 9.46.

EXAMPLE 23

N-[3-{4-(2,5-dimethylphenyl)-1-piperazinyl}-propyl]-α-methyl-α-phenyl-benzeneacetamide, 1.5 HCl, 1.25 H$_2$O (Compound 23)

Compound 23 is prepared in a similar manner to that of Example 20 except that 2,2-diphenylpropionic acid is used in place of diphenylacetic acid; M.p.: 90° C.

NMR-$^1$H (400 MHz, DMSO d6, δ): 7.67 (m, 1H, NH—CO); 7.26 (m, 10H, 2×Ph); 7.07 (δ, 1H, Ph—CH$_3$, J=8 Hz); 6.82 (m, 2H, Ph—CH$_3$); 6.56 (bs, 1H, $^+$NH); 3.39 (m, 2H, $^+$NH—CH$_2$); 3.20–2.97 (m, 10H, piperazine+CH$_2$—NH—CO); 2.26 (s, 3H, Ph—CH$_3$); 2.21 (s, 3H, Ph—CH$_3$); 1.88 (m, 5H, CH$_2$+CH$_3$).

Elemental analysis for C$_{30}$H$_{37}$N$_3$O, 1.5 HCl, 1.25 H$_2$O: % Calc: C, 67.62; H, 7.76; N, 7.89; O, 6.76; % obtained: C, 67.82; H, 7.80; N, 7.51; O, 6.57.

EXAMPLE 24

N-[3-{4-(2,5dimethylphenyl)-1-piperazinyl}-propyl]-α-ethylthio-α-phenyl-benzeneacetamide, 0.5 fumarate (Compound 24)

Compound 24 is prepared in a similar manner to that of Example 20 except that 2-ethylthio-2,2-diphenylacetic acid is used in place of diphenylacetic acid; M.p.: 157° C.

NMR-$^1$H (400 MHz, DMSO d6, δ): 7.94 (m, 1H, NH—CO); 7.32 (m, 10H, 2×Ph); 7.01 (δ, 1H, Ph—CH$_3$, J=7.4 Hz); 6.75 (m, 2H, Ph—CH$_3$); 6.60 (s, 1H, ½ CH=CH); 3.60 (bs, COOH); 3.19 (m, 2H, CH$_2$—NH—CO); 2.77 (bs, 4H, piperazine); 2.50 (m, 4H, piperazine); 2.33 (m, 2H, CH$_2$—N); 2.24 (s, 3H, Ph—CH$_3$); 2.16 (m, 5H, Ph—CH$_3$+S—CH$_2$); 1.62 (m, 2H, CH$_2$); 0.99 (t, 3H, CH$_3$—CH$_2$—S, J=7.5 Hz).

Elemental analysis for C$_{31}$H$_{39}$N$_3$OS, 0.5 fumarate: % Calc: C, 70.81; H, 7.38; N, 7.51; S, 5.73; % obtained: C, 70.69; H, 7.33; N, 7.11; S, 5.96.

EXAMPLE 25

N-[3-{4-(2,5-dimethylphenyl)-1-piperazinyl}-propyl]-α-hydroxy-4-methoxy-α-(4-methoxyphenyl)-benzeneacetamide, HCl, 0.5 H$_2$O (Compound 25)

Compound 25 is prepared in a similar manner to that of Example 20 except that 4,4'-dimethoxybenzylic acid (Toda, F. et al. Chem. Letts. pp. 373–376 (1990)) is used in place of diphenylacetic acid; M.p.: 173° C.

NMR-$^1$H (400 MHz, DMSO d6, δ): 11.19 (bs, 1H, $^+$NH); 8.37 (m, 1H, NH—CO); 7.70 (bs, OH); 7.29 (δ, 4H, 2× Ph—OCH$_3$, J=8.6 Hz); 7.05 (δ, 1H, Ph—CH$_3$, J=7.7 Hz); 6.87 (δ, 4H), 2×Ph—OCH$_3$); 6.83 (m, 2H, Ph—CH$_3$); 3.73 (s, 6H, 2×OCH$_3$); 3.42 (m, 2H, $^+$NH—CH$_2$); 3.30–2.95 (m, 10H, piperazine+CH$_2$—NH—CO); 2.26 (s, 3H, Ph—CH$_3$); 2.20 (s, 3H, Ph—CH$_3$); 1.94 (m, 2H, CH$_2$).

EXAMPLE 26

N-[3-{4-(2,5dimethylphenyl)-1-piperazinyl}-propyl]-2-ethyl-2-phenyl-butyramide, dihydrochloride, monohydrate (Compound 26)

Compound 26 is prepared in a similar manner to that of Example 20 except that 2-ethyl-2-phenylbutyric acid is used in place of diphenylacetic acid; M.p.: 195° C. NMR-$^1$H (400 Mz, DMSO d6, δ): 11.12 (bs, 1H, $^+$NH); 7.65 (m, 1H, NH—CO); 7.28 (m, 10H, 2×Ph); 7.06 (δ, 1H, Ph—CH$_3$, J=8 Hz); 6.82 (m, 2H, Ph—CH$_3$); 3.40 (m, 2H, $^+$NH—CH$_2$); 3.05 (m, 8H, piperazine); 2.92 (m, 2H, CH$_2$—NH—CO); 2.26 (s, 3H, Ph—CH$_3$); 2.20 (s, 3H, Ph—CH$_3$); 1.91 (m, 6H, 3×CH$_2$); 0.63 (t, 6H, 2×CH$_3$—CH$_2$, J=7.2 Hz).

Elemental analysis for $C_{27}H_{39}N_3O$, 2 HCl, H$_2$O: % Calc: C, 63.27; H, 8.46; N, 8.20; O, 6.24; % obtained: C, 63.67; H, 8.57; N, 8.19; O, 6.43.

EXAMPLE 27

(±)-N-[3-{4-(2,5-dimethylphenyl)-1-piperazinyl}-propyl]-2-hydroxy-2-phenyl-butyramide, fumarate (Compound 27)

Compound 27 is prepared in a similar manner to that of Example 20 except that a-hydroxy-a-phenyl-butyric acid is used in place of diphenylacetic acid; M.p.: 179° C.

NMR-$^1$H (400 MHz, DMSO d6, δ): 8.03 (m, 1H, NH—CO); 7.55 (δ, 2H, Ph, J=7.5 Hz); 7.30 (m, 2H, Ph); 7.22 (m, 1H, Ph); 7.02 (δ, 1H, Ph—CH$_3$, J=7.5 Hz); 7.5 Hz); 6.81 (s, 1H, Ph—CH$_3$); 6.76 (δ, 1H, Ph—CH$_3$); 6.60 (s, 2H, CH═CH); 3.10 (m, 2H, CH$_2$—NHCO); 2.86 (bs, 4H, piperazine); 2.58 (bs, 4H, piperazine); 2.41 (m, 2H, CH$_2$—N); 2.24 (s, 3H, CH$_3$); 2.21 (m, 1H, CH$_2$—CH$_3$); 2.17 (s, 3H, CH$_3$); 1.86 (m, 1H, CH$_2$—CH$_3$); 1.60 (m, 2H, CH$_2$); 0.79 (t, 3H, CH$_2$—CH$_3$, J=7.2 Hz).

Elemental analysis for $C_{25}H_{35}N_3O_2$, fumarate: % Calc: C, 66.27; H, 7.48; N, 7.99; % obtained: C, 66.28; H, 7.35; N, 7.98.

EXAMPLE 28

(±)-N-[3-{4-(2,5-dimethylphenyl)-1-piperazinyl}-propyl]-2-hydroxy-2-phenyl-hexanamide, fumarate (Compound 28)

28.1) Acid (±)-2-hydroxy-2-phenyl-hexanoïque:

This intermediate is described by Newcomb M. et al. (J. Org. Chem. 43:3963 (1978)); M.p.: 102° C.

NMR-$^1$H (100 MHz, CDCl$_3$, δ): 7.52 (m, 5H, Ph); 5.75 (bs, OH+COOH), 2.10 (m, 2H, CH$_2$—C—OH); 1.33 (m, 4H, CH$_2$—CH$_2$); 0.90 (m, 3H, CH$_3$).

28.2) (±)-N-[3-{4-(2,5-dimethylphenyl)-1-piperazinyl}-propyl]-2-hydroxy-2-phenyl-hexanamide, fumarate:

Compound 28 is prepared in a similar manner to that of Example 20 except that (±)-2-hydroxy-2-phenyl-hexanoic acid is used in place of diphenylacetic acid; M.p.: 147° C.

NMR-$^1$H (400 MHz, DMSO d6, δ): 8.01 (m, 1H, NH—CO); 7.55 (δ, 2H, Ph, J=7.5 Hz); 7.25 (m, 3H, Ph); 7.02 (δ, 1H, Ph—CH$_3$, J=7.5 Hz); 6.81 (s, 1H, Ph—CH$_3$); 6.76 (δ, 1H, Ph— CH$_3$); 6.60 (s, 2H, CH═CH); 5.85 (bs, OH+COOH); 3.10 (m, 2H, CH$_2$—NHCO); 2.85 (bs, 4H, piperazine); 2.57 (bs, 4H, piperazine); 2.39 (m, 2H, CH$_2$—N); 2.24 (s, 3H, Ph—CH$_3$); 2.17 (s, 3H, Ph—CH$_3$); 2.14 (m, 1H, ½ CH$_2$—C—OH); 1.84 (m, 1H, ½ CH$_2$—C—OH); 1.59 (m, 2H, CH$_2$); 1.25 (m, 4H, CH$_2$—CH$_2$—CH$_3$); 1.18 (t, 3H, CH$_2$—CH$_3$, J=6.9 Hz).

Elemental analysis for $C_{27}H_{39}N_3O_2$, fumarate: % Calc: C, 67.25; H, 7.83; N, 7.59; % obtained: C, 66.76; H, 7.69; N, 7.58.

EXAMPLE 29

(±)-2-chloro-N-[3-{4-(2,5-dimethylphenyl)-1-piperazinyl}-propyl]-α-hydroxy-α-methyl-benzeneacetamide, fumarate, monohydrate (Compound 29)

29.1) (±)-2-chloro-α-hydroxy-α-methyl-benzeneacetonitrile:

This compound is synthesized using the same procedure as that described by Gassman, P. G. et al. Tetrahedron Lett. 40:3773 (1978).

NMR-$^1$H (100 MHz, CDCl$_3$, δ): 7.50 (m, 4H, Ph); 3.78 (bs, 1H, OH); 2.06 (s, 3H, CH$_3$).

29.2) (±)-2-chloro-α-hydroxy-α-methyl-benzeneacetic acid:

A mixture of 2.3 g (12.7 mmol) of (±)-2-chloro-α-hydroxy-α-methyl-benzeneacetonitrile and 20 ml of concentrated HCl is heated at 60° C. for 3 hours then refluxed for 2 hours. After cooling down, the reaction mixture is concentrated under reduced pressure and the residue is separated with diethylether (50 ml) and 1N NaOH (50 ml). The organic phase is extracted twice with 25 ml of 1N NaOH, and all the basic phases are collected together before acidification with concentrated HCl. The product is extracted with 2×50 ml of diethylether, then the solution is dried over sodium sulphate and evaporated under vacuum in order to produce 930 mg (36%) of a white powder; M.p.: 110–111° C.

NMR-$^1$H (100 MHz, CDCl$_3$, δ): 7.50 (m, 4H, Ph); 6.47 (bs, 2H, OH+COOH); 1.90 (s, 3H, CH$_3$).

29.3) (±)-2-chloro-N-[3-{4-(2,5-dimethylphenyl)-1-piperazinyl}-propyl]-α-hydroxy-α-methyl-benzeneacetamide, fumarate, monohydrate:

Compound 29 is prepared in a similar manner to that of Example 20 except that (±)-2-chloro-a-hydroxy-a-methyl-benzeneacetic acid is used in place of diphenylacetic acid; M.p.: 84° C.

NMR-$^1$H (400 MHz, DMSO d6, δ): 7.90 (m, 1H, NH—CO); 7.62 (m, 1H, Ph—Cl); 7.34 (m, 3H, Ph—Cl); 7.03 (δ, 1H, Ph—CH$_3$, J=7.5 Hz), 6.78 (m, 2H, Ph—CH$_3$); 6.61 (s, 2H, CH═CH); 6.02 (bs, OH+COOH); 3.19 (m, 2H, CH$_2$—NHCO); 2.90 (bs, 4H, piperazine); 2.76 (bs, 4H, piperazine); 2.62 (m, 2H, CH$_2$—N); 2.24 (s, 3H, CH$_3$); 2.18 (s, 3H, CH$_3$); 1.72 (m, 5H, CH$_2$+CH$_3$).

Elemental analysis for $C_{24}H_{32}ClN_3O_2$, fumarate, H$_2$O: % Calc: C, 59.62; H, 6.79; N, 7.45; % obtained: C, 59.54; H, 6.47; N, 7.10.

EXAMPLE 30

(±)-4-chloro-N-[3-{4-(2,5-dimethylphenyl)-1-piperazinyl}-propyl]-α-hydroxy-α-methyl-benzeneacetamide, 1.25 HCl, 0.5 H$_2$O (Compound 30)

30.1) (±)-4-chloro-a-hydroxy-a-methyl-benzeneacetic acid:

This compound is prepared in a similar manner to that of intermediate 29.2 except that (±)-4-chloro-α-hydroxy-α-methyl-benzeneacetonitrile (Gassman, P. G. et al. Tetrahedron Lett. 40:3773 (1978)) is used in place of (±)-2-chloro-α-hydroxy-α-methyl benzeneacetonitrile.

NMR-$^1$H (100 MHz, CDCl$_3$, δ): 7.45 (m, 4H, Ph); 6.80 (bs, 2H, OH+COOH); 1.80 (s, 3H, CH$_3$).

30.2) (±)-4-chloro-N-[3-{4-(2,5-dimethylphenyl)-1-piperazinyl}-propyl]-α-hydroxy-α-methyl-benzeneacetamide, 1.25 HCl, 0.5 H$_2$O:

Compound 30 is prepared in a similar manner to that of Example 20 except that (±)-4-chloro-a-hydroxy-a-methyl-benzeneacetic acid is used in place of diphenylacetic acid; M.p.: 161.5° C.

NMR-$^1$H (400 MHz, DMSO d6, δ): 10.95 (bs, 1H, $^+$NH); 8.20 (m, 1H, NH—CO); 7.56 (m, 2H, Ph—Cl); 7.39 (m, 2H, Ph—Cl); 7.06 (δ, 1H, Ph—CH$_3$, J=8 Hz); 6.82 (m, 2H, Ph—CH$_3$); 5.70 (bs, OH); 3.44 (m, 2H, $^+$NH—CH$_2$); 3.16–2.99 (m, 10H, piperazine+CH$_2$—NH—CO); 2.26 (s, 3H, Ph—CH$_3$); 2.20 (s, 3H, Ph—CH$_3$); 1.87 (m, 2H, CH$_2$); 1.62 (s, 3H, CH$_3$).

Elemental analysis for C$_{24}$H$_{32}$ClN$_3$O$_2$, 1.25 HCl, 0.5 H$_2$O: % Calc: C, 59.49; H, 7.12; N, 8.67; % obtained: C, 59.46; H, 7.01; N, 8.51.

EXAMPLE 31

(±)-3-chloro-N-[3{4-(2,5-dimethylphenyl)-1-piperazinyl}-propyl]-α-hydroxy-α-methyl-benzeneacetamide, fumarate (Compound 31)

31.1) Ethyl-ester of (±)-3-chloro-α-hydroxy-α-methyl-benzeneacetic acid:

400 mg (0.016 a.g.) of magnesium powder, a few drops of a solution of 3-bromochlorobenzene (1.94 ml, 16.5 mmol) in 10 ml of dry diethylether, and one crystal iodine are introduced into an anhydrous three-necked flask equipped with a nitrogen supply, a funnel, and a reflux condenser. The mixture is gently heated until the reaction starts, then the remainder of 3-bromochlorobenzene is added dropwise at a rate which maintains reflux. Agitation is continued until the magnesium completely disappears (about 1 hour). The 3-chlorophenylmagnesium bromide thus formed is then brought via a cannula into a solution cooled down beforehand (−78° C.) of 1.64 ml (15 mmol) of ethyl pyruvate 15 ml of dry diethylether. After this addition is completed, the temperature of reaction is left to slowly rise to 20° C. and the mixture is agitated overnight. The reaction mixture is rapidly cooled down to 0° C. by the addition of 3N HCl (10 ml) and extracted with 2×20 ml of diethylether. The organic extract is then rinsed with water (2×20 ml), a saturated solution of sodium chloride (20 ml), and dried over sodium sulphate. Evaporation of the solvent under reduced pressure allows a yellow oil to be obtained which is purified on a chromatography column (eluant: light oil (bp. 40–65° C.)/ethyl acetate: 95/5). 2.16 g (57%) of a pure colourless oil id obtained.

NMR-$^1$H (100 MHz, CDCl$_3$, δ): 7.60–7.25 (m, 4H, Ph); 4.23 (q, 2H, CH$_2$, J=7.0 Hz); 3.89 (s, 1H, OH); 1.75 (s, 3H, CH$_3$); 1.29 (t, 3H, CH$_2$—CH$_3$).

31.2) (±)-3-chloro-α-hydroxy-α-methyl-benzeneacetic acid:

A solution of 1.24 g (18.8 mmol) of KOH in 10 ml of H$_2$O is added dropwise to a solution of 2.16 g (9.44 mmol) of the ethyl-ester of (±)-3-chloro-α-hydroxy-α-methyl-benzeneacetic acid in 20 ml of cold ethanol (0–5° C.). Agitation is continued for 3 hours at 25° C., and the solvent is evaporated off. The residue is separated with H$_2$O and diethylether. After decantation, the aqueous layer is acidified at 0° C. with 3N HCl and extracted with 2×50 ml of diethylether. The diethylether extract is dried over sodium of sulphate and the solvent is evaporated off under reduced pressure so as to obtain 1.76 g (93%) of a white powder M.p.: 110–111° C.

NMR-$^1$H (100 MHz, CD$_3$OD, δ): 7.80–7.42 (m, 4H, Ph); 1.89 (s, 3H, CH$_3$).

31.3) (±)-3-chloro-N-[3-{4-(2,5-dimethylphenyl)-1-piperazinyl}-propyl]-α-hydroxy-α-methyl-benzeneacetamide, fumarate:

Compound 31 is prepared in a similar manner to that of Example 20 except that (±)-3-chloro-a-hydroxy-a-methyl-benzeneacetic acid is used in place of diphenylacetic acid: M.p.: 80–81° C.

NMR-$^1$H (400 MHz, DMSO d6, δ): 8.17 (m, 1H, NH—CO); 7.57 (s, 1H, Ph—Cl); 7.49 (δ, 1H, Ph—Cl, J=7.63 Hz); 7.34 (m, 2H, Ph—Cl); 6.61 (s, 2H, —CH=CH—); 3.10 (m, 2H, CH$_2$—NHCO); 2.86 (bs, 4H, piperazine); 2.58 (bs, 4H, piperazine); 2.40 (m, 2H, CH$_2$—N); 2.24 (s, 3H, Ph—CH$_3$); 2.18 (s, 3H, Ph—CH$_3$); 1.59 (m, 5H, CH$_2$+CH$_3$).

Elemental analysis for C$_{24}$H$_{32}$ClN$_3$O$_2$, fumarate: % Calc: C, 61.59; H, 6.65; N, 7.70; % obtained: C, 61.18; H, 6.60; N, 7.60.

EXAMPLE 32

(±)-a-amino-N-[3-{4-(2,5-dimethylphenyl)-1-piperazinyl}-propyl]-benzeneacetamide, difumarate (Compound 32)

32.1) (±)-α-tert-butoxycarbonylamino-N-[3-{4-(2,5-dimethylphenyl)-1-piperazinyl}-propyl]-benzeneacetamide:

This compound is prepared in a similar manner to that of Example 20 except that (±)-Boc-phenylglycine is used in place of diphenylacetic acid.

NMR-$^1$H (100 MHz, CDCl$_3$, δ): 7.35 (m, 6H, Ph+NH—CO); 7.01 (δ, 1H, Ph—CH$_3$, J=7.5 Hz); 6.85 (s, 1H, Ph—CH$_3$); 6.79 (δ, 1H, Ph—CH$_3$); 5.90 (m, 1H, NH-Boc); 5.10 (δ, 1H, CH); 3.38 (m, 2H, CH$_2$—NHCO); 3.00–2.30 (m, 10H, piperazine+CH$_2$—N); 2.35 (s, 3H, CH$_3$); 2.25 (s, 3H, CH$_3$); 1.65 (m, 2H, CH$_2$); 1.40 (s, 9H, tBu).

32.2) {±)-α-amino-N-[3-{4-(2,5-dimethylphenyl)-1-piperazinyl}-propyl]-benzeneacetamide, difumarate A solution of 1.47 g (3 mmol) of (±)-α-tert-butoxycarbonylamino-N-[3-{4-(2,5-dimethylphenyl)-1-piperazinyl}-propyl]-benzeneacetamide in 20 ml of 1,4-dioxane is cooled down to 0° C. before the addition of 7.5 ml (30 mmol) of a solution of 4N HCl in 1,4-dioxane. After agitation overnight at the ambient temperature, the reaction mixture is concentrated under vacuum. The residue is suspended in 50 ml of ethyl acetate and rinsed with 2×50 ml of 1N NaOH. After drying over anhydrous sodium sulphate, the organic phase is concentrated in order to produce 1.10 g (95%) a colourless oil. This is converted into its fumarate salt as described above; M.p.: 122–123° C.

NMR-$^1$H (400 MHz, DMSO d6, δ): 9.90 (bs, NH$_3$$^+$); 8.52 (m, 1H, NH—CO); 7.47 (m, 5H, Ph); 7.03 (δ, 1H, Ph—CH$_3$, J=7.5 Hz); 6.79 (s, 1H, Ph—CH$_3$); 6.75 (δ, 1H, Ph—CH$_3$); 6.55 (s, 4H, 2×—CH=CH—); 4.82 (s, 1H, CH); 3.12 (m, 2H, CH$_2$—NHCO); 2.80 (bs, 4H, piperazine); 2.50 (bs, 4H, piperazine); 2.32 (m, 2H, CH$_2$—N); 2.23 (s, 3H, CH$_3$); 2.17 (s, 3H, CH$_3$); 1.59 (m, 2H, CH$_2$).

Elemental analysis for C$_{23}$H$_{32}$N$_4$O, difumarate: % Calc: C, 60.77; H, 6.58; N, 9.14; % obtained: C, 60.61; H, 6.51; N, 8.87.

EXAMPLE 33

(±)-N-[3-{4-(2,5-dimethylphenyl)-1-piperazinyl}-propyl]-α-(methylsulphonylamino)-benzeneacetamide, HCl, 0.5 $H_2O$ (Compound 33)

33.1) (±)-α-(methylsulphonylamino)-benzeneacetic acid:

A solution of 1N NaOH (25 ml) is added dropwise to an agitated suspension of 3.78 g (25 mmol) of (±)-phenylglycine in 10 ml $H_2O$ until complete dissolution, 2.7 ml (35 mmol) of methanesulphonyl chloride is added under vigorous agitation followed by 1N NaOH in a small quantity in order to maintain the alkalinity of the mixture at about pH 9. After stabilisation of the pH, agitation is continued at ambient temperature for one hour. The reaction mixture is then acidified with 4N HCl and extracted with 2×50 ml of ethyl acetate. The organic phase is rinsed with 50 ml 1N HCl followed by 2×25 ml of a saturated solution of sodium chloride and finally dried over sodium sulphate. Filtration and evaporation of the solvent allows a yellow oil to be obtained which crystallizes slowly when it is left overnight at ambient temperature. The yellow crystals are filtered and rinsed with a mixture of light oil (bp, 40–65° C.) and diethylether in order to produce 1.87 g (32%) of a white powder, M.p.=117° C.

NMR-$^1$H (100 MHz, CDCl$_3$, δ): 9.79 (bs, 1H, COOH); 7.40 (bs, 5H, Ph); 5.93 (δ, 1H, SO$_2$NH, J=7.0 Hz); 5.25 (δ, 1H, CH); 2.74 (s, 3H, CH$_3$).

33.2) (±)-N-[3-{4-(2,5-dimethylphenyl)-1-piperazinyl}-propyl]-α-(methylsulphonylamino)-benzeneacetamide, HCl, 0.5 $H_2O$:

Compound 33 is prepared in a similar manner to that of Example 20 except that (±)-α-(methylsulphonylamino)-benzeneacetic acid is used in place of diphenylacetic acid; M.p.: 151–152° C.

NMR-$^1$H (400 MHz, DMSO d6, δ): 11.05 (bs, 1H, $^+$NH); 8.64 (m, 1H, NH—CO); 7.98 (m, 1H, NHSO$_2$); 7.50 (δ, 2H, Ph, J=7.55 Hz); 7.36 (m, 3H, Ph); 7.06 (δ, 1H, Ph—CH$_3$, J=7.5 Hz); 6.82 (m, 2H, Ph—CH$_3$); 5.03 (δ, 1H, CH, J=6.8 Hz); 3.48 (m, 2H, $^+$NH—CH$_2$); 3.09 (m, 10H, piperazine+CH$_2$—NH—CO); 2.76 (s, 3H, CH$_3$—SO$_2$); 2.26 (s, 3H, Ph—CH$_3$); 2.20 (s, 3H, Ph—CH$_3$); 1.90 (m, 2H, CH$_2$); 1.62 (s, 3H, CH$_3$).

Elemental analysis for C$_{24}$H$_{34}$ClN$_4$O$_3$S, HCl, 0.5 $H_2O$: % Calc: C, 57.19; H, 7.20; N, 11.11; S, 6.36; % obtained: C, 57.27; H, 7.09; N, 11.04; S, 6.09.

EXAMPLE 34

(±)-N-[3-{4-(2,5-dimethylphenyl)-1-piperazinyl}-propyl]-2-hydroxy-2-methyl-4-methoxy-benzenepropionamide, fumarate (Compound 34)

34.1) (±)-2-hydroxy-2-methyl-4-methoxy-benzenepropionitrile:

This compound is synthesized using the same procedure as that described by Gassman, P. G. et al. Tetrahedron Lett. 40:3773 (1978).

NMR-$^1$H (100 MHz, CDCl$_3$, δ): 7.10 (m, 4H, Ph); 3.81 (s, 3H, OCH$_3$); 2.98 (AB, 2H, CH$_2$, J$_{AB}$=14 Hz ); 2.70 (bs, 1H, OH), 1.64 (s, 3H, CH$_3$).

34.2) (±)-2-hydroxy-2-methyl-4-methoxy-benzenepropionic acid

This compound is prepared in a similar manner to that of intermediate 29.2 except that (±)-2-hydroxy-2-methyl-4-methoxy-benzenepropionitrile is used in place of (±)-2chloro-α-hydroxy-α-methyl-benzeneacetronitrile.

NMR-$^1$H (100 MHz, CDCl$_3$, δ): 7.00 (m, 4H, Ph); 5.66 (bs, 2H, OH+COOH); 3.79 (s, 3H, OCH$_3$); 3.00 (AB, 2H, CH$_2$, J$_{AB}$=13.7 Hz); 1.51 (s, 3H, CH$_3$).

34.3) (±)-N-[3-{4-(2,5-dimethylphenyl)-1-piperazinyl}-propyl]-2-hydroxy-2-methyl-4-methoxy-benzenepropionamide, fumarate:

Compound 34 is prepared in a similar manner to that of Example 20 except that (±)-2-hydroxy-2-methyl-4-methoxy-benzenepropionic acid is used in place of diphenylacetic acid; M.p.: 142° C.

NMR-$^1$H (400 MHz, DMSO d6, δ): 7.66 (m, 1H, NH—CO); 7.08–6.73 (m, 7H, Ph—CH$_3$+Ph—OCH$_3$); 6.61 (s, 2H, CH=CH); 5.30 (bs, OH+COOH); 3.69 (s, 3H, OCH$_3$); 3.16 (m, 1H, ½ CH$_2$—NHCO); 2.95 (m, 1H, ½ CH$_2$—NHCO); 2.82 (bs, 4H, piperazine); 2.78 (AB, 2H, CH$_2$—PhOCH$_3$, J$_{AB}$=13.35 Hz); 2.50 (bs, 4H, piperazine); 2.32 (m, 2H, CH$_2$—N); 2.25 (s, 3H, CH$_3$); 2.17 (s, 3H, CH$_3$); 1.47 (m, 2H, CH$_2$); 1.26 (s, 3H, CH$_3$).

Elemental analysis for C$_{26}$H$_{37}$N$_3$O$_3$, fumarate: % Calc: C, 64.85; H, 7.44; N, 7.56; % obtained: C, 64.59; H, 7.42; N, 7.49.

EXAMPLE 35

N-[3-{4-(2,5-dimethylphenyl)-1piperazinyl}-propyl]-N-methyl-α-phenyl-benzeneacetamide, 0.75 fumarate (Compound 35)

35.1) N-(3-hydroxypropyl)-N-methyl-α-phenyl-benzeneacetamide:

The compound mentioned in the title is prepared in a similar manner to that of intermediate 1.1 except that N-methyl-3-hydroxypropylamine (Koepke, S. R. et al. J. Org. Chem. 44:2718 (1979)) is used in place of 3-amino-1-propanol.

NMR-$^1$H (400 MHz, CDCl$_3$, δ): 7.29 (m, 10H, 2×Ph); 5.24 (s, 1H, CH); 3.58 (m, 2H, CH$_2$—NCO); 3.48 (m, 2H, CH$_2$OH); 3.00 (s, 3H, CH$_3$) 1.71 (m, 2H, CH$_2$).

35.2) N-(3-iodopropyl)-N-methyl-α-phenyl-benzeneacetamide:

The compound mentioned in the title is prepared in a similar manner to that of intermediate 1.2 except that N-(3-hydroxypropyl)-N-methyl-α-phenyl-benzeneacetamide is used in place of α-hydroxy-N-(3-hydroxypropyl)-α-phenyl-benzeneacetamide. NMR-$^1$H (400 MHz, CDCl$_3$, δ): 7.32 (m, 10H, 2×Ph); 5.18 (s, 1H, CH); 3.50 (m, 2H, CH$_2$—NCO); 3.12 (m, 2H, CH$_2$—I); 3.00 (s, 3H, CH$_3$); 2.10 (m, 2H, CH$_2$).

35.3) N-[3-{4-(2,5-dimethylphenyl)-1-piperazinyl)-propyl]-N-methyl-α-phenyl-benzeneacetamide, 0.75 fumarate:

A mixture of 2 g (5 mmol) of N-(3-iodopropyl)-N-methyl-α-phenyl-benzeneacetamide and 970 mg (54 mmol) of 1-(2,5-dimethylphenyl)-piperazine in 15 ml of acetonitrile is heated under reflux for 4 hours. After cooling down, the solvent is evaporated off under reduced pressure, and the residue is treated as described in Example 1 except for the column chromatography (eluant: ethyl acetate/ethanol: 90/10). The putting into salt form is carried out in the presence of an equivalent of fumaric acid in ethanol under reflux in order to produce the compound mentioned in the title in the form of a white solid; M.p.: 192° C.

NMR-$^1$H (400 MHz, DMSO d6, δ): 7.25 (m, 10H, 2×Ph); 7.02 (δ, 1H, Ph—CH$_3$, J=7.5 Hz); 6.77 (m, 2H, Ph—CH$_3$); 6.61 (s, 1.5H, 0.75 CH=CH); 5.52 (s, 0.5H, CH); 5.45 (s, 0.5H, CH); 3.37 (m, 2H, CH$_2$—N(CH$_3$)—CO); 2.98 (s, 1.5H, NCH$_3$); 2.86 (s, 1.5H, NCH$_3$); 2.82 (bs, 4H, piperazine); 2.60 (bs, 4H, piperazine); 2.40 (m, 1H, CH$_2$—N); 2.34 (m, 1H, CH$_2$—N) 2.23 (s, 3H, Ph—CH$_3$); 2.17 (s, 3H, Ph—CH$_3$); 1.67 (m, 2H, CH$_2$).

Elemental analysis for C$_{30}$H$_{37}$N$_3$O, 0.75 fumarate: % Calc: C, 73.04; H, 7.43; N, 7.74; % obtained: C, 72.54; H, 7.30; N, 7.29.

EXAMPLE 36

(±)-N-[3-{4-(2-(1-hydroxypropyl)-phenyl)-1-piperazinyl}-propyl]-α-phenyl-benzeneacetamide, fumarate (Compound 36)

36.1) 2-(4benzyl-1-piperazinyl)-benzaldehyde:

4.24 ml (40 mmol) of 2-fluorobenzaldehyde, 8.34 ml (48 mmol) of N-benzylpiperazine and 6.62 g (48 mmol) of K$_2$CO$_3$ in 60 ml of DMF are heated at 150° C. for 7 hours. After cooling down, the mixture is covered with 200 ml of ethyl acetate, and the organic phase is rinsed successively with 2×50 ml of H$_2$O and 2×50 ml of a saturated solution of NaCl. After drying over Na$_2$SO$_4$, the ethyl acetate is evaporated off in order to obtain a brown oil which is purified by chromatography on silica gel (eluant: light oil (bp. 40–65° C.)/ethyl acetate: 9/1 then 8/2). Evaporation of the appropriate fractions under reduced pressure produces 10.91 g (91%) of a white solid; M.p.: 60° C.

NMR-$^1$H (100 MHz, CDCl$_3$, δ): 10.32 (s, 1H, CHO); 7.78 (m, 1H, Ph—CHO); 7.47 (m, 1H, Ph—CHO); 7.32 (s, 5H, Ph); 7.10 (m, 2H, Ph—CHO); 3.60 (s, 2H, CH$_2$—Ph); 3.12 (m, 4H, piperazine); 2.68 (m, 4H, piperazine).

36.2) (±)-2-(4-benzyl-1-piperazinyl)-α-ethyl-benzenemethanol:

A solution of 1.8 ml (5.3 mmol, 3M solution in diethylether) of ethylmagnesium bromide in 10 ml of dry diethylether is introduced into an anhydrous three-necked flask equipped with a nitrogen supply. 1 g (3.5 mmol) of 2-(4-benzyl-1-piperazinyl)-benzaldehyde diluted in 5 ml of dry diethylether is added dropwise to this solution which has been previously cooled down (0 to 5° C.), and agitation is continued for 30 minutes at ambient temperature. The reaction mixture is then hydrolyzed at 0° C. with a concentrated solution of ammonium chloride and finally diluted with 50 ml of ethyl acetate. After decantation, the organic phase is rinsed successively with 2×20 ml of water and 20 ml of a concentrated solution of NaCl. After drying over Na$_2$SO$_4$, the ethyl acetate is evaporated off under vacuum in order to produce 880 mg (81%) of a colourless oil which crystallizes slowly at ambient temperature; M.p.: 97° C.

NMR-$^1$H (100 MHz, CDCl$_3$, δ): 7.25 (m, 9H, 2×Ph); 6.55 (bs, OH); 4.70 (t, 1H, CH, J=7 Hz); 3.55 (s, 2H, CH$_2$—Ph); 2.98 (m, 4H, piperazine); 2.60 (m, 4H, piperazine); 1.78 (m, 2H, CH$_2$—CH$_3$); 1.00 (t, 3H, CH$_2$—CH$_3$, J=7 Hz).

36.3) (±)-2-(1-piperazinyl)-α-ethyl-benzenemethanol:

456 mg (1.5 mmol) of 2-(4-benzyl-1-piperazinyl)-α-ethyl-benzenemethanol is dissolved in 30 ml of ethanol and hydrogenated on 10% Pd/C at 40 PSI 40° C. in a Parr apparatus. After 4 hours, the reaction mixture is filtered through Celite, and the filtrate is concentrated under reduced pressure to produce 330 mg (100%) of the compound mentioned in the title in the form of a white solid; M.p.: 95° C.

NMR-$^1$H (100 MHz, CDCl$_3$, δ): 7.21 (m, 4H, Ph); 4.72 (t, 1H, CH, J=7 Hz); 3.00 (m, 8H, piperazine); 2.30 (bs, OH); 1.80 (m, 2H, CH$_2$—CH$_3$); 1.05 (t, 3H, CH$_2$—CH$_3$, J=7 Hz).

36.4) N-(3-hydroxypropyl)-α-phenyl-benzeneacetamide:

The compound mentioned in the title is prepared in a similar manner to that of intermediate 1.1 except that diphenylacetic acid is used in place of benzylic acid; M.p.: 85° C.

NMR-$^1$H (400 MHz, CDCl$_3$, δ): 7.26 (m, 10H, 2×Ph); 6.18 (m, 1H, NH—CO); 4.92 (s, 1H, CH); 3.55 (m, 2H, CH$_2$—NHCO); 3.41 (m, 2H, CH$_2$OH); 3.18 (bs, OH); 1.60 (m, 2H, CH$_2$).

36.5) N-(3-iodopropyl)-α-phenyl-benzeneacetamide:

The compound mentioned in the title is prepared in a similar manner to that of intermediate 1.2 except that N-(3-hydroxypropyl)-α-phenyl-benzeneacetamide is used in place of α-hydroxy-N-(3-hydroxypropyl)-α-phenyl-benzeneacetamide; M.p.: 114° C.

NMR-$^1$H (400 MHz, CDCl$_3$, δ): 7.30 (m, 10H, 2×Ph); 5.75 (m, 1H, NH—CO); 4.92 (s, 1H, CH); 3.38 (q, 2H, CH$_2$—NHCO, J=6.53 Hz); 3.09 (t, 2H, CH$_2$I, J=6.75 Hz); 2.02 (m, 2H, CH$_2$).

36.6) (±)-N-[3-{4-(2-(1-hydroxypropyl)-phenyl)-1-piperazinyl}-propyl]-α-phenyl-benzeneacetamide, fumarate:

710 mg (3.22 mmol) of (±)-2-(1-piperazinyl)-α-ethyl-benzenemethanol and 1.21 g (3.22 mmol) of N-(3-iodopropyl)-α-phenyl-benzeneacetamide are refluxed in 20 ml of acetonitrile for 4 hours. After cooling down, the solvent is eliminated under reduced pressure, and the residue is treated as described in Example 1 except for the column chromatography (eluant: ethyl acetate/methanol: 98/2). Evaporation of the collected fractions under reduced pressure produces 0.74 g (49%) of the base of the compound mentioned in the title which is converted into its fumarate salt by heating with an equivalent of fumaric acid in absolute ethanol; M.p.: 76° C.

NMR-$^1$H (400 MHz, DMSO d6, δ): 8.29 (m, 1H, NH—CO); 7.41–7.09 (m, 14H, 2×Ph+Ph—N); 6.61 (s, 2H, CH=CH); 4.92 (s, 1H, CH); 4.85 (m, 1H, CH(OH)); 3.13 (m, 2H, CH$_2$—NHCO); 2.95 (m, 2H, piperazine); 2.69 (m, 2H, piperazine); 2.50 (bs, 4H, piperazine); 2.37 (m, 2H, CH$_2$N); 1.55 (m, 4H, CH$_2$+CH$_2$—CH$_3$); 0.86 (t, 3H, CH$_2$—CH$_3$, J=7.4 Hz).

Elemental analysis for C$_{30}$H$_{37}$N$_3$O$_2$, fumarate: % Calc: C, 69.49; H, 7.03; N, 7.15; % obtained: C, 69.31; H, 7.22; N, 7.33.

EXAMPLE 37

(±)-N-[3-{4-(2-(1-methoxypropyl)-phenyl)-1-piperazinyl}-propyl]-α-phenyl-benzeneacetamide, fumarate (Compound 37)

37.1) (±)-1-benzyl-4-[2-(1-methoxypropyl)-phenyl]-piperazine 1.55 g (5 mmol) of intermediate 36.1 in 50 ml of dry DMF is dissolved in an anhydrous three-necked flask equipped with a nitrogen supply. 220 mg (5.5 mmol) of sodium hydride (a 60% dispersion in oil) is added in one go and the reaction mixture is agitated overnight at ambient temperature before the addition of 0.22 ml (5.5 mmol) of methyl iodide diluted with 2 ml of dry DMF. Agitation is continued for another 2 hours, the mixture is concentrated under reduced pressure and the residue fractionated between 50 ml of ethyl acetate and 25 ml of 1N NaOH. After decantation, the organic phase is rinsed successively with 25 ml of 1N NaOH and 25 ml of a concentrated solution of sodium chloride. Filtration and evaporation of the solvent produces an oil which is purified by flash chromatography (eluant:

light oil (bp. 40–65° C.)/ethyl acetate: 80/20). The pure fractions are collected and concentrated in order to produce 0.71 g (68%) of a colourless oil.

NMR-$^1$H (100 MHz, CDCl$_3$, δ): 7.30 (m, 9H, 2×Ph); 4.70 (m, 1H, CH); 3.60 (s, 2H, C$\underline{H_2}$—Ph); 3.19 (s, 3H, OCH$_3$); 3.10–2.40 (m, 8H, piperazine); 1.70 (m, 2H, C$\underline{H_2}$—CH$_3$); 0.92 (t, 3H, CH$_2$—C$\underline{H_3}$, J=7.0 Hz).

37.2) (±)-1-[2-(1-methoxypropyl)-phenyl]-piperazine:

Hydrogenation is carried out as described for intermediate 36.3.

NMR-$^1$H (100 MHz, CDCl$_3$, δ): 7.28 (m, 4H, Ph); 4.70 (m, 1H, CH); 3.18 (s, 3H, OCH$_3$); 3.12–2.70 (m, 8H, piperazine); 1.70 (m, 2H, C$\underline{H_2}$—CH$_3$); 0.92 (t, 3H, CH$_2$—C$\underline{H_3}$, J=7.0 Hz).

37.3) (±)-N-[3-{4-(2-(1-methoxypropyl)-phenyl)-1-piperazinyl}-propyl]-α-phenyl-benzeneacetamide, fumarate:

Compound 37 is prepared in a similar manner to that of Example 36 except that (±)-1-[2-(1-methoxypropyl)-phenyl]-piperazine is used in place of (±)-2-(1-piperazinyl)-α-ethyl-benzenemethanol.

NMR-$^1$H (400 MHz, DMSO d6, δ): 8.31 (m, 1H, NH—CO); 7.22 (m, 14H, 2×Ph+Ph—N); 6.61 (s, 2H, CH=CH); 4.93 (s, 1H, CH); 4.59 (m, 1H, C$\underline{H}$(OCH$_3$)); 3.14 (m, 2H, C$\underline{H_2}$—NHCO); 3.07 (s, 3H, OCH$_3$); 2.95–2.50 (m, 8H, piperazine); 2.43 (m, 2H, CH$_2$N); 1.60 (m, 4H, C$\underline{H_2}$+CH$_2$—CH$_3$); 0.86 (t, 3H, CH$_2$—C$\underline{H_3}$, J=7.33 Hz).

EXAMPLE 38

(±)-N-[3-{4-(2,5-dimethylphenyl)-1-piperazinyl}-propyl]-α-methyl-benzeneacetamide, fumarate
(Compound 38)

The compound mentioned in the title is prepared in a similar manner to that of Example 20 except that (±)-2-phenylpropionic acid is used in place of diphenylacetic acid; M.p.: 136° C.

NMR-$^1$H (400 MHz, DMSO d6, δ): 7.97 (m, 1H, NH—CO); 7.25 (m, 5H, Ph); 7.02 (d, 1H, P$\underline{h}$—CH$_3$, J=7.5 Hz); 6.80 (s, 1H, P$\underline{h}$—CH$_3$); 6.78 (d, 1H, P$\underline{h}$—CH$_3$); 6.60 (s, 2H, CH=CH); 3.58 (m, 1H, CH); 3.07 (m, 2H, C$\underline{H_2}$—NHCO); 2.82 (bs, 4H, piperazine); 2.57 (bs, 4H, piperazine); 2.39 (m, 2H, CH$_2$—N); 2.23 (s, 3H, Ph—C$\underline{H_3}$); 2.17 (s, 3H, Ph—C$\underline{H_3}$); 1.59 (m, 2H, CH$_2$); 1.32 (d, 3H, CH$_3$, J=7 Hz).

Elemental analysis for C$_{24}$H$_{33}$N$_3$O, fumarate: % Calc: C, 67.86; H, 7.52; N, 8.48; % obtained: C, 67.51; H, 7.44; N, 8.19.

EXAMPLE 39

(±)-N-[3-{4-(2,5-dimethylphenyl)-1-piperazinyl}-propyl]-α-hydroxymethyl-benzeneacetamide, monohydrochloride, 0.5 H$_2$O (Compound 39)

Compound 39 is prepared in a similar manner to that of Example 20 except that (±)-tropic acid is used in place of diphenylacetic acid; M.p.: 168–169° C.

NMR-$^1$H (400 MHz, DMSO d6, δ): 10.77 (bs, 1H, $^+$NH); 8.34 (m, 1H, NH—CO); 7.28 (m, 5H, Ph); 7.06 (d, 1H, P$\underline{h}$—CH$_3$, J=7.6 Hz); 6.82 (m, 2H, P$\underline{h}$—CH$_3$); 4.48 (bs, 1H, OH); 3.96 (m, 1H, CH); 3.61 (m, 1H, ½ C$\underline{H_2}$—OH); 3.53 (m, 1H, ½ C$\underline{H_2}$—OH); 3.45 (m, 2H, $^+$NH—C$\underline{H_2}$); 3.17 (m, 2H, C$\underline{H_2}$—NH—CO) 3.10 (m, 10H, piperazine); 2.26 (s, 3H, P$\underline{h}$—CH$_3$); 2.20 (s, 3H, Ph—C$\underline{H_3}$); 1.87 (m, 2H, CH$_2$).

Elemental analysis for C$_{24}$H$_{33}$N$_3$O$_2$, HCl, 0.5 H$_2$O: % Calc: C, 65.36; H, 8.00; N, 9.53; % obtained: C, 65.72; H, 7.85; N, 9.31.

EXAMPLE 40

(±)-N-[3-{4-(2,5-dimethylphenyl)-1-piperazinyl}-propyl]-α-hydroxy-α-methyl-4-methoxy-benzeneacetamide, 1.25 fumarate, 0.6 H$_2$O
(Compound 40)

40.1) Ethyl-ester of (±)-α-hydroxy-α-methyl-4-methoxy-benzeneacetic acid:

Intermediate 40.1 is prepared in a similar manner to that of intermediate 31.1 except that 4-bromoanisole is used in place of 3-bromochlorobenzene.

NMR-$^1$H (100 MHz, CDCl$_3$, δ): 7.51–6.82 (m, 4H, Ph); 4.25 (q, 2H, CH$_2$, J=7.0 Hz); 3.81 (s, 3H, OCH$_3$); 3.65 (s, 1H, OH); 1.82 (s, 3H, CH$_3$); 1.30 (t, 3H, CH$_2$—C$\underline{H_3}$).

40.2) (±)-α-hydroxy-α-methyl-4-methoxy-benzeneacetic acid:

Intermediate 40.2 is prepared in a similar manner to that of intermediate 31.2 except that the ethyl-ester of (±)-α-hydroxy-α-methyl-4-methoxy-benzeneacetic acid is used in place of the ethyl-ester of (±)-3-chloro-α-hydroxy-α-methyl-benzeneacetic acid; M.p.: 129–130° C.

NMR-$^1$H (100 MHz, CDCl$_3$, δ): 7.52–6.85 (m, 4H, Ph); 4.70 (bs, 2H, OH+CO$_2$H); 3.81 (s, 3H, OCH$_3$); 1.75 (s, 3H, CH$_3$).

40.3) (±)-N-[3-{4-(2,5-dimethylphenyl)-1-piperazinyl}-propyl]-α-hydroxy-α-methyl-4-methoxy-benzeneacetamide, 1.25 fumarate, 0.6 H$_2$O:

Compound 40 is prepared in a similar manner to that of Example 20 except that (±)-α-hydroxy-α-methyl-4-methoxy-benzeneacetic acid is used in place of diphenylacetic acid; M.p.: 90–91° C.

NMR-$^1$H (400 MHz, DMSO d6, δ): 8.12 (m, 1H, NH—CO); 7.45 (d, 2H, P$\underline{h}$—OCH$_3$, J=8.7 Hz); 7.06 (d, 1H, P$\underline{h}$—CH$_3$, J=7.57 Hz); 6.86 (d, 2H, P$\underline{h}$—OCH$_3$); 6.81 (s, 1H, P$\underline{h}$—CH$_3$); 6.76 (d, 1H, P$\underline{h}$—CH$_3$); 6.60 (s, 2.5H, 1.25 —CH=CH—); 3.71 (s, 3H, OCH$_3$); 3.10 (m, 2H, C$\underline{H_2}$—NHCO); 2.86 (bs, 4H, piperazine); 2.59 (bs, 4H, piperazine); 2.41 (m, 2H, CH$_2$—N); 2.24 (s, 3H, Ph—C$\underline{H_3}$); 2.17 (s, 3H, Ph—CH$_3$); 1.59 (m, 5H, CH$_2$, CH$_3$).

Elemental analysis for C$_{25}$H$_{35}$N$_3$O$_3$, 1.25 fumarate, 0.6 H$_2$O: % Calc: C, 61.97; H. 7.14; N, 7.23; % obtained: C, 62.41; H, 7.02; N, 7.22.

EXAMPLE 41

(±)-N-[3-{4-(2,5-dimethylphenyl)-1-piperazinyl}-α-hydroxy-α-methyl-4-methyl-benzeneacetamide, dihydrochloride (Compound 41)

41.1) Ethyl-ester of (±)-α-hydroxy-α-methyl-4-methyl-benzeneacetic acid:

Intermediate 41.1 is prepared in a similar manner to that of intermediate 31.1 except that 4-bromotoluene is used in place of 3-bromochlorobenzene.

NMR-$^1$H (100 MHz, CDCl$_3$, δ): 7.51–7.11 (m, 4H, Ph); 4.24 (q, 2H, C$\underline{H_2}$—CH$_3$, J=7.0 Hz); 3.78 (s, 1H, OH); 2.40 (s, 3H, Ph—C$\underline{H_3}$); 1.75 (s, 3H, CH$_3$); 1.30 (t, 3H, CH$_2$—C$\underline{H_3}$).

41.2) (±)-α-hydroxy-α-methyl-4-methyl-benzeneacetic acid:

Intermediate 41.2 is prepared in a similar manner to that of intermediate 31.2 except that the ethyl-ester of (±)-α-hydroxy-α-methyl-4-methyl-benzeneacetic acid is used in place of the ethyl-ester of (±)-3-chloro-α-hydroxy-α-methyl-benzeneacetic acid; M.p.: 105–106° C.

NMR-$^1$H (100 MHz, CDCl$_3$, δ): 7.55–7.15 (m, 4H, Ph); 4.80 (bs, 2H, OH+CO$_2$H); 2.41 (s, 3H, Ph—C$\underline{H_3}$); 1.81 (s, 3H, CH$_3$).

41.3) (±)-N-[3-{4-(2,5-dimethylphenyl)-1-piperazinyl}-propyl]-α-hydroxy-α-methyl-4-methyl-benzeneacetamide, dihydrochloride:

Compound 41 is prepared in a similar manner to that of Example 20 except that (±)-α-hydroxy-α-methyl-4-methyl-benzeneacetic acid is used in place of diphenylacetic acid; M.p.: 145–147° C.

NMR-$^1$H (400 MHz, DMSO d6, δ): 10.93 (bs, 1H, $^+$NH); 8.12 (m, 1H, NH—CO); 7.42 (d, 2H, P$\underline{h}$—C(OH), J=8 Hz); 7.20 (d, 2H, P$\underline{h}$—C(OH)); 7.06 (d, 1H, P$\underline{h}$—CH$_3$, J=7.9 Hz); 6.82 (m, 2H, P$\underline{h}$—CH$_3$); 5.23 (bs, OH); 3.41 (m, 2H, $^+$NH—C$\underline{H_2}$); 3.10 (m, 10H, piperazine+C$\underline{H_2}$—HNCO); 2.26 (s, 6H, 2×Ph—C$\underline{H_3}$); 2.20 (s, 3H, Ph—C$\underline{H_3}$); 1.86 (m, 2H, CH$_2$); 1.61 (s, 3H, CH$_3$).

Elemental analysis for C$_{25}$H$_{35}$N$_3$O$_2$, 2 HCl: % Calc: C, 62.23; H, 7.73; N, 8.71; % obtained: C, 62.24; H, 7.94; N, 8.76.

EXAMPLE 42

(±)-N-[3-{4-(2,5dimethylphenyl)-1-piperazinyl}-propyl]-α-hydroxy-α-methyl-1-naphthaleneacetamide, fumarate (Compound 42)

42.1) Ethyl-ester of (+)-α-hydroxy-α-methyl-1-naphthaleneacetic acid:

Intermediate 42.1 is prepared in a similar manner to that of intermediate 31.1 except that 1-bromonaphthalene is used in place of 3-bromochlorobenzene.

NMR-$^1$H (100 MHz, CDCl$_3$, δ): 8.30–7.35 (m, 7H, naphthalene); 4.19 (q, 2H, CH$_2$, J=7 Hz); 3.69 (s, 1H, OH); 2.01 (s, 3H, CH$_3$); 1.09 (t, 3H, CH$_2$—C$\underline{H_3}$).

42.2) (±)-α-hydroxy-α-methyl-1-naphthaleneacetic acid:

Intermediate 42.2 is prepared in a similar manner to that of intermediate 31.2 except that the ethyl-ester of (±)-α-hydroxy-α-methyl-1-naphthaleneacetic acid is used in place of the ethyl-ester of (±)-3-chloro-α-hydroxy-α-methyl-benzeneacetic acid; M.p.: 152–153° C.

NMR-$^1$H (100 MHz, CD$_3$OD, δ): 8.54 (m, 1H, naphthalene); 8.10–7.50 (m, 6H, naphthalene); 2.18 (s, 3H, CH$_3$).

42.3) (±)-N-[3-{4-(2,5-dimethylphenyl)-1-piperazinyl}-propyl]-α-hydroxy-α-methyl-1-naphthaleneacetamide, fumarate:

Compound 42 is prepared in a similar manner to that of Example 20 except that (±)-α-hydroxy-α-methyl-1-naphthaleneacetic acid is used in place of diphenylacetic acid; M.p.: 136–137° C.

NMR-$^1$H (400 MHz, DMSO d6, δ): 8.41 (d, 1H, naphthalene); 8.29 (m, 1H, NH—CO); 7.89 (d, 1H, naphthalene, J=7.39 Hz); 7.84 (d, 1H, naphthalene, J=8.10 Hz); 7.63 (d, 1H, naphthalene, J=7.21 Hz); 7.45 (m, 3H, naphthalene); 7.01 (d, 1H, P$\underline{h}$—CH$_3$, J=7.52 Hz); 6.79 (s, 1H, P$\underline{h}$—CH$_3$); 6.74 (d, 1H, P$\underline{h}$—CH$_3$); 6.60 (s, 2H, —CH═CH—); 6.25 (bs, 1H, OH; 3.19 (m, 2H, C$\underline{H_2}$—NHCO); 2.84 (bs, 4H, piperazine); 2.56 (bs, 4H, piperazine); 2.43 (m, 2H, CH$_2$—N); 2.22 (s, 3H, Ph—C$\underline{H_3}$); 2.17 (s, 3H, Ph—C$\underline{H_3}$); 1.83 (s, 3H, CH$_3$); 1.66 (m, 2H, CH$_2$).

Elemental analysis for C$_{28}$H$_{35}$N$_3$O$_2$, fumarate: % Calc: C, 68.43; H, 7.00; N, 7.48; % obtained: C, 68.58; H, 7.16; N, 7.53.

EXAMPLE 43

(±)-N-[3-{4-(2,5-dimethylphenyl)-1-piperazinyl}-propyl]-α-hydroxy-α-methyl-2-naphthaleneacetamide, 0.75 fumarate (Compound 43)

43.1) Ethyl-ester of (±)-α-hydroxy-α-methyl-2-naphthaleneacetic acid:

Intermediate 43.1 is prepared in a similar manner to that of intermediate 31.1 except that 2-bromonaphthalene is used in place of 3-bromochlorobenzene.

NMR-$^1$H (100 MHz, CDCl$_3$, δ): 8.10–7.40 (m, 7H, naphthalene); 4.25 (q, 2H, CH$_2$, J=7 Hz); 3.95 (s, 1H, OH); 1.90 (s, 3H, CH$_3$); 1.29 (t, 3H, CH$_2$—C$\underline{H_3}$).

43.2) (±)-α-hydroxy-α-methyl-2-naphthaleneacetic acid:

Intermediate 43.2 is prepared in a similar manner to that of intermediate 31.2 except that the ethyl-ester of (±)-α-hydroxy-α-methyl-2-naphthaleneacetic acid is used in place of the ethyl-ester of (±)-3-chloro-α-hydroxy-α-methyl-benzeneacetic acid, M.p.: 169–170° C.

NMR-$^1$H (100 MHz, CD$_3$OD, δ): 8.75–7.56 (m, 7H, naphthalene); 2.05 (s, 3H, CH$_3$).

43.3) (±)-N-[3-{4-(2,5-dimethylphenyl)-1-piperazinyl}-propyl]-α-hydroxy-α-methyl-2-naphthaleneacetamide, 0.75 fumarate:

Compound 43 is prepared in a similar manner to that of Example 20 except that (±)-α-hydroxy-α-methyl-2-naphthaleneacetic acid is used in place of diphenylacetic acid; M.p.: 132–133° C.

NMR-$^1$H (400 MHz, DMSO d6, δ): 8.17 (m, 1H, NH—CO); 8.03 (s, 1H, naphthalene); 7.89 (m, 3H, naphthalene); 7.71 (dd, 1H, naphthalene, J$_{12}$=8.60 Hz, J$_{13}$=1.42 Hz); 7.47 (m, 2H, naphthalene) 7.02 (d, 1H, P$\underline{h}$—CH$_3$, J=7.57 Hz); 6.80 (s, 3H, P$\underline{h}$—CH$_3$); 6.76 (d, 1H, P$\underline{h}$—CH$_3$); 6.61 (s, 1.5H, 0.75×—CH═CH—); 3.12 (m, 2H, C$\underline{H_2}$—NHCO); 2.82 (bs, 4H, piperazine); 2.54 (bs, 4H, piperazine); 2.39 (m, 2H, CH$_2$—N); 2.24 (s, 3H, Ph—C$\underline{H_3}$) 2.16 (s, 3H, Ph—C$\underline{H_3}$); 1.73 (s, 3H, CH$_3$); 1.16 (m, 2H, CH$_2$).

Elemental analysis for C$_{28}$H$_{35}$N$_3$O$_2$, 0.75 fumarate: % Calc: C, 69.90; H, 7.19; N, 7.89; % obtained: C, 69.64; H, 7.12; N, 7.56.

EXAMPLE 44

(±)-N-[3-{4-(2,5-dimethylphenyl)-1-piperazinyl}-propyl]-α-hydroxy-α-methyl-1,1'-biphenyl-3-acetamide, fumarate (Compound 44)

44.1) Ethyl-ester of (±)-α-hydroxy-α-methyl-1,1'-biphenyl-3-acetic acid:

Intermediate 44.1 is prepared in a similar manner to that of intermediate 31.1 except that 3-bromobiphenyl is used in place of 3-bromochlorobenzene.

NMR-$^1$H (100 MHz, CDCl$_3$, δ): 7.80–7.35 (m, 9H, biphenyl); 4.25 (q, 2H, CH$_2$, J=7.0 Hz); 3.83 (s, 1H, OH); 1.81 (s, 3H, CH$_3$); 1.29 (t, 3H, CH$_2$—C$\underline{H_3}$).

44.2) (±)-α-hydroxy-α-methyl-1,1'-biphenyl-3-acetic acid:

Intermediate 44.2 is prepared in a similar manner to that of intermediate 31.2 except that the ethyl-ester of (±)-α-hydroxy-α-methyl-1,1'-biphenyl-3-acetic acid is used in place of the ethyl-ester of (±)3-chloro-α-hydroxy-α-methyl-benzeneacetic acid; M.p.: 118–119° C.

NMR-$^1$H (100 MHz, CDCl$_3$, δ): 7.82–7.35 (m, 9H, biphenyl); 6.20 (bs, 2H, OH, CO$_2$H); 1.90 (s, 3H, CH$_3$).

44.3) (±)-N-[3-{4-(2,5-dimethylphenyl)-1-piperazinyl}-propyl]-α-hydroxy-α-methyl-1,1'-biphenyl-3-acetamide, fumarate Compound 44 is prepared in a similar manner to that of Example 20 except that (±)-α-hydroxy-α-methyl-1,1'-biphenyl-3-acetic acid is used in place of diphenylacetic acid; M.p.: 90–91° C.

NMR-$^1$H (400 MHz, DMSO d6, δ): 8.19 (m, 1H, NH—CO); 7.83 (s, 1H, biphenyl); 7.63–7.34 (m, 8H, biphenyl); 7.02 (d, 1H, Ph—CH$_3$, J=7.54 Hz); 6.79 (s, 1H, Ph—CH$_3$); 6.75 (d, 1H, Ph—CH$_3$); 6.61 (s, 2H, —CH=CH—); 3.12 (m, 2H, CH$_2$—NHCO); 2.89 (bs, 4H, piperazine); 2.50 (bs, 4H, piperazine); 2.39 (m, 2H, CH$_2$—N); 2.23 (s, 3H, Ph—CH$_3$); 2.15 (s, 3H, Ph—CH$_3$); 1.68 (s, 3H, CH$_3$); 1.16 (m, 2H, CH$_2$).

Elemental analysis for C$_{30}$H$_{37}$N$_3$O$_2$, fumarate: % Calc: C, 69.49; H, 7.03; N, 7.15; % obtained: C, 69.65; H, 6.94; N, 7.38.

EXAMPLE 45

S-(+)-N-[3-{4-(2,5-dimethylphenyl)-1-piperazinyl}-propyl]-α-hydroxy-α-methyl-benzeneacetamide, fumarate (Compound 45)

Compound 45 is prepared in a similar manner to that of Example 20 except that S-(+)-atrolactic acid is used in place of diphenylacetic acid; M.p.: 190–191° C. ([α]D=+10.75 (c=0.12, EtOH temp=20° C.)).

NMR-$^1$H (400 MHz, DMSO d6, δ): 8.09 (m, 1H, NH—CO); 7.53 (m, 2H, Ph) 7.31 (m, 2H, Ph); 7.22 (m, 1H, Ph); 7.02 (d, 1H, Ph—CH$_3$, J=7.57 Hz); 6.81 (s, 1H, Ph—CH$_3$); 6.76 (d, 1H, Ph—CH$_3$); 6.60 (s, 2H, —CH=CH—); 3.10 (m, 2H, CH$_2$—NHCO) 2.86 (bs, 4H, piperazine); 2.58 (bs, 4H, piperazine); 2.41 (m, 2H, CH$_2$—N); 2.24 (s, 3H, Ph—CH$_3$); 2.17 (s, 3H, Ph—CH$_3$); 1.61 (s, 3H, CH$_3$); 1.59 (m, 2H, CH$_2$).

Elemental analysis for C$_{24}$H$_{33}$N$_3$O$_2$, fumarate: % Calc: C, 65.73; H, 7.29; N, 8.21; % obtained: C, 65.78; H, 7.51; N, 8.07.

EXAMPLE 46

R-(−)-N-[3-{4-(2,5-dimethylphenyl)-1-piperazinyl}-propyl]-α-hydroxy-α-methyl-benzeneacetamide, 0.8 fumarate (Compound 46)

Compound 46 is prepared in a similar manner to that of Example 20 except that R-(−)-atrolactic acid is used in place of diphenylacetic acid, M.p.: 190–191° C. ([α]D=−7.25 (c=0.10, EtOH temp=20° C.)).

Elemental analysis for C$_{24}$H$_{33}$N$_3$O$_2$, 0.8 fumarate: % Calc: C, 66.89; H, 7.47; N, 8.60; % obtained: C, 66.43; H, 7.25; N, 8.56.

EXAMPLE 47

(±)-N-[3-{4-(2,5-dimethylphenyl)-1-piperazinyl}-propyl]-α-benzylaminocarbonyl-benzeneacetamide, fumarate (Compound 47)

47.1) Benzyl-ester of (±)-α-benzylaminocarbonyl-benzeneacetic acid:

4.05 g (15 mmol) of the monobenzyl-ester of phenylmalonic acid, 1.64 ml (15 mmol) of benzylamine and 2.23 g (16.5 mmol) of hydroxybenzotriazole are dissolved in 40 ml of dichloromethane. After cooling down to 0–5° C., 3.4 g (16.5 mmol) of dicyclohexylcarbodiimide is added in one go, and agitation is carried out at 20° C. for 4 hours. The white precipitate formed during the reaction is filtered out, and the filtrate is successively rinsed with 1N NaOH (2×50 ml) and a saturated solution of sodium chloride (50 ml). After drying over sodium sulphate, the solvent is evaporated off, and the residue is precipitated in the presence of dichloromethane. A filtration produced 3.19 g (59%) of a white powder; M.p.: 150–151° C.

NMR-$^1$H (100 MHz, CD$_3$OD, δ): 7.70–7.35 (m, 15H, Ph); 5.35 (s, 2H, CH$_2$—O); 5.05 (s, 1H, CH); 4.51 (d, 2H, CH$_2$—N).

47.2) (±)-α-benzylaminocarbonyl-benzeneacetic acid:

1 g (2.78 mmol) of the benzyl-ester of (±)-α-benzylaminocarbonyl-benzeneacetic acid dissolved in a mixture of 40 ml of ethanol and 30 ml of acetic acid and 200 mg of 10% Pd/C are introduced into a Parr flask. Hydrogenation is carried out under 15 PSI H$_2$ at 30° C. After agitation for 15 hours, the mixture is filtered through Celite, and the filtrate is concentrated under reduced pressure. The residue is fractionated between 30 ml of diethylether and 30 ml of a saturated solution of NaHCO$_3$. The aqueous extract is decanted and rinsed with 30 ml of diethylether. After acidification with 3N HCl at 0° C., the aqueous phase is extracted with 2×30 ml of diethylether. The ethereal solution is dried over sodium sulphate, filtered, and the solvent evaporated off in order to produce 451 mg (60%) of a white powder; M.p.: 132–133° C.

NMR-$^1$H (100 MHz, CD$_3$OD, δ): 7.70–7.35 (m, 10H, Ph); 4.80 (s, 1H, CH); 4.57 (m, 2H, CH$_2$—N).

47.3) (±)-N-[3-{4-(2,5-dimethylphenyl)-1-piperazinyl}-propyl]-α-benzylaminocarbonyl-benzeneacetamide, fumarate:

Compound 47 is prepared in a similar manner to that of Example 20 except that (±)-α-benzylaminocarbonyl-benzeneacetic acid is used in place of diphenylacetic acid; M.p.: 90–91° C.

NMR-$^1$H (400 MHz, DMSO d6, δ): 8.69 (m, 1H, NH—CH$_2$Ph); 8.26 (m, 1H, NH—CO); 7.32 (m, 10H, 2×Ph); 7.02 (d, 1H, Ph—CH$_3$, J=7.51 Hz); 6.80 (s 1H, Ph—CH$_3$); 6.76 (d, 1H, Ph—CH$_3$); 6.61 (s, 2H, —CH=CH—); 4.47 (s, 1H, CH); 4.31 (m, 2H, NH—CH$_2$—Ph); 3.15 (m, 2H, CH$_2$—NHCO); 2.83 (bs, 4H, piperazine); 2.58 (bs, 4H, piperazine); 2.42 (m, 2H, CH$_2$—N); 2.23 (s, 3H, Ph—CH$_3$) 2.17 (s, 3H, Ph—CH$_3$); 1.63 (m, 2H, CH$_2$).

Elemental analysis for C$_{31}$H$_{38}$N$_4$O$_2$, fumarate: % Calc: C, 68.38; H, 6.89; N, 9.11; % obtained: C, 68.70; H, 7.06; N, 8.81.

EXAMPLE 48

(±)-N-[3-{4-(2,5-dimethylphenyl)-1piperazinyl}-propyl]-α-(4-methylphenyl)-sulphonylamino-benzeneacetamide, 1.5 HCl, 0.5 H$_2$O (Compound 48)

48.1) (±)-(4-methylphenyl)-sulphonylamino-benzeneacetic acid:

Intermediate 48.1 is prepared in a similar manner to that of intermediate 33.1 except that p-toluenesulphonyl chloride is used in place of methanesulphonyl chloride; M.p.: 188–189° C.

NMR-$^1$H (100 MHz, CD$_3$OD, δ): 7.65 (m, 4H, p-toluene); 7.42 (s, 5H, Ph); 5.09 (d, 1H, CH); 2.55 (s, 3H, CH$_3$).

48.2) (±)-N-[3-{4-(2,5-dimethylphenyl)-1-piperazinyl}-propyl]-α-(4-methylphenyl)sulphonylamino-benzeneacetamide, 1.5 HCl, 0.5 H$_2$O:

Compound 48 is prepared in a similar manner to Example 20 except that (±)-(4-methylphenyl)-sulphonylamino-benzeneacetic acid is used in place of diphenylacetic acid; M.p.: 180–181° C.

NMR-$^1$H (400 MHz, DMSO d6, δ): 11.19 (bs, 1H, $^+$NH); 8.54 (m, 2H, NH—CO, NH—SO$_2$); 7.63 (m, 2H, Ph—SO$_2$); 7.26 (m, 7H, Ph—SO$_2$, Ph); 7.06 (d, 1H, Ph—CH$_3$, J=7.05 Hz); 6.83 (bs, 2H, Ph—CH$_3$); 4.92 (d, 1H, CH, J=8.80 Hz); 3.37 (m, 2H, $^+$NH—CH$_2$); 3.12 (bs, 4H, piperazine); 2.97 (m, 6H, piperazine, CH$_2$—NHCO); 2.35 (s, 3H, CH$_3$—PhSO$_2$); 2.26 (s, 3H, Ph—CH$_3$); 2.20 (s, 3H, Ph—CH$_3$); 1.77 (m, 2H, CH$_2$).

Elemental analysis for $C_{30}H_{38}N_4O_3S$, 1.5 HCl, 0.5 H$_2$O: % Calc: C, 60.21; H, 6.82; N, 9.36; S, 5.36; % obtained: C, 60.59; H, 6.81; N, 9.21; S, 5.69.

EXAMPLE 49

(±)-N-[3-{4-(2,5-dimethylphenyl)-1-piperazinyl}-propyl]-α-benzylcarbonylamino-benzeneacetamide, fumarate, 0.5 H$_2$O (Compound 49)

49.1) (±)-α-benzylcarbonylamino-benzeneacetic acid:

Intermediate 49.1 is prepared in a similar manner to that of intermediate 33.1 except that phenylacetyl chloride is used in place of methanesulphonyl chloride.

NMR-$^1$H (100 MHz, CDCl$_3$, δ): 8.80 (bs, 1H, CO$_2$H); 7.30 (bs, 10H, 2×Ph); 5.52 (d, 1H, NHCO, J=7.0 Hz); 3.60 (m, 3H, CH+CH$_2$).

49.2) (±)-N-[3-{4-(2,5-dimethylphenyl)-1-piperazinyl}-propyl]-α-benzylcarbonylamino-benzeneacetamide, fumarate, 0.5 H$_2$O:

Compound 49 is prepared in a similar manner to that of Example 20 except that (±)-α-benzylcarbonylamino-benzeneacetic acid is used in place of diphenylacetic acid; M.p.: 158–159° C.

NMR-$^1$H (400 MHz, DMSO d6, δ): 8.73 (d, 1H, CH—NH—CO, J=8.0 Hz); 8.32 (m, 1H, NH—CO); 7.42–7.20 (m, 10H, 2×Ph); 7.02 (d, 1H, Ph—CH$_3$, J=7.52 Hz); 6.80 (s, 1H, Ph—CH$_3$); 6.75 (d, 1H, Ph—CH$_3$); 6.61 (s, 2H, —CH═CH—); 5.43 (d, 1H, CH); 3.56 (s, 2H, CH$_2$—Ph); 3.10 (m, 2H, CH$_2$—NHCO); 2.80 (bs, 4H, piperazine); 2.50 (bs, 4H, piperazine); 2.34 (m, 2H, CH$_2$—N); 2.23 (s, 3H, Ph—CH$_3$); 2.17 (s, 3H, Ph—CH$_3$); 1.58 (m, 2H, CH$_2$).

Elemental analysis for $C_{31}H_{38}N_4O_2$, fumarate, 0.5 H$_2$O: % Calc: C, 67.40; H, 6.95; N, 8.98; % obtained: C, 67.57; H, 6.86; N, 8.98.

EXAMPLE 50

(±)-N-[3-{4-(2,5-dimethylphenyl)-1-piperazinyl}-propyl]-α-benzylaminocarbonyl-α-methyl-benzeneacetamide, fumarate, 0.5 H$_2$O (Compound 50)

50.1) Diethyl-ester of (±)-α-methyl-phenylmalonic acid:

Intermediate 50.1 is prepared in a similar manner to that of Example 11 except that the diethyl-ester of phenylmalonic acid is used in place of (±)-N-[3-{4-(2,5-dimethylphenyl)-1-piperazinyl}-propyl]-α-hydroxy-α-phenyl-benzeneacetamide.

NMR-$^1$H (100 MHz, CDCl$_3$, δ): 7.39 (bs, 5H, Ph); 4.28 (q, 4H, OCH$_2$, J=7.0 Hz); 1.88 (s, 3H, CH$_3$); 1.26 (t, 3H, CH$_2$—CH$_3$).

50.2) Monoethyl-ester of (±)-α-methyl-phenylmalonic acid

Intermediate 50.2 is prepared in a similar manner to intermediate 31.2 except that the diethyl-ester of (±)-α-methyl-phenylmalonic acid is used in place of the ethyl-ester of (±)-3-chloro-α-hydroxy-α-methyl-benzeneacetic acid.

NMR-$^1$H (100 MHz, CDCl$_3$, δ): 9.38 (bs, 1H, CO$_2$H); 7.38 (m, 5H, Ph); 4.25 (q, 2H, OCH$_2$, J=7.0 Hz); 1.90 (s, 3H, CH$_3$); 1.28 (t, 3H, CH$_2$—CH$_3$).

50.3) Ethyl-ester of (±)-α-benzylaminocarbonyl-α-methyl-benzeneacetic acid:

Intermediate 50.3 is prepared in a similar manner to that of intermediate 47.1 except that the monoethyl-ester of (±)-α-methyl-phenylmalonic acid is used in place of the monobenzyl-ester of phenylmalonic acid.

NMR-$^1$H (100 MHz, CDCl$_3$, δ): 7.30 (s, 10H, 2×Ph); 6.82 (m, 1H, NH—CO); 4.48 (m, 2H, CH$_2$); 4.27 (q, 2H, OCH$_2$, J=7.0 Hz); 1.87 (s, 3H, CH$_3$); 1.26 (t, 3H, CH$_2$—CH$_3$).

50.4) (±)-α-benzylaminocarbonyl-α-methyl-benzeneacetic acid:

Intermediate 50.4 is prepared in a similar manner to that of intermediate 31.2 except that the ethyl-ester of (±)-α-benzylaminocarbonyl-α-methyl-benzeneacetic acid is used in place of the ethyl-ester of (±)-3-chloro-α-hydroxy-α-methyl-benzeneacetic acid.

NMR-$^1$H (100 MHz, CDCl$_3$, δ): 7.25 (m, 10H, 2×Ph); 6.26 (m, 1H, NH—CO); 4.45 (m, 2H, CH$_2$); 1.95 (s, 3H, CH$_3$).

50.5) (±)-N-[3-{4-(2,5-dimethylphenyl)-1-piperazinyl}-propyl]-α-benzylaminocarbonyl-α-methyl-benzeneacetamide, fumarate, 0.5 H$_2$O:

Compound 50 is prepared in a similar manner to that of Example 20 except that (±)-α-benzylaminocarbonyl-α-methyl-benzeneacetic acid is used in place of diphenylacetic acid M.p.: 159–160° C.

NMR-$^1$H (400 MHz, DMSO d6, δ): 8.40 (m, 1H, PhCH$_2$—NH—CO); 7.93 (m, 1H, NH—CO); 7.26 (m, 10H, 2×Ph); 7.02 (d, 1H, Ph—CH$_3$, J=7.52 Hz); 6.79 (s, 1H, Ph—CH$_3$); 6.75 (d, 1H, Ph—CH$_3$); 6.61 (s, 2H, —CH═CH—); 4.33 (d, 2H, CH$_2$—Ph, J=5.85 Hz); 3.19 (m, 2H, CH$_2$—NHCO); 2.79 (bs, 4H, piperazine); 2.54 (bs, 4H, piperazine); 2.39 (m, 2H, CH$_2$—N); 2.24 (s, 3H, Ph—CH$_3$); 2.17 (s, 3H, Ph—CH$_3$); 1.71 (s, 3H, CH$_3$); 1.63 (m, 2H, CH$_2$).

Elemental analysis for $C_{32}H_{40}N_4O_2$, fumarate, 0.5 H$_2$O: % Calc: C, 67.80; H, 7.11; N, 8.78; % obtained: C, 68.20; H, 7.08; N, 8.91.

EXAMPLE 51

(±)-N-[3-{4-(2,5-dimethylphenyl)-1-piperazinyl}-propyl]-α-methoxy-α-methyl-benzeneacetamide, 0.5 fumarate (Compound 51)

Compound 51 is prepared in a similar manner to that of Example 11 except that (±)-N-[3-{4-(2,5-dimethylphenyl)-1-piperazinyl}-propyl]-α-hydroxy-α-methyl-benzeneacetamide is used in place of (±)-N-[3-{4-(2,5-dimethylphenyl)-1-piperazinyl}-propyl]-α-hydroxy-α-phenyl-benzeneacetamide; M.p.: 172.5–173.5° C.

NMR-$^1$H (400 MHz, DMSO d6, δ): 8.16 (m, 1H, NH—CO); 7.35 (m, 5H, pH); 7.02 (d, 1H, Ph—CH$_3$, J=7.54 Hz); 6.80 (s, 1H, Ph—CH$_3$); 6.75 (d, 1H, Ph—CH$_3$); 6.60 (s, 1H, 0.5×—CH═CH—); 3.13 (m, 5H, CH$_2$—NHCO+OCH$_3$); 2.84 (bs, 4H, piperazine); 2.54 (bs, 4H, piperazine); 2.37 (m, 2H, CH$_2$—N); 2.23 (s, 3H, Ph—CH$_3$); 2.18 (s, 3H, Ph—CH$_3$); 1.64 (s, 3H, CH$_3$); 1.61 (m, 2H, CH$_2$).

Elemental analysis for $C_{25}H_{35}N_3O_2$, 0.5 fumarate: % Calc: C, 69.35; H. 7.98; N, 8.99; % obtained: C, 69.34; H, 7.99; N, 8.69.

EXAMPLE 52

(±)-N-[3-{4-(2,5-dimethylphenyl)-1-piperazinyl}-propyl]-α-benzyloxy-α-methyl-benzeneacetamide, 0.5 fumarate (Compound 52)

Compound 52 is prepared in a similar manner to that of Example 11 except that (±)-N-[3-{4-(2,5-dimethylphenyl)-1-piperazinyl}-propyl]-α-hydroxy-α-methyl-benzeneacetamide and benzyl bromide are used in place of (±)-N-[3-{4-(2,5-dimethylphenyl)-1-piperazinyl}-propyl]-α-hydroxy-α-phenyl-benzeneacetamide and methyl iodide; M.p.: 153–154° C.

NMR-$^1$H (400 MHz, DMSO d6, δ): 7.94 (m, 1H, NH—CO); 7.50–7.26 (m, 10H, 2×Ph); 7.00 (d, 1H, Ph—CH$_3$, J=7.46 Hz); 6.74 (d, 1H, Ph—CH$_3$); 6.71 (s, 1H, Ph—CH$_3$); 6.61 (s, 1H, 0.5×—CH=CH—); 4.35 (AB, 2H, CH$_2$—Ph, J$_{AB}$=12.25 Hz); 3.17 (m, 2H, CH$_2$—NHCO); 2.73 (bs, 4H, piperazine); 2.50 (bs, 4H, piperazine); 2.34 (m, 2H, CH$_2$—N); 2.22 (s, 3H, Ph—CH$_3$) 2.15 (s, 3H, Ph—CH$_3$); 1.74 (s, 3H, CH$_3$); 1.61 (m, 2H, CH$_2$).

Elemental analysis for $C_{31}H_{39}N_3O_2$, 0.5 fumarate: % Calc: C, 72.90; H, 7.60; N, 7.73; % obtained: C, 73.01; H, 7.46; N, 7.27.

EXAMPLE 53

(±)-3,4-dichloro-N-[3-{4-(2,5-dimethylphenyl)-1-piperazinyl}-propyl]-α-hydroxy-α-methyl-benzeneacetamide, fumarate (Compound 53)

Compound 53 is prepared in a similar manner to that of Example 31 except that 1-bromo-3,4-dichlorobenzene is used in place of 3-bromochlorobenzene; M.p.: 174–175° C.

NMR-$^1$H (400 MHz, DMSO d6, δ): 8.19 (m, 1H, NH—CO); 7.73 (d, 1H, Ph—Cl, J=1.17 Hz); 7.59 (d, 1H, PhCl, J=8.44 Hz); 7.50 (dd, 1H, PhCl); 7.02 (d, 1H, Ph—CH$_3$, J=7.52 Hz); 6.81 (s, 1H, Ph—CH$_3$); 6.76 (d, 1H, Ph—CH$_3$); 6.60 (s, 2H, —CH=CH—); 3.10 (m, 2H, CH$_2$—NHCO); 2.85 (bs, 4H, piperazine); 2.56 (bs, 4H, piperazine); 2.38 (m, 2H, CH$_2$—N); 2.24 (s, 3H, Ph—CH$_3$); 2.17 (s, 3H, Ph—CH$_3$); 1.59 (m, 5H, CH$_3$+CH$_2$).

Elemental analysis for $C_{24}H_{31}Cl_2N_3O_2$, fumarate: % Calc: C, 57.93; H, 6.08; N, 7.24; % obtained: C, 57.99; H, 6.24; N, 7.03.

EXAMPLE 54

(±)-N-[3-{4-(2,5-dimethylphenyl)-1-piperazinyl}-propyl]-2-hydroxy-2-methyl-propionamide, fumarate (Compound 54)

Compound 54 is prepared in a similar manner to that of Example 20 except that 2-hydroxyisobutyric acid is used in place of diphenylacetic acid; M.p.: 150–151° C.

NMR-$^1$H (400 MHz, DMSO d6, δ): 7.85 (m, 1H, NH—CO); 7.02 (d, 1H, Ph—CH$_3$, J=7.52 Hz); 6.81 (s, 1H, Ph—CH$_3$); 6.76 (d, 1H, Ph—CH$_3$); 6.60 (s, 2H, —CH=CH—); 3.13 (m, 2H, CH$_2$—NHCO); 2.88 (bs, 4H, piperazine); 2.67 (bs, 4H, piperazine); 2.38 (m, 2H, CH$_2$—N); 2.24 (s, 3H, Ph—CH$_3$); 2.18 (s, 3H, Ph—CH$_3$); 1.66 (m, 2H, CH$_2$); 1.24 (s, 6H, 2×CH$_3$).

Elemental analysis for $C_{19}H_{31}N_3O_2$, fumarate: % Calc: C, 61.45; H, 7.85; N, 9.35; % obtained: C, 61.00; H, 7.89; N, 9.22.

EXAMPLE 55

(±)-N-[3-{4-(2-(cyclopropylhydroxymethyl)-phenyl)-1-piperazinyl}-propyl]-α-phenyl-benzeneacetamide, 1.25 fumarate, 0.5 H$_2$O (Compound 55)

Compound 55 is prepared in a similar manner to that of Example 36 except that cyclopropylmagnesium bromide is used in place of ethylmagnesium bromide; M.p.: 151–152° C.

NMR-$^1$H (400 Mz, DMSO d6, δ): 8.31 (m, 1H, NH—CO); 7.49–7.09 (m, 14H, 3×Ph); 6.61 (s, 2.5H, 1.25×—CH=CH—); 4.92 (s, 1H, Ph—CH); 4.51 (d, 1H, CH—(OH), J=6.71 Hz); 3.13 (m, 2H, CH$_2$—NHCO); 3.00 (bs, 2H, piperazine); 2.72 (bs, 2H, piperazine); 2.58 (bs, 4H, piperazine); 2.41 (m, 2H, CH$_2$—N); 1.63 (m, 2H, CH$_2$); 1.05 (m, 1H, CH); 0.36 (m, 4H, cyclopropane).

Elemental analysis for $C_{31}H_{37}N_3O_2$, 1.25 fumarate, 0.5 H$_2$O: % Calc: C, 67.80; H, 6.80; N, 6.59; % obtained: C, 68.21; H, 6.82; N, 6.12.

EXAMPLE 56

(±)-N-[3-{4-(2-(propyl)-phenyl)-1-piperazinyl}-propyl]-α-hydroxy-α-phenyl-benzeneacetamide, 0.75 fumarate (Compound 56)

56.1) (Z,E)-1-benzyl-4-[2-(1-propenyl)-phenyl]-piperazine: 5.7 g (15.3 mmol) of ethyltriphenylphosphonium bromide is intoduced into an anhydrous three-necked flask provided with a nitrogen supply and containing 80 ml of dry THF. 8.45 ml (16.9 mmol) of a solution of phenyllithium (2 M in cyclohexane/diethylether: 7.3) is added dropwise to this mixture at 20° C. Agitation is continued for one hour and a solution of 4.3 g (15.3 mmol) of intermediate 36.1 in 30 ml of dry THF is added dropwise to this dark red mixture, cooled down to 0° C. After agitation overnight, the precipitate is filtered and rinsed with ethyl acetate. The filtrate is concentrated under vacuum, and the oily brown residue is subjected to chromatography on silica gel (eluant: light oil (bp. 40–65° C.)/ethyl acetate: 90/10) in order to produce 2.71 g (60%) of a light yellow pure oil.

NMR-$^1$H (100 MHz, CDCl$_3$, δ): 7.45–6.90 (m, 9H, 2×Ph); 6.60 (m, 1H, Ph—CH=CH—), 6.20 (m, ½ CH, ½×Ph—CH=CH—); 5.79 (m, ½ CH, ½×Ph—CH=CH—); 3.60 (m, 2H, CH$_2$—Ph); 3.00 (m, 4H, piperazine); 2.60 (m, 4H, piperazine); 1.90 (m, 3H CH$_3$).

56.2) 1-[2-(1-propenyl)-phenyl]-piperazine:

A mixture of 2.71 g (9.3 mmol) of (Z,E)-1-benzyl-4-[2-(1-propenyl)-phenyl]-piperazine and 100 mg of 10% Pd/C in 30 ml of ethanol is hydrogenated under 40 PSI H$_2$ at 40° C. for 15 hours in a Parr apparatus. Then the rection mixture is filtered on a layer of Celite, and the solvent is evaporated off under reduced pressure in order to produce 1.78 g (94%) of a white powder; M.p.: 145–146° C.

NMR-$^1$H (100 MHz, CDCl$_3$, δ): 7.18 (m, 4H, Ph); 4.55 (bs, NH); 3.30–2.90 (m, 8H, piperazine); 2.60 (m, 2H, CH$_2$—Ph); 1.68 (m, 2H, CH$_2$) 1.00 (t, 3H, CH$_3$, J=7.0 Hz).

56.3) (±)-N-[3-{4-(2-(propyl)-phenyl)-1-piperazinyl}-propyl]-α-hydroxy-α-phenyl-benzeneacetamide, 0.75 fumarate:

Compound 56 is prepared in a similar manner to that of Example 1 except that (±)-1-[2-(1-propenyl)-phenyl]-piperazine is used in place of 1-(3-methylphenyl)-piperazine; M.p.: 152–153° C.

NMR-$^1$H (400 MHz, DMSO d6, δ): 8.37 (m, 1H, NH—CO); 7.40–6.99 (m, 14H, 3×Ph); 6.60 (s, 1.5H, 0.75x—CH=CH—); 3.20 (m, 2H, CH$_2$—NHCO); 2.84 (m, 4H, piperazine); 2.59 (m, 6H, piperazine+Ph—CH$_2$); 2.44 (m, 2H, CH$_2$—N); 1.67 (m, 2H, CH$_2$); 1.60 (m, 2H, CH$_2$—CH$_3$); 0.92 (t, 3H, CH$_3$, J=7.46 Hz).

Elemental analysis for C$_{30}$H$_{37}$N$_3$O$_2$, 0.75 fumarate: % Calc: C, 70.94; H, 7.22; N, 7.52; % obtained: C, 70.71; H, 7.28; N, 7.07.

Test of the bond to the $\alpha_1$-adrenergic receptor:

The affinity of the various compounds of the invention for the $\alpha_1$-adrenergic receptors is determined by measuring the inhibition of the bond of [$^3$H]prazosin (DuPont NEN, Les Ulis, France) to the cerebral cortex of the rat according to a method derived from that of Morrow and Creese, Mol. Pharmacol. 29:321 (1986). The cerebral cortices of male Sprague Dawley rats are homogenized at 4° C. in Tris-HCl 50 mM pH=7.7 and centrifuged at 50,000 g for 30 minutes at 4° C. The pellets are again suspended in the same buffer and centrifuged again at 50,000 g for 30 minutes at 4° C.

The competitive inhibition of the bond of 0.2 nM [$^3$H] prazosin is carried out in triplicate with non-labelled test compounds of the invention in concentrations varying from 10$^{-11}$M to 10$^{-2}$M. Membranes of the rat's cerebral cortex (5 mg (damp)/ml) are incubated for 30 minutes at 25° C. in Tris-HCl 50 mM, pH=7.7. The bound [$^3$H]prazosin is separated from the free [$^3$H]prazosin by immediate filtration through Whatman GF/B glass fibre filters using Brandel cell recuperators. The filters are rinsed three times with the same buffer at 0–4° C. and their radioactivity is tested by liquid scintillation spectrometry.

The specific bonds are obtained by subtracting the non-specific bonds (determined in the presence of 10 µM of phentolamine (Sigma Chemical Co. St. Louis Mo.)) from the total bonds. The data relative to the bonds is analyzed by computer assisted iterative non-linear regression analysis, using the Ligand program (Munson, P. J., Rodbard, D. Anal. Biochem. 107:220 (1980)).

The IC$_{50}$ (concentration necessary for the inhibition of 50% of the specific bonds) of each of the test compounds is given in Table I.

TABLE I

AFFINITY OF THE BOND OF THE $\alpha_1$ ADRENERGIC RECEPTOR

| Compound No. | Ki (nM) | Compound No. | Ki (nM) |
|---|---|---|---|
| 1 | 51 | 29 | 67 |
| 2 | 30 | 30 | 44 |
| 3 | 60 | 31 | 43 |
| 4 | 66 | 32 | 51 |
| 5 | 60 | 33 | 40 |
| 6 | 480 | 34 | 45 |
| 7 | 30 | 35 | 90 |
| 8 | 16 | 36 | 170 |
| 9 | 28 | 38 | 30 |
| 10 | 27 | 39 | 27 |
| 11 | 38 | 40 | 38 |
| 13 | 30 | 41 | 27 |
| 14 | 27 | 42 | 22 |
| 15 | 27 | 43 | 29 |
| 16 | 41 | 44 | 73 |
| 17 | 54 | 45 | 13 |
| 18 | 55 | 46 | 48 |
| 19 | 60 | 47 | 14 |
| 20 | 27 | 48 | 29 |
| 21 | 64 | 49 | 50 |
| 22 | 25 | 50 | 50 |
| 23 | 98 | 51 | 110 |
| 24 | 69 | 52 | 51 |
| 25 | 29 | 54 | 280 |

TABLE I-continued

AFFINITY OF THE BOND OF THE $\alpha_1$ ADRENERGIC RECEPTOR

| Compound No. | Ki (nM) | Compound No. | Ki (nM) |
|---|---|---|---|
| 26 | 74 | 55 | 300 |
| 27 | 31 | 56 | 25 |
| 28 | 36 | | |

Urethra Contraction Test:

The urethrae are removed from male New Zealand rabibits, and cleaned of the surrounding connective tissues. Bands of prostatic urethrae (3 mm wide, 10–15 mm long) are suspended (1 g tension) in organ baths containing 10 ml of physiological solution (pH 7.4) at 37° C. under an atmosphere of 95% O$_2$/5% CO$_2$; NaCl (118 mM); KCl (4.7 mM); CaCl$_2$ (2.5 mM); KH$_2$PO$_4$ (1.2 mM); MgSO$_4$ (1.2 mM); NaHCO$_3$ (25 mM); glucose (11 mM). The contractile responses are measured using force displacement transducers coupled to a Gould 8000S polygraph. A one hour period of equilibration or equalization is provided before the experiment. After equalization, the preparations are sensitized by a submaximal concentration of phenylephrine. Forty five minutes after the sensitization, a concentration-effect curve for the phenylephrine is established. In order to determine the effect of the test compounds, different preparations originating from the same animal are used in parallel. One preparation serves as a control whilst the others receive a concentration of a test compound introduced into the bath 30 minutes before the phenylephrine (Auguet, M. et al. European J. Pharmacol. 217:153 (1995)).

The dissociation constants (K$_b$) of the test compounds are determined using the following equation: K$_b$=[B]/(dose ratio—1); in which [B] is the concentration of test compound and (dose ratio) is the EC$_{50}$ of phenylephrine in the presence of the test compound divided by the EC$_{50}$ of the control preparation. These resultats are then expressed as the negative logarithm of K$_b$. The values of the EC$_{50}$ are calculated from the maximum contractile response to the phenylephrine by computer analysis using a linear regression over the average tension values. The maximum contractile response of each preparation which was subjected to the test compound is determined by comparing the response provoked by the application of the sensitizing concentration of phenylephrine with the response provoked in the control preparation (which has not received the test compounds).

The resultats obtained for the test compounds are given in Table II.

TABLE II

INHIBITION OF THE CONTRACTION OF THE URETHRA

| Compound N° | -log K$_b$ |
|---|---|
| 2 | 8 |
| 7 | 8.1 |
| 8 | 8.2 |
| 9 | 8.1 |
| 10 | 8.2 |
| 11 | 6.9 |
| 13 | 8.2 |
| 14 | 7.8 |
| 15 | 7.9 |
| 16 | 7.8 |
| 17 | 7.7 |
| 20 | 7.5 |
| 22 | 8.3 |

TABLE II-continued

INHIBITION OF THE CONTRACTION OF THE URETHRA

| Compound N° | -log $K_b$ |
|---|---|
| 25 | 7.6 |
| 27 | 7.6 |
| 38 | 7.5 |
| 39 | 7.3 |
| 42 | 7.68 |
| 45 | 8.3 |
| 46 | 7.5 |
| 47 | 7.07 |
| 48 | 7.02 |
| 50 | 6.92 |

Test of the Contraction of the Portal Vein and Aorta of the Rat:

The aorta and the portal vein are extracted from male Sprague Dawley rats (275–350 g, Charles River, France) after cervical dislocation and cleaned of the surrounding connective tissues. Longitudinal bands (one per animal) of the portal vein (3 mm wide, 10–15 mm long) and rings free of the endothelium (≈2 mm wide) of the aorta are suspended (tension: portal vein=0.5 g; aorta=2 g) in organ baths containing 10 ml of physiological solution (composed of NaCl (118 mM), KCl (4.7 mM), $CaCl_2$ (2.5 mM), $KH_2PO_4$ (1.2 mM), $MgSO_4$ (1.2 mM), $NaHCO_3$ (25 mM), glucose (11 mM)) at 37° C. and gassed with 95% $O_2$/5% $CO_2$. The contractile responses are measured using force displacement transducers either coupled to a Gould 8000S polygraph or connected to a data retrieval system (IOS, Dei Lierre, Mitry-Mory, France). A one hour period of equilibration or equalization is provided before the experiment. After equalization, the preparations are sensitized by a submaximal concentration of phenylephrine (1 μM for the aorta; 3 μM for the portal vein). When the contraction provoked by the phenylephrine is stable, a relaxation defect after the addition of carbachol (10 μM) indicates a successful disorganisation of the endothelium of the aorta. Seventy five minutes, after the sensitization, a concentration-effect curve for the phenylephrine is established. In order to determine the effect of the test compounds, different preparations are used in parallel. One preparation serves as a control whilst the others receive different test compounds introduced into the bath 60 minutes before the aministration of the phenylephrine.

The results are expressed as averages ±S.E.M. or percentage of contraction. The maximum contractile response of each preparation which was subjected to a test compound is determined by comparing the response provoked by the application of a sensitizing concentration of phenylephrine with the response provoked in the control preparation (which has only received phenylephrine). The $EC_{50}$ values are calculated from the maximum contractile response by computer analysis using a linear regression over the average tension values. The dissociation constants ($K_b$) of the test compounds are determined for each test compound according to the following equation: $K_b$=[B]/(dose ratio—1); in which [B] is the concentration of test compound and (dose ratio) is the $EC_{50}$ of the agonist in the presence of test compound divided by the control $EC_{50}$. Table III gives the $K_b$ of Compound 45 and of the $\alpha_1$-antagonist, Prazosin (Sigma, Clery en Vescin, France).

TABLE III

| | Compound 45 | Prazosin |
|---|---|---|
| $K_b$ (Aorta) | 45 nM | 5 pM |
| $K_b$ (Portal vein) | 1.4 nM | 400 pM |
| Selectivity $K_b$ (Aorta)/$K_b$ (Vein) | 32 | 0.01 |

Test of the Contraction of the Aorta and Portal Vein of the Rabbit:

The aorta and the portal vein are extracted from male New-Zealand rabbits (2.5–3.5 kg, Dombes Romans, France) after cervical dislocation and cleaned of the surrounding connective tissues. Longitudinal bands (four per animal, 3 mm wide, 10–15 mm long) or rings free of the endothelium (1 mm wide) of the aorta are suspendued (tension: portal vein=0.5 g; aorta=2 g) in organ baths containing 10 ml of physiological solution (composed of NaCl (118 mM), KCl (4.7 mM), $CaCl_2$ (2.5 mM), $KH_2PO_4$ (1.2 mM), $MgSO_4$ (1.2 mM), $NaHCO_3$ (25 mM), glucose (11 mM)) at 37° C. and gassed with 95% $O_2$/5% $CO_2$.). The contractile responses are measured using force displacement transducers coupled to a Gould RS3400 polygraph. A one hour period of equilibration or equalization is provided before the experiment. After equalization, the preparations are sensitized by a submaximal concentration of phenylephrine (1 μM for the portal vein; 3 μM for the aorta). When the contraction provoked by the phenylephrine is stabilized, carbachol (10 μM) is administered with the aim of controlling the disorganisation of the endothelium in the vessels. Seventy five minutes after the sensitization, a concentration-effect curve for the phenylephrine is established. In order to determine the effect of the test compounds, different preparations are used in parallel. One preparation serves as a control whilst the others receive different concentrations of test compounds introduced into the bath 60 minutes before the phenylephrine.

The results are expressed as averages ±S.E.M. or percentage of contraction. The maximum contractile response of each preparation having been subjected to a test compound is determined by comparing the response triggered by the application of the sensitizing concentration of phenylephrine with the response triggered in the control preparation (which has only received phenylephrine). The $EC_{50}$ values are calculated from the maximum contractile response by computer analysis using a linear regression over the average tension values. The dissociation constants ($K_b$) of the test compounds are determined for each antagonist according to the following equation: $K_b$=[B]/(dose ratio—1); in which [B] is the concentration of test compound and (dose ratio) is the $EC_{50}$ of the agonist in the presence of test compound divided by the control $EC_{50}$. Table IV gives the $K_b$ of Compound 45 and of Prazosin.

TABLE IV

| | Compound 45 | Prazosin |
|---|---|---|
| $K_b$ (Aorta) | 63 nM | 2 nM |
| $K_b$ (Portal vein) | 1.6 nM | 4 nM |
| Selectivity $K_b$ (Aorta)/$K_b$ (Vein) | 40 | 0.5 |

Test of the Contraction of the Saphenous Vein of the Rabbit:

The caudal saphenous vein is extracted from male New Zealand rabbits (2.5 to 3 kg, Dombes Romans, France) after cervical dislocation and cleaned of the surrounding connective tissues. 2–3 mm wide rings are cut under a dissection lens. The rings are suspendued under a tension of 1 g, at 37° C. in organ baths containing 10 ml of physiological solution (composed of NaCl (118 mM), KCl (4.7 mM), $CaCl_2$ (2.5 mM), $KH_2PO_4$ (1.2 mM), $MgSO_4$ (1.2 mM), $NaHCO_3$ (25 mM), glucose (11 mM)) at 37° C. and gassed with 95% $O_2$/5% $CO_2$. The contractile responses are measured using force displacement transducers coupled to a Gould RS3400 polygraph. The endothelium is removed by slowly rolling with small forceps over the luminal surface of the arterial rings and by perfusing a gentle flow of carbogen for 5 minutes through the vein. A one hour period of equilibration or equalization is provided before the experiment. During this equalization period, the tension of the venous rings is left to relax and the final tension is maintained at 0.5 g. After equalization, the preparations are sensitized by a submaximal concentration (3 $\mu$M) of phenylephrine. When the contraction triggered by the phenylephrine is stabilized, carbachol (10 $\mu$M) is administered in order to control the disorganisation of the endothelium in the vessels. Seventy five minutes after the sensitization, a concentration-effect curve for the phenylephrine is established. In order to determine the effect of the test compounds, different preparations are used in parallel. One preparation serves as a control whilst the others receive different test compounds introduced into the bath 60 minutes before the administration of the phenylephrine The results are expressed as averages ±S.E.M. or percentage of contraction. The maximum contractile response of each preparation having been subjected to a test compound is determined by comparing the response triggered by the application of a sensitizing concentration of phenylephrine with the response triggered in the control preparation (which has only received phenylephrine). The $EC_{50}$ values are calculated from the maximum contractile response by computer analysis using a linear regression over the average tension values. The dissociation constants ($K_b$) of the test compound are determined for each test compound according to the following equation: $K_b$=[B]/(dose ratio—1); in which [B] is the concentration of test compound and (dose ratio) is the $EC_{50}$ of the agonist in the presence of test compound divided by the control $EC_{50}$. Table V gives the $K_b$ of Compound 45 and of Prazosin.

TABLE V

|  | Compound 45 | Prazosin |
|---|---|---|
| $K_b$ (Saphenous vein) | 15 nM | 13 nM |
| Selectivity | 8.4 | 3.3 |
| $K_b$ (Salphenous vein)/$K_b$ (Portal vein) |  |  |

Other Embodiments:

It is understood that, whilst the invention was described in conjunction with its detailed description, this description is provided for illustration and does not limit the scope of the invention, which is defined by the scope of the attached claims. Other aspects, advantages and modifications are included in the claims.

What is claimed is:

1. A compound selected from the group consisting of a compound of formula

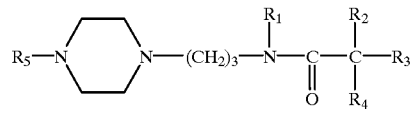

wherein $R_1$ is selected from the group consisting of hydrogen, alkyl of 1 to 6 carbon atoms and arylalkyl of 1 to 6 alkyl carbon atoms, $R_2$ is selected from the group consisting of hydrogen, alkyl of 1 to 6 carbon atoms, —$OR_6$, —$S(O)_m$—$R_6$, —$NHS(O)_n$—$R_6$,

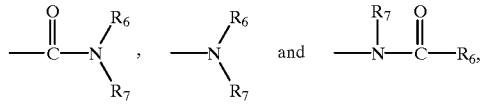

m is an integer from 0 to 2, n is 1 or 2, $R_3$ and $R_4$ are individually selected from the group consisting of hydrogen, unsubstituted or substituted alkyl of 1 to 6 carbon atoms, unsubstituted or substituted cycloalkyl of 3 to 10 carbon atoms, unsubstituted or substituted aryl, unsubstituted or substituted aralkyl of 1 to 6 alkyl carbon atoms, and unsubstituted or substituted heterocycle alkyl of 1 to 6 alkyl carbon atoms, said substituents being selected from the group consisting of halogen, alkyl of 1 to 6 carbon atoms, —$OR_6$, —$SR_6$,

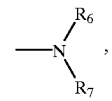

—CN, —$NO_2$, —$CF_3$, heterocycle and aryl or $R_3$ and $R_4$ taken together the carbon atoms to which they are attached form aryl or unsubstituted or substituted heterocycle with up to 4 members of the group consisting of —O—, —S— and —N═, the substituent being —OH or alkyl or hydroxyalkyl of 1 to 6 carbon atoms, $R_5$ is phenyl substituted with at least one member of the group consisting of alkyl of 1 to 6 carbon atoms, cycloalkyl of 3 to 10 carbon atoms, hydroxyalkyl of 1 to 6 carbon atoms, hydroxy cycloalkyl of 3 to 10 carbon atoms, alkoxy alkyl of 2 to 12 carbon atoms, alkoxy cycloalkyl of 1 to 6 alkoxy carbon atoms, halogen, —$OR_6$, —$SR_6$, —CN and

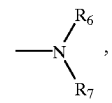

$R_6$ and $R_7$ are individually selected from the group consisting of hydrogen, unsubstituted or substituted alkyl of 1 to 6 carbon atoms, unsubstituted or substituted aryl and unsubstituted or substituted aralkyl of 1 to 6 alkyl carbon atoms, said substituents being selected from the group consisting of alkyl of 1 to 6 carbon atoms, halogen and alkoxy of 1 to 6 carbon atoms and its non-toxic, pharmaceutically acceptable salts with the proviso if, $R_2$ is $OR_6$, $R_6$ is not aryl, if $R_2$ is $OR_6$ and $R_6$ represents H and one of $R_3$ and $R_4$ is aryl, arylalkyl or cycloalkyl, the other is not aryl, arylalkyl or cycloalkyl and if $R_2$ is H, $OR_6$ or —$NR_6R_7$, one of $R_3$ or $R_4$ is phenyl unsubstituted or mono- or poly-substituted by alkoxy, alkyl or halogen, the other is not H, alkyl, cycloalkyl, or phenyl unsubstituted or mono- or poly-substituted by alkoxy, alkyl or halogen.

2. A compound of claim 1 wherein $R_1$ is hydrogen or alkyl of 1 to 6 carbon atoms.

3. A compound of claim 2 wherein $R_2$ is selected from the group consisting of hydrogen, alkyl of 1 to 6 carbon atoms, —OH or aryl alkoxy of 1 to 6 alkoxy carbon atoms, alkylthio of 1 to 6 carbon atoms, —NH$_2$, —NHSO$_2$R'$_6$, R'$_6$ is alkyl of 1 to 6 carbon atoms or aralkyl of 1 to 6 alkyl carbon atoms, aralkyl

of 1 to 6 alkyl carbon atoms,

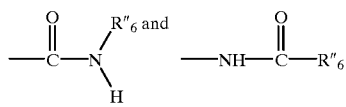

and R''$_6$ is aralkyl of 1 to 6 alkyl carbon atoms.

4. A compound of claim 3 wherein $R_5$ is phenyl substituted with a member selected from the group consisting of alkyl of 1 to 6 carbon atoms, —CN, halogen, hydroxyl alkyl of 1 to 6 carbon atoms, hydroxy cycloalkyl of 3 to 10 carbon atoms, alkoxy alkyl of 2 to 12 carbon atoms and alkoxy of 1 to 6 carbon atoms.

5. A compound of claim 4 wherein $R_1$ is hydrogen and $R_5$ is 2,5-dimethyl-phenyl.

6. A compound of claim 5 wherein R is —OH or alkoxy of 1 to 6 carbon atoms or aralkoxy of 1 to 6 alkoxy carbon atoms.

7. A compound of claim 5 wherein $R_3$ is alkyl of 1 to 6 carbon atoms and $R_4$ is phenyl.

8. A compound of claim 4 wherein $R_3$ and $R_4$ together with the carbon to which they are attached form an unsubstituted or substituted aryl.

9. A compound of claim 8 wherein $R_1$ is hydrogen and $R_5$ is 2-methoxy-phenyl or 2,5-dimethyl-phenyl.

10. A compound of claim 9 wherein $R_2$ is —OH, alkoxy of 1 to 6 carbon atoms and aralkoxy of 1 to 6 alkoxy carbon atoms.

11. A compound of claim 4 wherein $R_3$ and $R_4$ are individually selected from the group consisting of hydrogen, unsubstituted or substituted alkyl of 1 to 6 carbon atoms, unsubstituted or substituted cycloalkyl of 3 to 10 carbon atoms, unsubstituted or substituted aryl where the substitutent is halogen, alkoxy of 1 to 6 carbon atoms or aryl.

12. A compound of the group consisting of

1

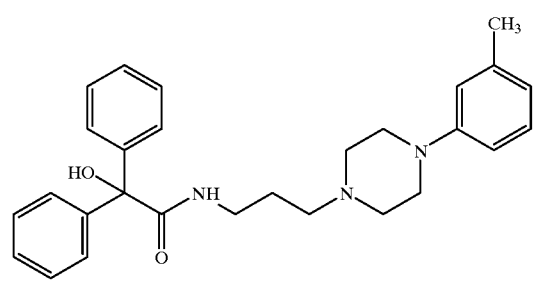

2

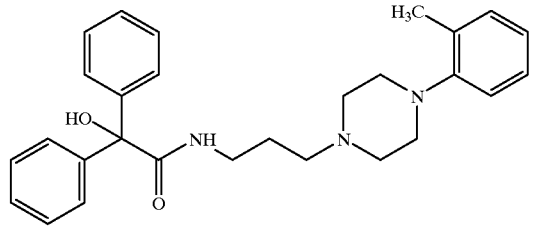

3

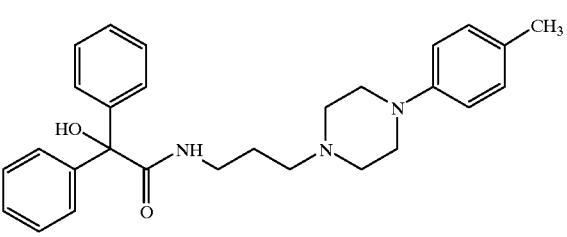

4

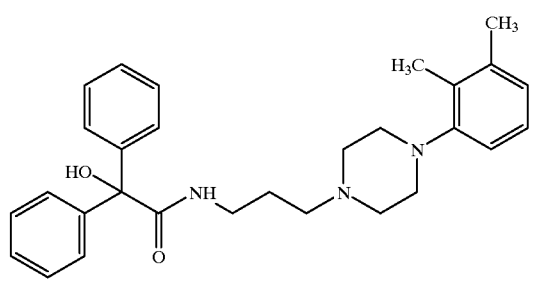

5

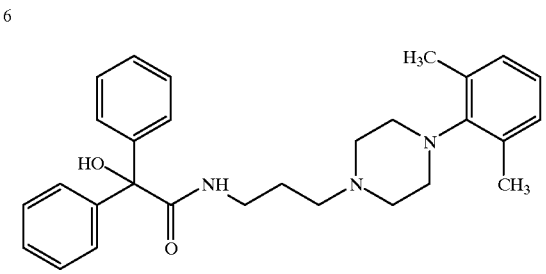

6

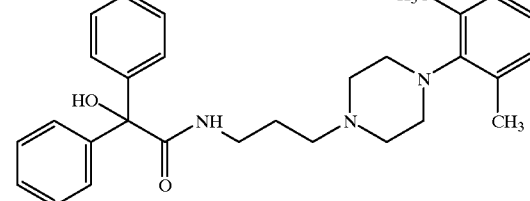

-continued
7
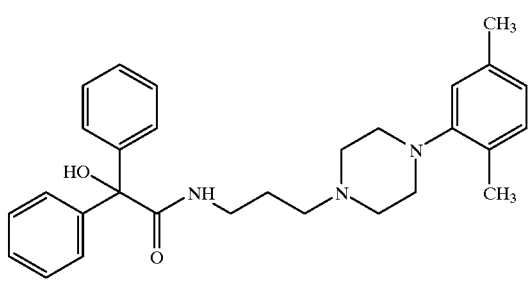
12
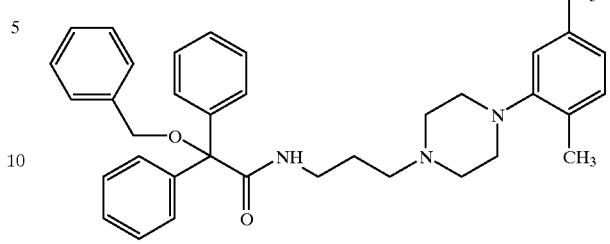
8
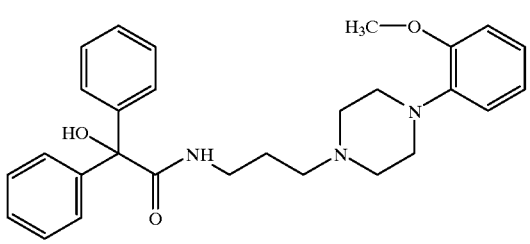
13
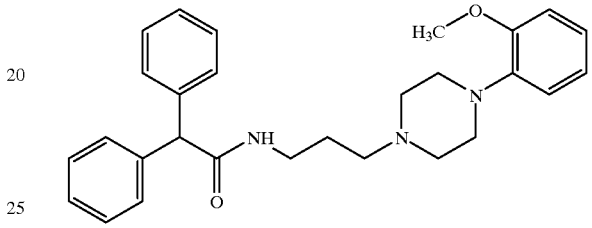
excluded compound
9
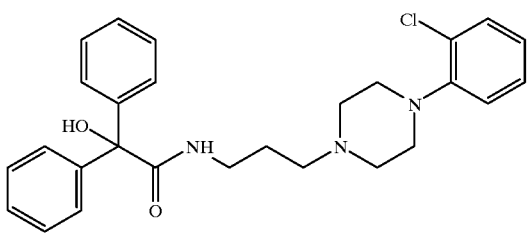
14
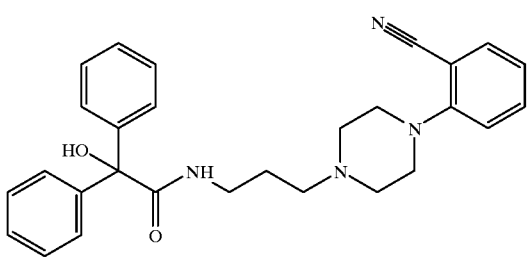
10
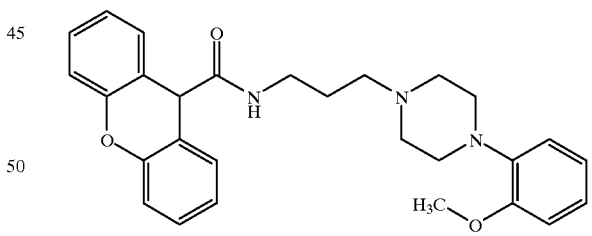
15
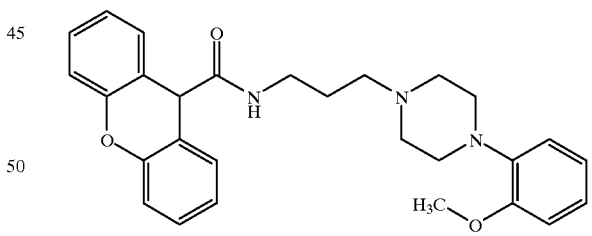
11
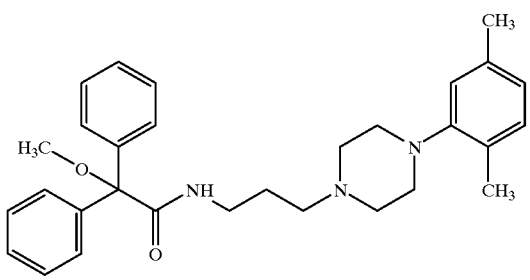
16
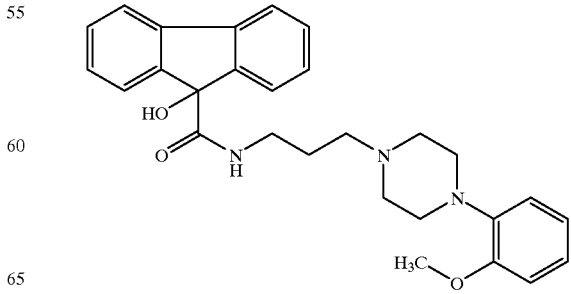

17
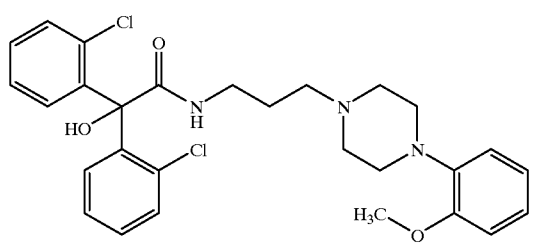
18
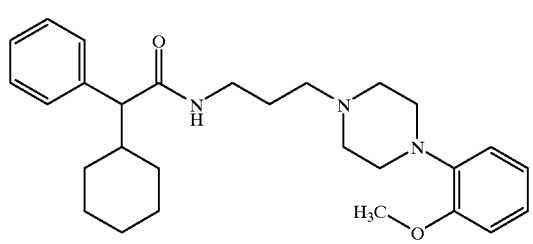
19
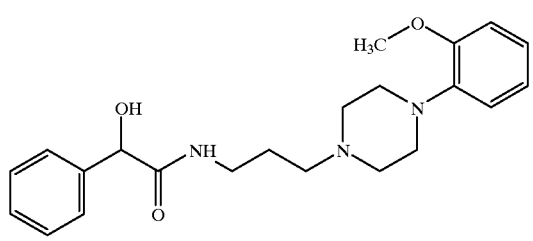
20
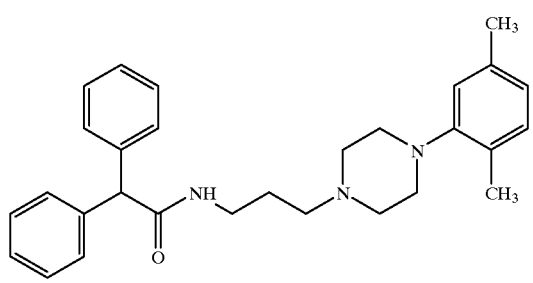
21
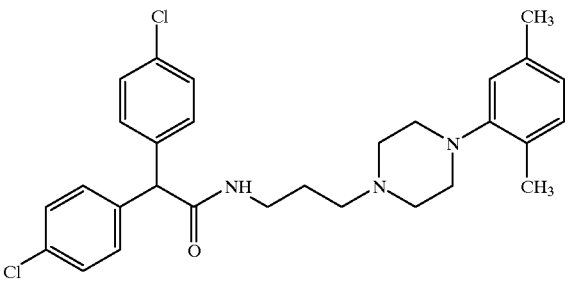
22
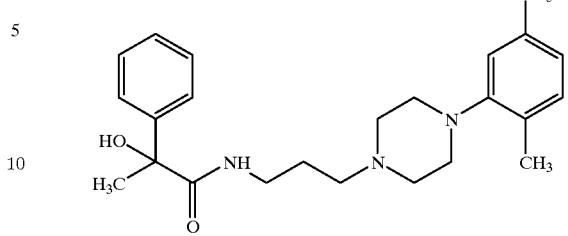
23
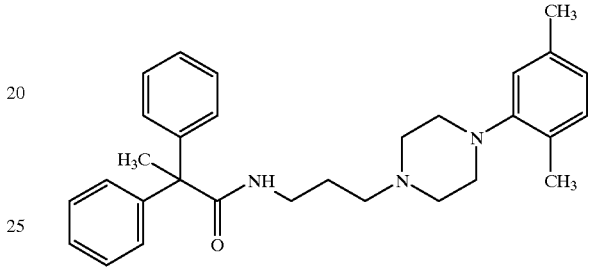
24
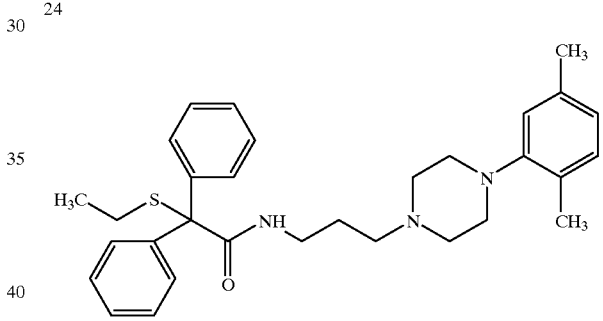
25
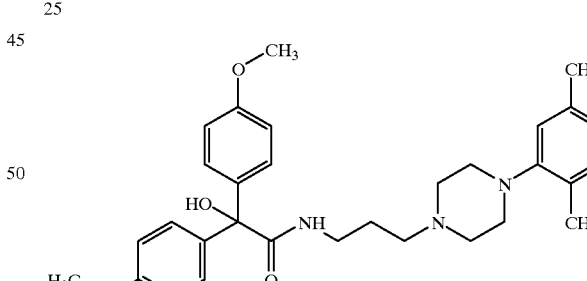
26
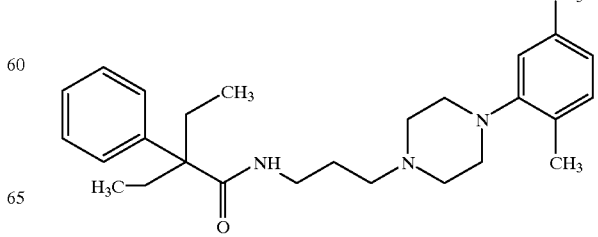

27
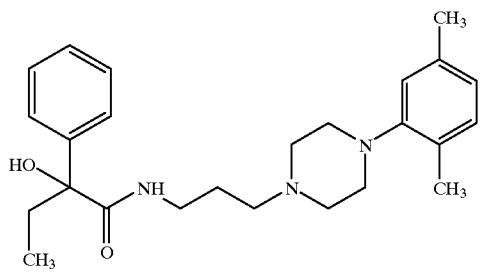
28
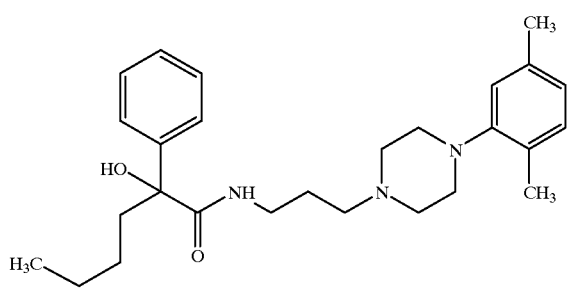
29
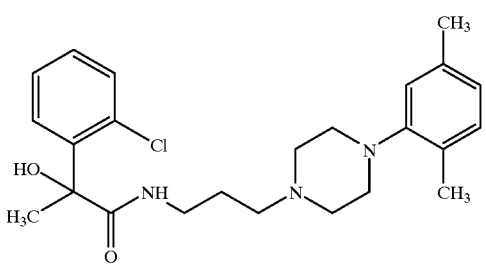
30
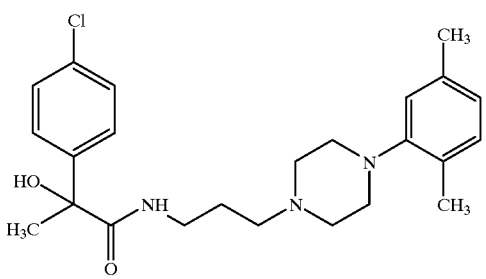
31
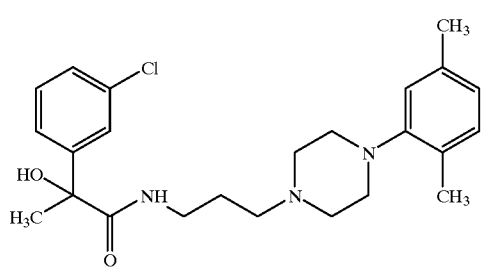
32
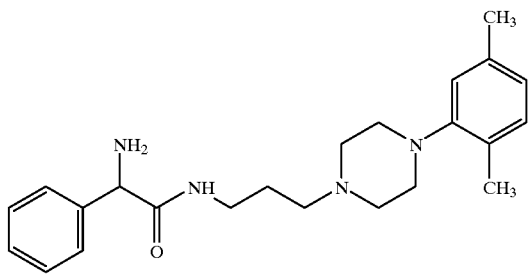
33
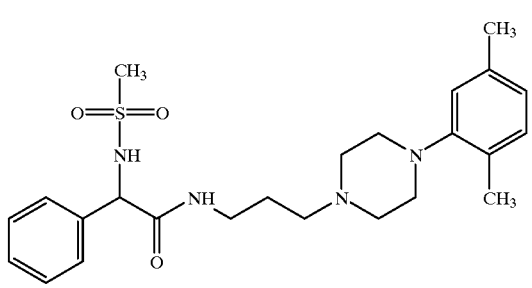
34
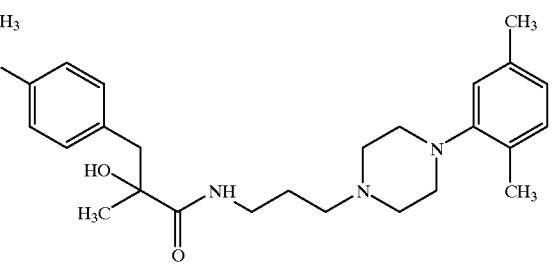
35
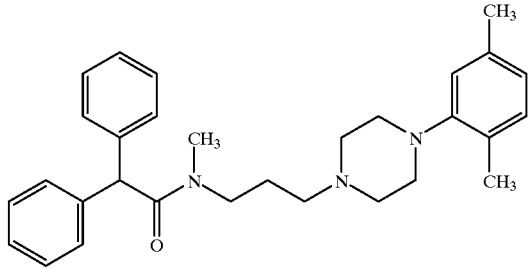
36
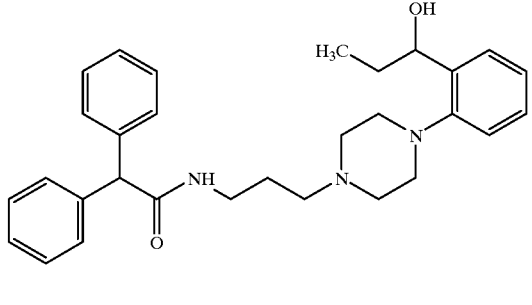

37
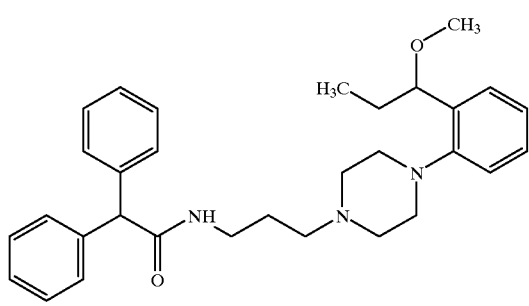
38
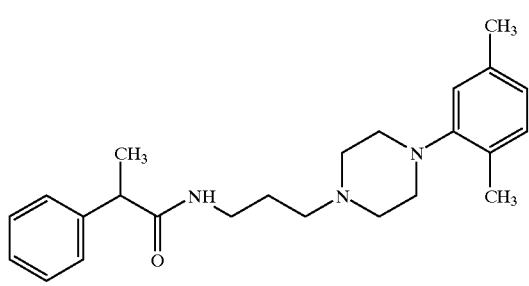
39
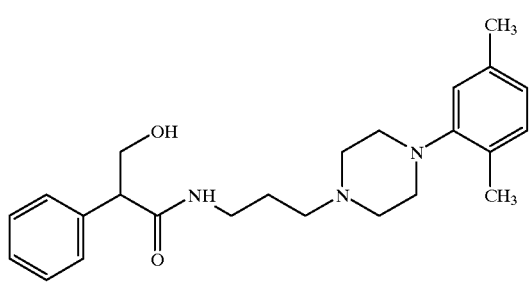
40
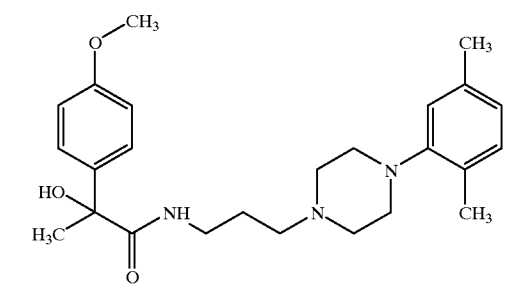
41
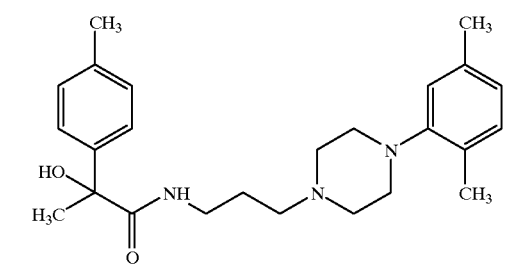
42
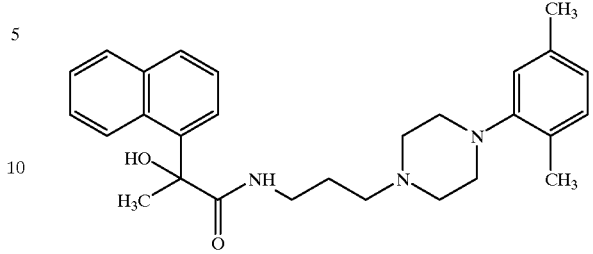
43
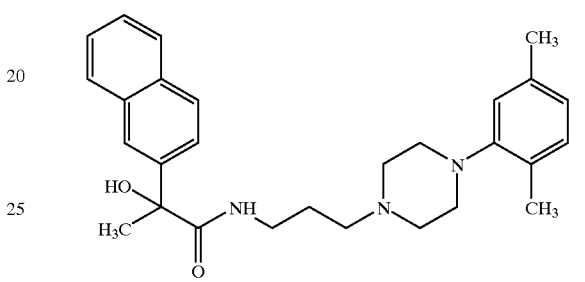
44
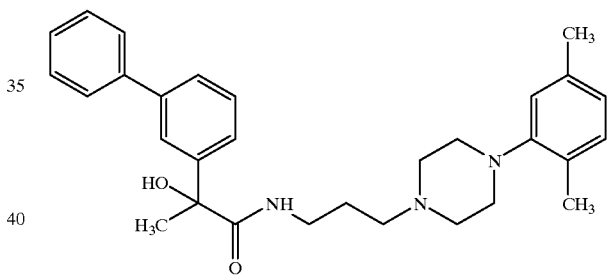
45
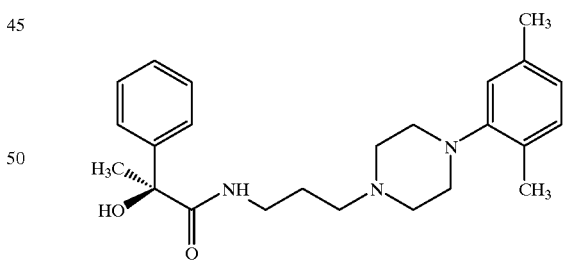
46
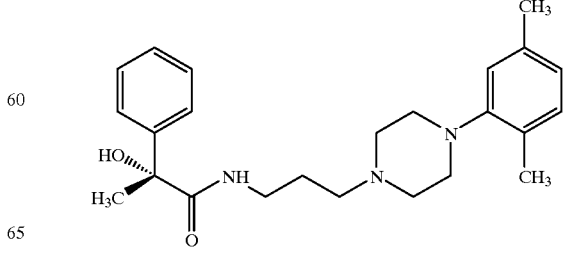

47
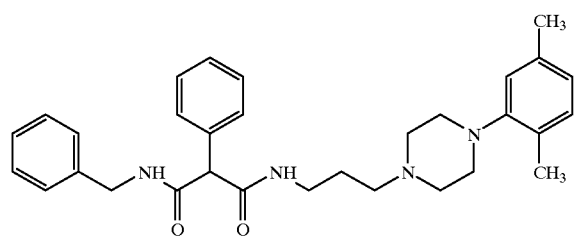
48
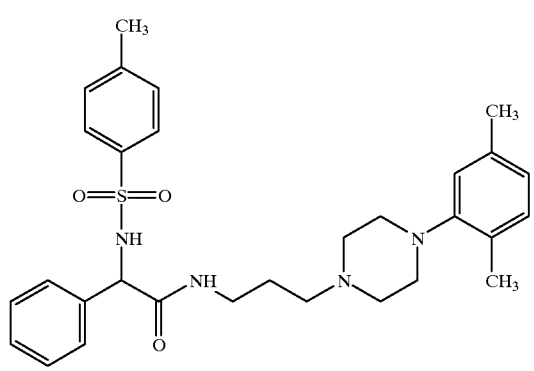
49
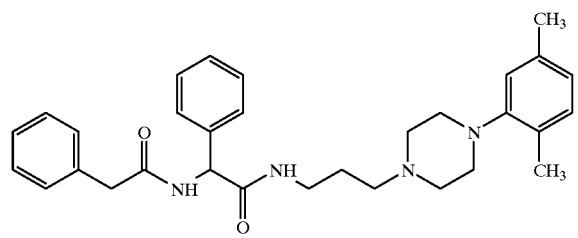
50
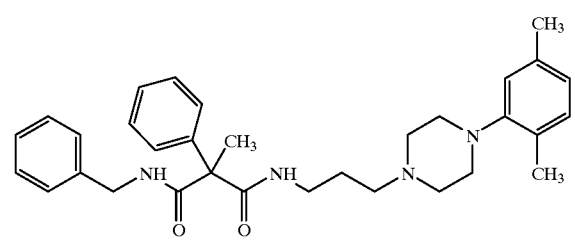
51
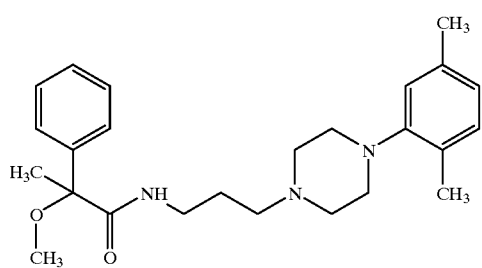
52
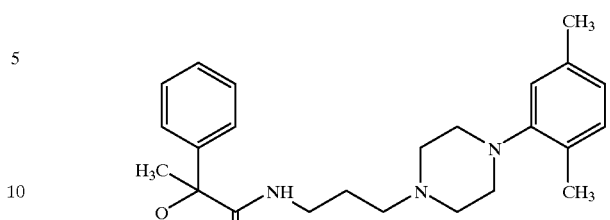
53
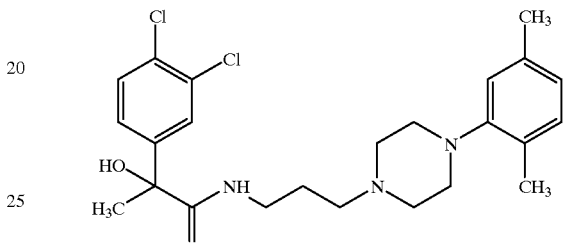
54
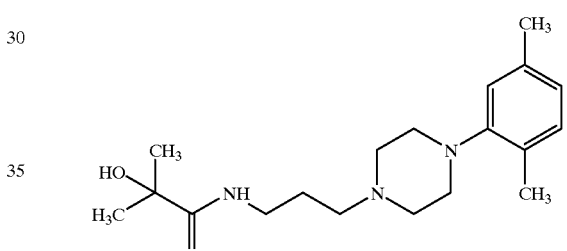
55
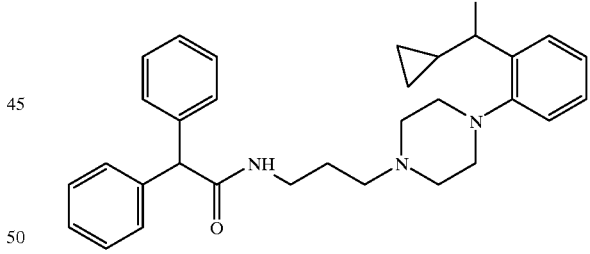
56
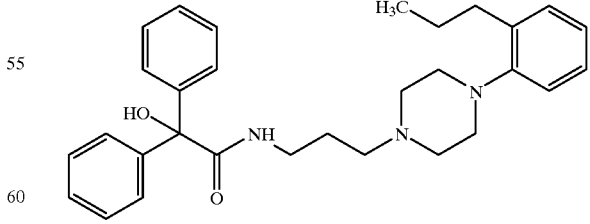
13. Compound according to claim 1, in which said compound corresponds to the formula:

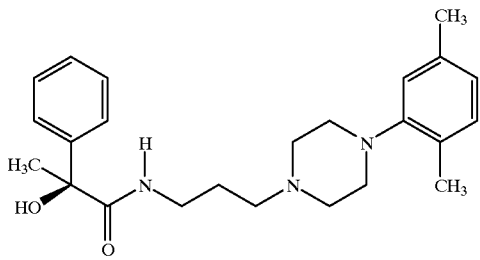

or one of its pharmaceutically acceptable salts.

14. Pharmaceutical composition containing a compound of formula Ia:

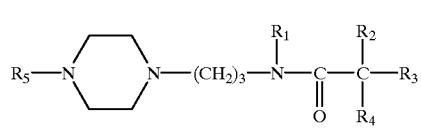

(Ia)

in which $R_1$ represents a hydrogen, a lower alkyl, or an aryl-lower alkyl;

$R_2$ represents a hydrogen, a lower alkyl, $OR_6$, $S(O)_m R_6$ in which m is 0, 1 or 2, $NHS(O)_n R_6$ in which n is 1 or 2, $OC(O)R_6$, $C(O)NR_6 R_7$, $NR_6 R_7$ or $N(R_7)C(O)R_6$;

each of $R_3$ and $R_4$, independent of each other, represents a hydrogen or one of the following substituted or non-substituted compounds: a lower alkyl, a cycloalkyl, an aryl, an aryl-lower alkyl, a heterocycle, or a heterocycle-lower alkyl, in which said substituent is a lower alkyl, a halogen, $OR_6$, $SR_6$, $NR_6 R_7$, CN, $NO_2$, $CF_3$, a heterocycle, or an aryl, or $R_3$ and $R_4$, together with the carbon atom to which they are jointly linked, form an aryl or a heterocycle substituted or non-substituted, in which said substituent is a lower alkyl, OH, or a hydroxy-lower alkyl;

$R_5$ is a substituted or non-substituted aryl, in which said substituent is a lower alkyl, a cyclo-alkyl, a hydroxyl-lower alkyl, a hydroxy-cycloalkyl, an alkoxy-lower alkyl, an alkoxy-cycloalkyl, a halogen, $OR_6$, $SR_6$, $NR_6 R_7$ or CN; and each $R_6$ and $R_7$, independent of each other, represents a hydrogen or one of the following substituted or non-substituted compounds: a lower alkyl, an aryl or an aryl-lower alkyl in which said substituent is a lower alkyl, a halogen, or a lower alkoxy; and their pharmaceutically acceptable salts.

15. A pharmaceutical composition according to claim 14, in which $R_1$ represents a hydrogen and $R_5$ represents 2,5-dimethyl-phenyl.

16. A pharmaceutical composition according to claim 15, in which $R_2$ represents $OR_6$ in which $R_6$ represents a hydrogen, a lower alkyl, or an aryl-lower alkyl, $R_3$ represents a lower alkyl and $R_4$ represents phenyl.

17. A pharmaceutical composition according to claim 16, in which said compound corresponds to the formula:

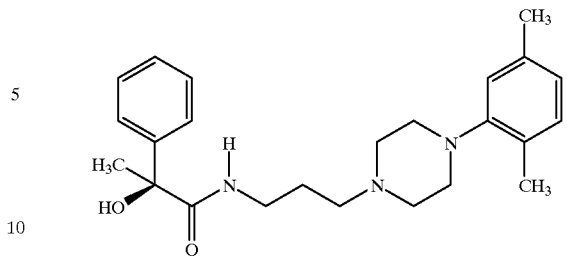

18. Treatment method for benign hyperplasia of the prostate, said method comprising the administration of a pharmaceutical composition according to claim 14.

19. A method of treating benign hyperplasia of the prostate of a male warm-blooded animal comprising administering to male warm-blooded animals an amount of a compound of claim 1 sufficient to treat benign hyperplasia of the prostate.

20. A method of treating portal hypertension in warm-blooded animals comprising administering to warm-blooded animals a portal hypertensively effective amount of a compound of claim 1.

21. A method of treating cirrhosis in warm-blooded animals comprising administering to warm-blooded animals an amount of a compound of claim 1 to treat cirrhosis.

22. Method according to claim 20, said method comprising the administration to said patient of a pharmaceutical composition according to claim 16.

23. Method according to claim 20, said method comprising the administration to said patient of a pharmaceutical composition according to claim 17.

24. Method according to claim 20, said method comprising the administration to said patient of a pharmaceutical composition according to claim 18.

25. Treatment method for portal hypertension, said method comprising the administration of an effective therapeutic quantity of a compound having a $K_b$ of the inhibition of the contraction of the portal vein of the rat which is at least five times lower than the $K_b$ of said compound for the inhibition of the contraction of the aorta of the rat, in which said compound links to the $\alpha_1$-adrenergic receptor with a Ki of at least 1 $\mu$M.

26. Method according to claim 25, in which said compound has a $K_b$ of the inhibition of the contraction of the portal vein of the rat which is at least twenty times lower than the $K_b$ of said compound for the inhibition of the contraction of the aorta of the rat.

27. Method according to claim 25, in which said compound also has a $K_b$ of the inhibition of the contraction of the portal vein of the rabbit which is at least five times lower than the $K_b$ of said compound for the inhibition of the contraction of the aorta of the rabbit.

28. Method according to claim 26, in which said compound has a $K_b$ of the inhibition of the contraction of the portal vein of the rabbit which is at least twenty times lower than the $K_b$ of said compound for the inhibition of the contraction of the aorta of the rabbit.

29. Method according to claim 25, in which said compound also has a $K_b$ of the inhibition of the contraction of the portal vein of the rabbit which is at least two times lower than the $K_b$ of said compound for the inhibition of the contraction of the saphenous vein of the rabbit.

30. Method according to claim 25, in which said method comprises the administration of a compound of formula:

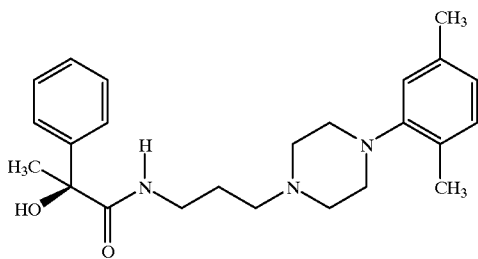

31. Treatment method for portal hypertension, said method comprising the administration of an effective therapeutic quantity of a compound having a $K_b$ of the inhibition of the contraction of the portal vein of the rabbit which is at least five times lower than the $K_b$ of said compound for the inhibition of the contraction of the aorta of the rabbit, in which said compound links to the $\alpha_1$-adrenergic receptor with a Ki of at least 1 $\mu$M.

32. Method according to claim 31, in which said compound has a $K_b$ of the inhibition of the contraction of the portal vein of the rabbit which is at least twenty times lower than the $K_b$ of said compound for the inhibition of the contraction of the aorta of the rabbit.

33. Method according to claim 32, in which said compound also has a $K_b$ of the inhibition of the contraction of the portal vein of the rabbit which is at least two times lower than the $K_b$ of said compound for the inhibition of the contraction of the saphenous vein of the rabbit.

34. Treatment method for portal hypertension, said method comprising the administration of an effective therapeutic quantity of a compound having a $K_b$ of the inhibition of the contraction of the portal vein of the rabbit which is at least two times lower than the $K_b$ of said compound for the inhibition of the contraction of the saphenous vein of the rabbit in which said compound links to the a $\alpha_1$-adrenergic receptor with a Ki of at least 1 $\mu$M.

35. A method for treating portal hypertension comprising administering an effective therapeutic quantity of a compound of formula $I_M$

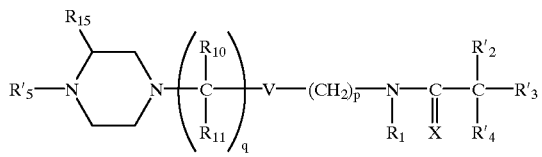

wherein $R_1$ is selected from the group consisting of hydrogen, alkyl of 1 to 6 carbon atoms, an aryl-lower alkyl, —CN, —$CO_2R_9$, —$CON(R_9)_2$, cycloalkyl and —$(CH_2)_pCO_2R_9$, $R'_2$ is selected from the group consisting of hydrogen, alkyl of 1 to 6 carbon atoms, —$OR_6$, —$S(O)_mR_6$ in which m is 0, 1 or 2, —$NHS(O)_nR_6$ in which n is 1 or 2, —$OC(O)R_6$, —$C(O)NR_6R_7$, —$NR_6R_7$, —$N(R_7)C(O)R_6$, —$CO_2R_{10}$, —$(CH_2)_pCO_2R_{10}$, —$OR_{12}$, —$NR_{12}R_{13}$, $(CH_2)_pCN(R_{10})_2$ or $CR'_2$ forms a cyclopropyl cycle and one of $R'_3$ and $R'_4$ does not exist, $R'_3$ and $R'_4$ are individually selected from the group consisting of hydrogen, alkyl of 1 to 6 carbon atoms, alkoxy of 1 to 6 carbon atoms, a cycloalkyl of 3 to 7 carbon atoms, an aryl, an aryl-lower alkyl, a heterocycle, a heterocycle-lower alkyl and $NR'_{10}R''_{10}$, unsubstituted or substituted in which said substituent is selected from the group consisting of lower alkyl optionally substituted by at least one halogen —$OR_6$, —$SR_6$, —$NR_6R_7$, —CN, —$NO_2$, a heterocycle, an aryl or a methylenedioxy on two adjacent carbons, or $R'_3$ and $R'_4$ together with the carbon atom to which they are attached form an aryl or a heterocycle substituted or non-substituted, in which said substituent is a lower alkyl, —OH, or hydroxy-lower alkyl;

$R'_5$ is is selected from the group consisting of alkyl, aryl radical and heterocycle substituted or non-substituted, in which said substituent is selected from the group consisting of alkyl optionally substituted by at least one halogen, cyclo-alkyl, a hydroxyl-lower alkyl, a hydroxy-cycloalkyl, an alkoxy-lower alkyl, an alkoxy-cycloalkyl, a halogen, a methylenedioxy on two adjacent carbons, —$OR_6$, —$SR_6$, —$NR_6R_7$, —CN, —$CO_2R_{10}$, —$(CH_2)_pCON(R_{10})_2$ and —$(CH_2)_pCO_2R_{10}$, $R_6$ and $R_7$ are individually selected from the group consisting of a) hydrogen, b) lower alkyl, an aryl and an aryl-lower alkyl, all unsubstituted or substituted in which said substituents are lower alkyl or a lower alkoxy or halogen; $R_9$, $R_{10}$, $R'_{10}$, $R''_{10}$ and $R_{11}$ are individually selected from the group consisting of hydrogen, lower alkyl and cycloalkyl, the alkyl and cycloalkyl unsubstituted or substituted by at least one halogen;

$R_{12}$ and $R_{13}$ are individually selected from the group consisting of hydrogen, a lower alkyl and cycloalkyl substituted or non-substituted, —CHO, —$COR_{10}$, —$CONR_{10}R_{11}$ and $(CH_2)_pOR_{10}$, V is selected from the group consisting of

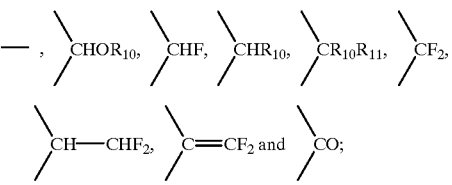

q is an integer from 0 to 3;

p is an integer from 0 to 3;

X is oxygen, sulphur or $NR_{14}$, $R_{14}$ is hydrogen, cyano or —$SOR_{10}$, $R_{15}$ is hydrogen or hydroxy;

it being understood that when n and p=O, V is not

and its pharmaceutically acceptable salts.

36. Treatment method for cirrhosis, said method comprising the administration of an effective therapeutic quantity of a compound of formula $I_M$ as defined in claim 33.

37. Treatment method for portal hypertension or cirrhosis, said method comprising the administration of an effective therapeutic quantity of a compound of formula $I_N$:

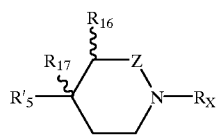

$I_N$ in which R'₅, R₉ and R₁₀ have the meaning indicated in claim 35;

Z represents a CHR₁₈ or NHR₉ radical;

R_x is chosen from the radicals

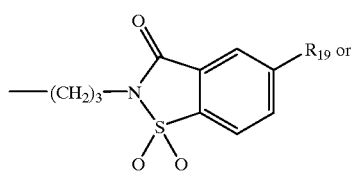

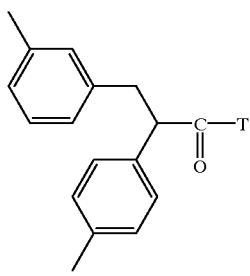

in which R₁₉ represents a hydrogen atom or a chlorine atom;

T represents an —NH—(CH₂)₃ or

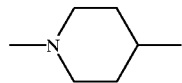

radical;

R₁₆, R₁₇ and R₁₈ are chosen from hydrogen and the cyano, aryl, heterocycle, CONR₉R₁₀, CO₂R₉ or SO₂R₉ radicals.

38. A method for treating portal hypertension comprising administering an effective therapeutic quantity of a compound of the formula

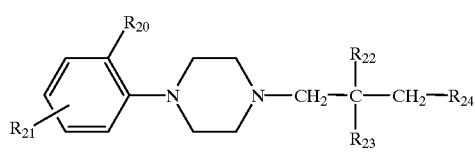

$I_R$ in which

R₂₀ is selected from the group consisting of a) acetylamino, amino, cyano, trifluoroacetylamino, halogen, hydrogen, hydroxy, nitro, methylsulphonylamino, 2-propynyloxy and b) non-substituted or substituted with 1 to 3 halogens, alkyl, a lower cycloalkyl, a cycloalkyl-lower lower alkyl, a lower alkoxy, a cycloalkyloxy, a cycloalkyl-lower alkoxy or a lower alkylthio; c) aryl, an aryl-alkyl, a heterocycle, a heterocycle-lower alkyl, an aryloxy, an aryl-lower alkoxy, a heterocycle-oxy or a heterocycle-lower alkoxy, in which the aryl radical or the heterocycle are optionally substituted by one or two of halogen and cyano;

R₂₁ is selected from the group consisting of CN, a halogen, a hydrogen, hydroxy and lower alkyl and lower alkoxy optionally substituted with 1 to 3 halogens;

R₂₂ and R₂₃ are individually hydrogen or methyl or, together, ethylene;

R₂₄ is selected from the group consisting of

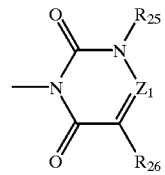

$I_{ra}$

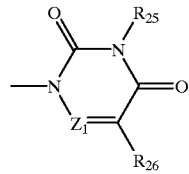

$I_{Rb}$

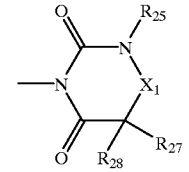

$I_{Rc}$

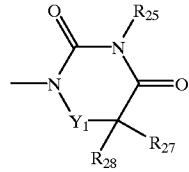

$I_{Rd}$

X₁ is —C(O), —CH₂ or —CH(OH);

Y₁ is —CH₂ or —CH(OH);

Z₁ is N or C(R₂₉), in which R₂₉ is hydrogen, a lower alkyl or hydroxy;

R₂₅ is selected from the group consisting of a) hydrogen, b) optionally substituted by one to three halogen, a lower alkyl, a cycloalkyl, a cycloalkyl-lower alkyl; c) an aryl, a heterocycle, an aryl-lower alkyl or a heterocycle-lower alkyl, in which the aryl or the heterocycle are optionally substituted by one to three members selected from the group consisting of halogen cyano, a lower alkoxy, a lower alkyl and aryl;

R₂₆ is selected from the group consisting of a) —R₃₀C(O)—, carbamoyl, cyano, di(lower alkyl)amino; halogen, hydrogen, hydroxy, hydroxyiminomethyl, $R_{30}S$, $R_{30}SO_2$; b) substituted by one to three halogen, hydroxy or a lower alkoxy, or non-substituted lower alkyl, a cycloalkyl, a lower alkoxy or a lower alkoxy-lower alkyl; or c) an aryl, a heterocycle, an aryl-lower alkyl or a heterocycle-lower alkyl, in which the aryl radical or the heterocycle are optionally substituted by one to three radicals chosen from a halogen, cyano, a lower alkoxy, a lower alkyl or an aryl; or $R_{26}$ and $R_{29}$ form together the —$CH_2$—$(CH_2)_2$—$CH_2$—;

$R_{27}$ and $R_{28}$ are independently, hydrogen, hydroxy, methyl or ethyl;

$R_{30}$ is lower alkyl;

or one of its pharmaceutically acceptable salts or a of its N-oxides.

\* \* \* \* \*